(12) United States Patent
Barrow et al.

(10) Patent No.: US 8,003,653 B2
(45) Date of Patent: Aug. 23, 2011

(54) IMIDAZOLIDINONE COMPOUNDS USEFUL AS β-SECRETASE INHIBITORS FOR THE TREATMENT OF ALZHEIMER'S DISEASE

(75) Inventors: James C. Barrow, Harleysville, PA (US); Kenneth E. Rittle, Green Lane, PA (US); Phung Le Bondiskey, Lansdale, PA (US)

(73) Assignee: Merck. Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/085,174

(22) PCT Filed: Nov. 10, 2006

(86) PCT No.: PCT/US2006/043536
§ 371 (c)(1),
(2), (4) Date: May 15, 2008

(87) PCT Pub. No.: WO2007/058862
PCT Pub. Date: May 24, 2007

(65) Prior Publication Data
US 2009/0111832 A1 Apr. 30, 2009

(51) Int. Cl.
*A61K 31/496* (2006.01)
*A61K 31/4439* (2006.01)
*A61K 31/4166* (2006.01)
*C07D 403/12* (2006.01)
*C07D 401/12* (2006.01)
*C07D 235/02* (2006.01)
*C07D 233/32* (2006.01)

(52) U.S. Cl. .......... 514/254.05; 514/341; 514/386; 544/370; 546/274.4; 548/300.7; 548/324.1

(58) Field of Classification Search ............ 514/254.05, 514/341, 385; 544/370; 546/274.4; 548/300.7, 548/324.1
See application file for complete search history.

(56) References Cited

U.S. PATENT DOCUMENTS

| | | |
|---|---|---|
| 7,109,217 B2 | 9/2006 | Coburn et al. |
| 7,115,652 B2 | 10/2006 | Yang |
| 7,132,568 B2 | 11/2006 | Yang et al. |
| 7,205,336 B2 | 4/2007 | Lai et al. |
| 7,291,620 B2 | 11/2007 | Coburn et al. |
| 7,329,746 B2 | 2/2008 | Coburn et al. |
| 2005/0119227 A1 | 6/2005 | Cumming et al. |
| 2006/0149092 A1 | 7/2006 | Nantermet et al. |
| 2006/0293380 A1 | 12/2006 | Nantermet et al. |
| 2007/0088165 A1 | 4/2007 | Nantermet et al. |
| 2007/0142634 A1 | 6/2007 | Barrow et al. |

FOREIGN PATENT DOCUMENTS

| | | |
|---|---|---|
| WO | WO 2005/014540 | 2/2005 |
| WO | WO 2005/016876 | 2/2005 |
| WO | WO 2005/103020 | 11/2005 |
| WO | WO 2005/103043 | 11/2005 |
| WO | WO 2005/113484 | 12/2005 |
| WO | WO 2006/002004 | 1/2006 |
| WO | WO 2006/057945 | 6/2006 |
| WO | WO 2007/019111 | 2/2007 |

*Primary Examiner* — Kamal Saeed
*Assistant Examiner* — Kristin Bianchi
(74) *Attorney, Agent, or Firm* — Keith D. MacMillian; Gerard M. Devlin

(57) ABSTRACT

The present invention is directed to imidazolidinone compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

19 Claims, No Drawings

IMIDAZOLIDINONE COMPOUNDS USEFUL AS β-SECRETASE INHIBITORS FOR THE TREATMENT OF ALZHEIMER'S DISEASE

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to compounds useful as inhibitors of the beta secretase enzyme, and useful in the treatment of diseases in which the beta secretase enzyme is involved, such as Alzheimer's Disease.

BACKGROUND OF THE INVENTION

Alzheimer's disease is characterized by the deposition of amyloid in the brain in the form of extra-cellular plaques and intracellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to novel imidazolidinone compounds represented by general formula (I)

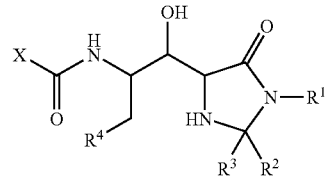

and individual enantiomers and diastereoisomers thereof, and pharmaceutically acceptable salts thereof, which are useful as inhibitors of the β-secretase enzyme.

The invention is also directed to pharmaceutical compositions which include an effective amount of a compound of formula (I), or pharmaceutically acceptable salts thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to novel imidazolidinone compounds represented by general formula (I)

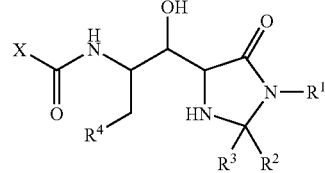

wherein $R^1$, $R^2$, $R^3$ and $R^4$ are independently selected from the group consisting of
(1) hydrogen,
(2) —$C_{1-10}$ alkyl,
(3) —$C_{2-10}$ alkenyl,
(4) $C_{2-10}$ alkynyl,
(5) $C_{6-10}$ aryl, or
(6) heteroaryl,
wherein said alkyl, alkenyl, alkynyl, aryl or heteroaryl is optionally substituted with one or more
  (a) halo,
  (b) —$C_{1-10}$ alkyl, wherein said alkyl is optionally substituted with one or more fluoro,
  (c) —$C_{3-12}$ cycloalkyl,
  (d) —OH,
  (e) —CN,
  (f) —O—$C_{1-10}$ alkyl, wherein said alkyl is optionally substituted with one or more fluoro,
  (g) —$C_{6-10}$ aryl, or
  (h) heteroaryl,
  and said aryl and heteroaryl is optionally substituted with one or more
    (i) halo,
    (ii) —OH,
    (iii) —CN,
    (iv) -$Q^1$-$C_{1-10}$ alkyl, wherein said alkyl is optionally substituted with one or more fluoro,
    (v) —$C_{1-10}$ alkyl, wherein said alkyl is optionally substituted with one or more fluoro, or
    (vi) $C_{3-12}$ cycloalkyl, and $Q^1$ is selected from the group consisting of
(A) —O—,
(B) —SO$_2$—,
(C) —NH—,
or $R^2$ and $R^3$ are linked together to form a 3-7 carbocyclic ring structure, wherein one, two or three of the ring carbon atoms may be replaced with O, S, NH, —C(=O) or SO$_2$,
and the carbocyclic ring is optionally substituted with one or more
(a) —C$_{1-10}$ alkyl,
(b) —C$_{2-10}$ alkenyl,
(c) —C$_{2-10}$ alkynyl, and
(d) —C$_{6-10}$ aryl;

X is selected from the group consisting of
(1) -(Q$^2$)$_n$-R$^5$,
wherein Q$^2$ is selected from the group consisting of
(a) —CH$_2$—, and
(b) —O—,
R$^5$ is selected from the group consisting of
(a) hydrogen
(b) —C$_{1-10}$ alkyl,
(c) —C$_{2-10}$ alkenyl,
(d) —C$_{2-10}$ alkynyl, and
(e) —C$_{6-10}$ aryl,
wherein said alkyl, alkenyl, alkynyl or aryl is optionally substituted with one or more
(i) halo,
(ii) —C$_{1-10}$ alkyl, wherein said alkyl is optionally substituted with one or more fluoro,
(iii) —C$_{3-12}$ cycloalkyl,
(iv) —OH,
(v) —CN,
(vi) —O—C$_{1-10}$ alkyl, wherein said alkyl is optionally substituted with one or more fluoro, or
(vii) —C$_{6-10}$ aryl; and

2)

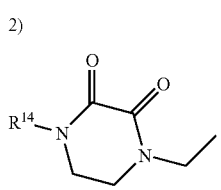

3)

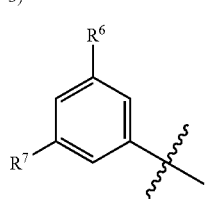

wherein R$^6$ is selected from the group consisting of
(a) (R$^8$—SO$_2$)N(R$^9$)—, wherein R$^8$ is selected from the group consisting of
(i) —C$_{1-10}$ alkyl,
(ii) —C$_{2-10}$ alkenyl,
(iii) —C$_{2-10}$ alkynyl,
(iv) —C$_{3-8}$ cycloalkyl, or
(v) —C$_{6-10}$ aryl
wherein said alkyl, alkenyl, alkynyl, cycloalkyl and aryl is optionally substituted with one or more
(A) halo,
(B) —OH,
(C) —CN,
(D) —O—C$_{1-10}$ alkyl,
(E) —C$_{1-10}$ alkyl,
(F) —C$_{2-10}$ alkenyl,
(G) —C$_{2-10}$ alkynyl,
(H) —C$_{3-8}$ cycloalkyl,
(I) —C$_{6-10}$ aryl, or
(J) heteroaryl,
and said aryl and heteroaryl is optionally substituted with one or more
(I) halo,
(II) —OH,
(III) —CN,
(IV) —O—C$_{1-10}$ alkyl,
(V) —C$_{3-8}$ cycloalkyl,
(VI) —C$_{1-10}$ alkyl,
(VII) —C$_{2-10}$ alkenyl, or
(VIII) —C$_{2-10}$ alkynyl;
R$^9$ is selected from the group consisting of
(i) hydrogen,
(ii) —C$_{1-10}$ alkyl,
(iii) —C$_{2-10}$ alkenyl,
(iv) —C$_{2-10}$ alkynyl, or
(v) —C$_{6-10}$ aryl,
wherein said alkyl, alkenyl, alkynyl or aryl is optionally substituted with one or more
(A) halo,
(B) —OH,
(C) —CN,
(D) —O—C$_{1-10}$ alkyl,
(E) —C$_{3-8}$ cycloalkyl,
(F) —C$_{6-10}$ aryl, or
(G) heteroaryl,
wherein said cycloalkyl, aryl or heteroaryl is optionally substituted with one or more
(I) halo,
(II) —OH.
(II) —CN,
(IV) —O—C$_{1-10}$ alkyl,
(V) —C$_{3-8}$ cycloalkyl, or
(VI) —C$_{6-10}$ aryl;

(b)

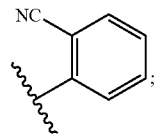

(c)

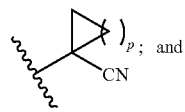

(d) hydrogen;
and $R^7$ is selected from the group consisting of

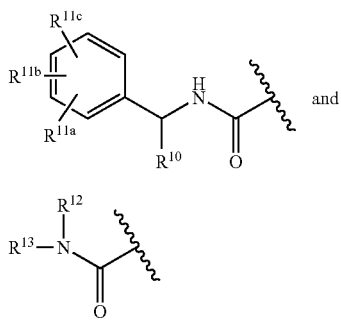

wherein $R^{10}$ is $C_{1-10}$ alkyl, wherein said alkyl is unsubstituted or substituted with one or more halogen;
$R^{11a}$, $R^{11b}$ and $R^{11c}$ are independently selected from the group consisting of:
(i) hydrogen,
(ii) halo,
(iii) —$C_{1-10}$ alkyl,
(iv) —OH,
(v) —CN,
(vi) $C_{3-12}$ cycloalkyl, and
(vii) —$C_{1-10}$ alkyl;
$R^{12}$ and $R^{13}$ are independently selected from the group consisting of
(i) hydrogen,
(ii) —$C_{1-10}$ alkyl,
(iii) —$C_{2-10}$ alkenyl,
(iv) —$C_{2-10}$ alkynyl, and
(v) —$C_{1-10}$ alkylene-$C_{3-12}$ cycloalkyl;
wherein said alkyl, alkenyl, alkynyl and cycloalkyl is optionally substituted with one or more
(A) halo,
(B) —OH,
(C) —CN,
(D) —$C_{1-10}$ alkyl,
(E) —O—$C_{1-10}$ alkyl,
(F) —$C_{3-8}$ cycloalkyl,
(G) —$NR^aR^b$, wherein $R^a$ and $R^b$ are selected from the group consisting of
 (i) hydrogen, and
 (ii) —$C_{1-10}$ alkyl, or $R^a$ and $R^b$ are joined together with the nitrogen atom to which they are attached to form a 4-6 membered carbocyclic ring having a single nitrogen, or
(H) —$C_{6-10}$ aryl;
or $R^{12}$ and $R^{13}$ are joined together with the nitrogen atom to which they are attached to form a 4-6 membered carbocyclic ring having a single nitrogen wherein said carbocyclic ring is optionally substituted with one or more
(1) —$C_{1-10}$ alkyl, wherein said alkyl is optionally substituted with one or more
 (i) halogen,
 (ii) hydroxy, or
 (iii) —$C_{1-6}$ alkoxy;
(2) —$C_{3-12}$ cycloalkyl,
(3) $(CH_2)_m$-phenyl, wherein said phenyl is unsubstituted or substituted with or more halogen,
(4) $C_{2-10}$ alkenyl,
(5) $C_{2-10}$ alkynyl,
(6) —CN, and said alkyl, alkenyl or alkynyl $R^{12}$ and $R^{13}$ groups are optionally substituted with one or more
(a) halo,
(b) —OH,
(c) —CN,
(d) —O—$C_{1-10}$ alkyl, or
(e) —$C_{3-12}$ cycloalkyl;
and said cycloalkyl and phenyl $R^{12}$ and $R^{13}$ groups are optionally substituted with one or more
(a) halo,
(b) —$C_{1-10}$ alkyl,
(c) OH,
(d) —CN,
(e) —$C_{3-12}$ cycloalkyl, or
(f) —O—$C_{1-10}$ alkyl;
$R^{14}$ is selected from the group consisting of
(i) hydrogen,
(ii) —$C_{1-10}$alkyl;
(iii) halo,
(iv) —$C_{3-12}$ cycloalkyl,
(v) —$C_{6-10}$ aryl, and
(vi) heteroaryl,
wherein said aryl and heteroaryl is optionally substituted with one or more
(A) halo,
—OH,
(C) —CN,
(D) —O—$C_{1-10}$ alkyl,
(E) —$C_{3-8}$ cycloalkyl, or
(F) —$C_{1-10}$ alkyl;

4)

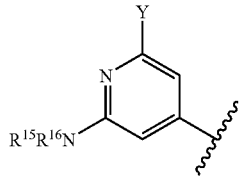

wherein Y is $R^6$ or halogen,
and $R^{15}$ and $R^{16}$ are independently selected from the group consisting of
(1) hydrogen,
(2) —$C_{1-10}$ alkyl,
(3) —$C_{2-10}$ alkenyl,
(4) —$C_{2-10}$ alkynyl, and
(5) —$C_{1-10}$ alkyl-$C_{3-12}$ cycloalkyl;
wherein said alkyl, cycloalkyl, alkenyl or alkynyl is unsubstituted or substituted with one or more
(a) halo,
(b) —OH,
(c) —CN,
(d) —$C_{1-10}$ alkyl
(e) —$C_{3-12}$ cycloalkyl,
(f) —O—$C_{1-10}$ alkyl,
(g) heteroaryl, wherein said heteroaryl may be unsubstituted or substituted with halogen;
(h) phenyl, or
(i) —$NR^cR^d$,
 (I) hydrogen, and
 (II) —$C_{1-10}$ alkyl, or $R^c$ and $R^d$ are joined together with the nitrogen atom to which they are attached to form a 4-6 membered carbocyclic ring having a single nitrogen, or $R^{15}$ and $R^{16}$ are joined together with the nitrogen atom to which they are attached to form a 4-6 membered carbocyclic ring having a single nitrogen, wherein said carbocyclic ring is unsubstituted or substituted with one or more
(a) —$C_{1-10}$ alkyl,
(b) —$C_{3-12}$ cycloalkyl,
(c) —$(CH_2)_n$-phenyl,
(d) —$C_{2-10}$ alkenyl, or
(e) —$C_{2-10}$ alkynyl,
wherein said alkyl, alkenyl and alkynyl is unsubstituted or substituted with one or more
(i) halo,
(ii) —OH,
(iii) —CN,
(iv) —O—$C_{1-10}$ alkyl, or
(v) —$C_{3-12}$ cycloalkyl;
and said cycloalkyl and phenyl is unsubstituted or substituted with one or more
(i) halo,
(ii) —$C_{1-10}$ alkyl,
(iii) —OH,
(iv) —CN,
(v) —$C_{3-12}$ cycloalkyl, or
(vi) —)—$C_{1-10}$ alkyl;
m is 0, 1, 2, 3 or 4;
n is 0 or 1; and
p is 1, 2, 3 or 4;
and pharmaceutically acceptable salts thereof, and individual enantiomers and diastereomers thereof.

The invention is also directed to methods of treating mammals for diseases in which the β-secretase enzyme is involved, such as Alzheimer's disease, by administering an effective amount of a compound of formula (I).

The invention is also directed to pharmaceutical compositions which include an effective amount of a compound of formula (I), or pharmaceutically acceptable salts thereof, and a pharmaceutically acceptable carrier.

The invention is also directed to a method for the manufacture of a medicament or a composition for inhibiting β-secretase enzyme activity in humans and animals and for treating Alzheimer's Disease, comprising combining a compound of formula (I) with a pharmaceutical carrier or diluent.

In one embodiment, the invention is directed to compounds of formula (I) wherein $R^1$ is selected from the group consisting of $C_{1-10}$ alkyl, wherein the alkyl is optionally substituted with one or more
(a) halo,
(b) —$C_{1-10}$ alkyl,
(c) —O—$C_{1-10}$ alkyl,
(d) —$C_{6-10}$ aryl, or
(e) heteroaryl,
and said aryl or heteroaryl is optionally substituted with one or more
(i) halo,
(ii) —OH,
(iii) —CN,
(iv) -$Q^1$-$C_{1-10}$ alkyl, wherein said alkyl is optionally substituted with one or more fluoro, or
(v) —$C_{1-10}$ alkyl, wherein said alkyl is optionally substituted with one or more fluoro,
and $Q^1$ is selected from the group consisting of
(A) —O—, or
(B) —$SO_2$—.

In another embodiment, the invention is directed to compounds of formula (I) wherein $R^2$ is hydrogen, and $R^3$ is $C_{1-10}$ alkyl or $C_{6-10}$ aryl, which are either unsubstituted or substituted.

In another embodiment, the invention is directed to compounds of formula (I) wherein $R^2$ and $R^3$ are each $C_{1-10}$ alkyl. Preferably, both $R^2$ and $R^3$ are methyl.

In another embodiment, the invention is directed to compounds of formula (I) wherein $R^2$ and $R^3$ are linked together to form a 3-7 carbocyclic ring structure, wherein one, two or three of the ring carbon atoms may be replaced with O, S, NH, —C(=O— or $SO_2$, and the carbocyclic ring is optionally substituted with $C_{1-10}$ alkyl. Exemplary $R^2/R^3$ 3-7 carbocyclic rings include:

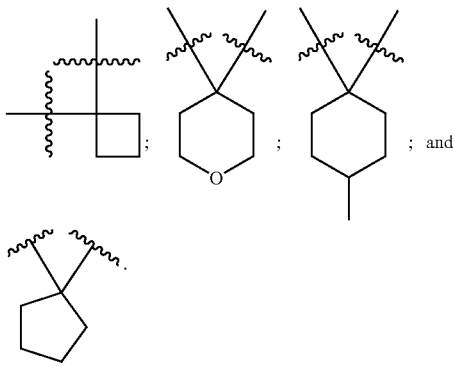

In another embodiment, the invention is directed to compounds of formula (I) wherein $R^4$ is selected from the group consisting of
(1) —$C_{1-10}$ alkyl,
(2) phenyl, or
(3) heteroaryl,
wherein said alkyl, phenyl or heteroaryl are optionally substituted with one or more
(i) halo,
(ii) —OH,
(iii) —CN,
(iv) -$Q^1$-$C_{1-10}$ alkyl,
(v) —$C_{1-10}$ alkyl, or
(vi) $C_{3-12}$ cycloalkyl.

Preferred heteroaryl groups for use in the invention include pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl.

Preferably, $R^4$ is phenyl, unsubstituted or substituted.

In one embodiment, X is

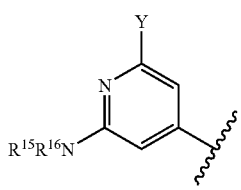

In this embodiment, $R^{15}$ is preferably —$C_{1-6}$ alkyl, which is optionally substituted with halogen or —O—$C_{1-6}$ alkyl, and $R^{16}$ is preferably —$C_{1-10}$ alkyl-$C_{3-12}$ cycloalkyl, wherein said alkyl and cycloalkyl are optionally substituted as defined above. For example, X may be

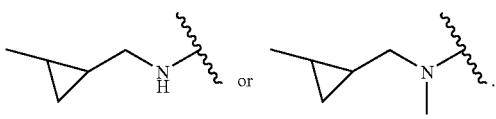

Within the genus of the compounds of formula (I), there is a sub-genus of compounds of formula (II)

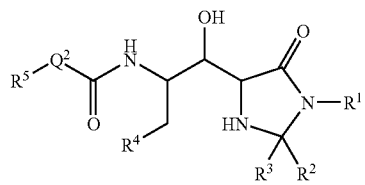

and pharmaceutically acceptable salts thereof, and individual enantiomers and diastereomers thereof, wherein X, $R^1$, $R^2$, $R^3$, $R^4$ and $R^5$ are as defined above.

In the sub-genus of compounds of formula (II), $Q^2$ is preferably —O— and $R^5$ is preferably $C_{1-10}$ alkyl, wherein said alkyl is optionally substituted with one or more
  (i) halo,
  (ii) —$C_{1-10}$ alkyl (preferably tert butyl), or
  (vii) —$C_{6-10}$ aryl (preferably phenyl).

In the sub-genus of compounds of formula (II), $R^1$ is preferably $C_{1-10}$ alkyl, wherein the alkyl is optionally substituted with one or more
  (a) halo,
  (b) —$C_{1-10}$ alkyl,
  (c) —O—$C_{1-10}$ alkyl,
  (d) —$C_{6-10}$ aryl, or
  (e) heteroaryl,
  and said aryl or heteroaryl is optionally substituted with one or more
    (i) halo,
    (ii) —OH,
    (iii) —CN,
    (iv) -$Q^1$-$C_{1-10}$ alkyl, wherein said alkyl is optionally substituted with one or more fluoro, or
    (v) $C_{1-10}$ alkyl, wherein said alkyl is optionally substituted with one or more fluoro,
    and $Q^1$ is selected from the group consisting of
      (A) —O—, or
      (B) —$SO_2$—.

In the sub-genus of compounds of formula (II), in one embodiment $R^2$ is hydrogen and $R^3$ is $C_{1-10}$ alkyl or $C_{6-10}$ aryl, which are either unsubstituted or substituted, or $R^2$ and $R^3$ are each $C_{1-10}$ alkyl.

In another embodiment of the sub-genus of compounds of formula (I), $R^2$ and $R^3$ are linked together to form a 3-7 carbocyclic ring structure, wherein one, two or three of the ring carbon atoms may be replaced with O, S, NH, —C(═O) or $SO_2$, and the carbocyclic ring is optionally substituted with $C_{1-10}$ alkyl.

In another embodiment of the sub-genus of compounds of formula (II), $R^4$ is selected from the group consisting of optionally substituted
  (1) —$C_{1-10}$ alkyl,
  (2) phenyl, and
  (3) heteroaryl.

Preferably, $R^4$ is phenyl, unsubstituted or substituted.

In another sub-genus of the compounds of formula (I), the invention is directed to compounds of formula (III):

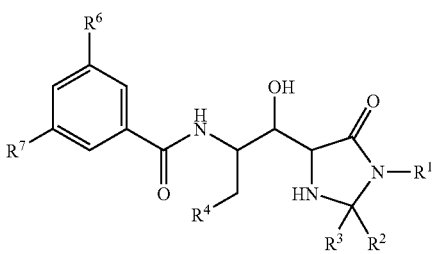

and pharmaceutically acceptable salts thereof, and individual enantiomers and diastereomers thereof, wherein X, $R^1$, $R^2$, $R^3$, $R^4$, $R^5$, $R^6$ and $R^7$ are as defined above.

In the sub-genus of compounds of formula (III), it is preferred that $R^6$ is ($R^8$—$SO_2$)N($R^9$)—.

In the sub-genus of compounds of formula (III), $R^1$ is preferably $C_{1-10}$ alkyl, wherein the alkyl is optionally substituted with one or more
  (a) halo,
  (b) —$C_{1-10}$ alkyl,
  (c) —O—$C_{1-10}$ alkyl,
  (d) —$C_{6-10}$ aryl, or
  (e) heteroaryl,
  and said aryl or heteroaryl is optionally substituted with one or more
    (i) halo,
    (ii) —OH,
    (iii) —CN,
    (iv) -$Q^1$-$C_{1-10}$ alkyl, wherein said alkyl is optionally substituted with one or more fluoro, or
    (v) —$C_{1-10}$ alkyl, wherein said alkyl is optionally substituted with one or more fluoro,
    and $Q^1$ is selected from the group consisting of
      (A) —O—, or
      (B) —$SO_2$—.

In the sub-genus of compounds of formula (III), in one embodiment $R^2$ is hydrogen and $R^3$ is $C_{1-10}$ alkyl or $C_{6-10}$ aryl, which are either unsubstituted or substituted, or $R^2$ and $R^3$ are each $C_{1-10}$ alkyl.

In another embodiment of the sub-genus of compounds of formula (I), $R^2$ and $R^3$ are linked together to form a 3-7 carbocyclic ring structure, wherein one, two or three of the ring carbon atoms may be replaced with O, S, NH, —C(═O) or $SO_2$, and the carbocyclic ring is optionally substituted with $C_{1-10}$ alkyl.

In another embodiment of the sub-genus of compounds of formula (III), $R^4$ is selected from the group consisting of optionally substituted
  (1) —$C_{1-10}$ alkyl,
  (2) phenyl, and
  (3) heteroaryl.

Preferably, $R^4$ is phenyl, unsubstituted or substituted.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkylene," by itself or as part of another substituent, means a saturated straight or branched chain divalent hydrocarbon radical having the number of carbon atoms designated. The term $C_0$ alkylene (for example, in the radical "—$C_0$alkylene-$C_{6-10}$ aryl) means that the alkylene group is absent.

As used herein, the term "alkoxy," by itself or as part of another substituent, means the group —O-alkyl, wherein alkyl is defined above, having the number of carbon atoms designated (e.g., $C_{1-10}$ alkoxy means an alkoxy group having from one to ten carbon atoms). Preferred alkoxy groups for use in the invention are $C_{1-6}$ alkoxy groups, having from one to six carbon atoms. Exemplary preferred alkoxy groups include methoxy, ethoxy, propoxy, butoxy, sec-butoxy and pentoxy. Especially preferred alkoxy groups are $C_{1-3}$ alkoxy.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as spiro fused ring systems.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "carbocyclic," by itself or as part of another substituent, means a cycloalkyl group as defined above, or a non-aromatic heterocyclic group. A non-aromatic heterocyclic group, by itself or as part of another substituent, means a cycloalkyl group as defined above in which one or more of the ring carbon atoms is replaced with a heteroatom (such as N, S or O). Suitable non-aromatic heterocyclic groups for use in the invention include piperidinyl, piperazinyl, morpholinyl, tetrahydrofuranyl, tetrahydrothienyl, pyrrolidinyl, pyrazolidinyl, azetidinyl, tetrahydropyranyl and imidazolidinyl. Preferred non-aromatic heterocyclic groups are piperidinyl, piperazinyl, tetrahydrofuranyl, tetrahydropyranyl, pyrrolidinyl, morpholinyl and azetidinyl.

When a non-aromatic heterocyclic group as defined herein is substituted, the substituent may be bonded to a ring carbon atom of the heterocyclic group, or on a ring heteroatom (i.e., a nitrogen, oxygen or sulfur), which has a valence which permits substitution. Preferably, the substituent is bonded to a ring carbon atom. Similarly, when a non-aromatic heterocyclic group is described as a substituent, the point of attachment may be at ring carbon atom of the heterocyclic group, or at a ring heteroatom (i.e., a nitrogen, oxygen or sulfur), which has a valence which permits attachment. Preferably, the point of attachment is a ring carbon atom.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems as well as single ring systems. Preferred aryl groups for use in the invention are phenyl and naphthyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Preferred heteroaryl groups have from 5 to 12 ring atoms. Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, benzimidazolyl, quinolinyl, isoquinolinyl, tetrazolyl, indazolyl, napthyridinyl, triazolyl, oxazolyl, oxadiazolyl, thiazolyl, thiadiazolyl, isoxazolyl, tetrahydroquinolinyl, tetrahydroisoquinolinyl and dihydroindolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

Compounds described herein may contain one or more double bonds, and may thus give rise to cis/trans isomers as well as other conformational isomers. The present invention includes all such possible isomers as well as mixtures of such isomers.

Formulas (I) to (III) are shown above without a definite stereochemistry at certain positions. The present invention includes all stereoisomers of Formulas (I) to (III) and pharmaceutically acceptable salts thereof. Three of the carbon atoms of compounds of formula (I) are chiral. The compounds are described herein to include racemates, as well as sterochemically pure diastereomers. As a result, the compounds of formula (I) may be present as racemates or as one of the following eight diastereomers (IA) to (IH):

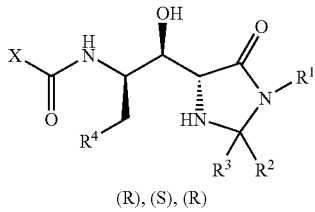
(IA)
(R), (S), (R)

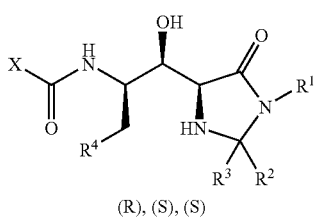
(IB)
(R), (S), (S)

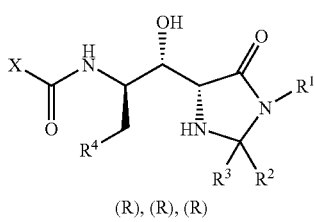
(IC)
(R), (R), (R)

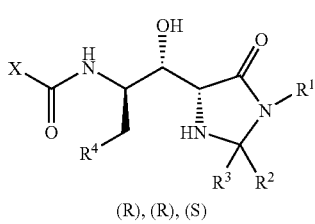
(ID)
(R), (R), (S)

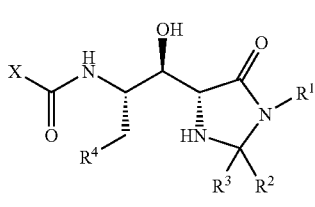
(IE)
(S), (S), (R)

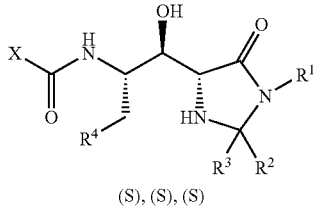
(IF)
(S), (S), (S)

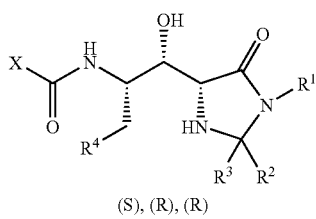
(IG)
(S), (R), (R)

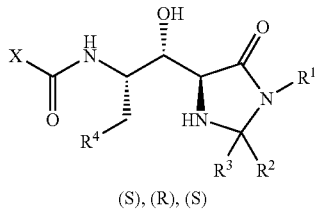
(IH)
(S), (R), (S)

The (S), (R), (S) diastereomer is preferred. The stereochemical descriptors (R or S) were assigned according to the Cahn-Ingold-Prelog system (*Angew. Chem. Int. Ed. Engl.* 1982, 21, 567) following the path of the higher priority atom (e.g. —NC=O higher than —NHCR$_2$R$_3$).

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds claimed in this invention can be prepared according to the following general procedure methods.

Scheme 1

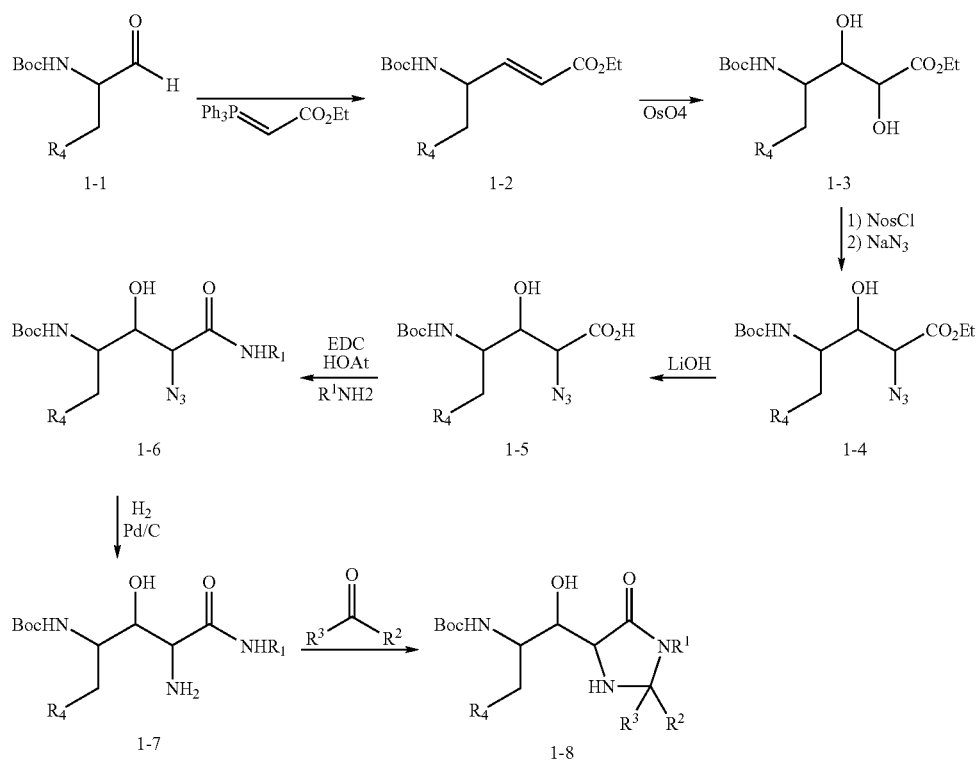

In Scheme 1, amino-acid derived aldehydes 1-1 undergo a Wittig reaction to give olefin 1-2, which can be dehydroxylated with osmium tetroxide in the presence of chiral ligands to give either enantiomer of 1-3. Selective nosylation followed by azide displacement gives 1-4, which can be hydrolyzed to acid 1-5. Coupling this acid to a variety of amines gives amide 1-6, which is reduced and cyclized to compounds of the invention 1-8.

Scheme 2

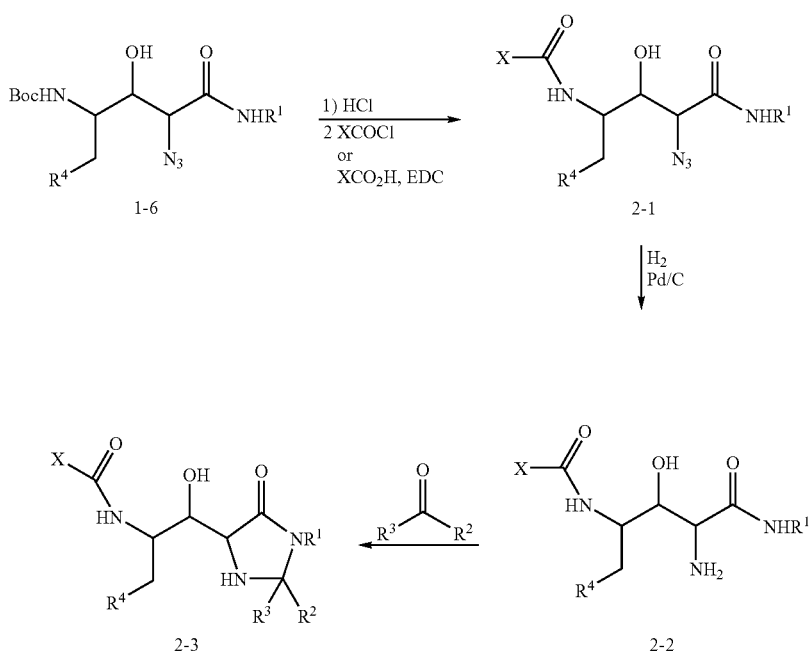

Another method is illustrated in Scheme 2 whereby the carbamate of intermediate 1-6 from Scheme 1 can be removed and replaced with other acyl groups 2-1. Hydrogenation and cyclization give compounds 2-3.

The term "substantially pure" means that the isolated material is at least 90% pure, and preferably 95% pure, and even more preferably 99% pure as assayed by analytical techniques known in the art.

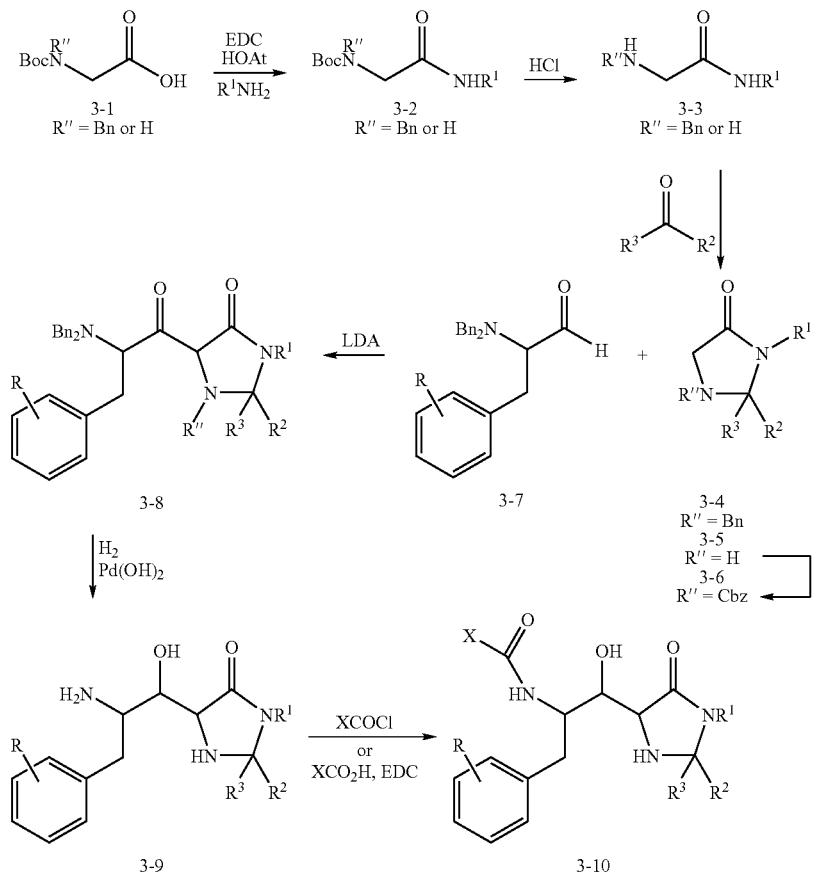

Alternately, the imidazolidinone ring can be formed first as shown in Scheme 3. Appropriately configured glycine amides 3-3 undergo cyclization with aldehydes or ketones to give 3-4 or 3-5 depending on the group at R". The free NH of 3-5 is then protected as its Cbz carbamate and reacted with LDA followed by aldehyde 3-7 to give adduct 3-8. Removal of benzyl and Cbz groups gives amine 3-9 which can be coupled with a variety of acyl groups to give compounds of the invention 3-10.

Additional compounds of the invention may be made by those skilled in the art with reference to the schemes and intermediates disclosed in commonly owned, co-pending International patent applications WO 2005/065195, published Jul. 21, 2005 (see, e.g., schemes 3-7); WO 2005/051914, published Jun. 9, 2005 (see, e.g., schemes 4, 4A, 5, 6 and 8-10); WO 2005/103043, published Nov. 3, 2005 (see, e.g., scheme 7); and WO 2005/103020, published Nov. 3, 2005 (see, e.g., schemes 7-13); and in commonly owned, co-pending U.S. provisional application Ser. No. 60/644,925, filed Jan. 19, 2005 (see, e.g., schemes 2.1, 2.2).

Specific embodiments of the compounds of the invention, and methods of making them, are described in Examples 1-49 herein.

The term "pharmaceutically acceptable salts" refers to salts prepared from pharmaceutically acceptable non-toxic bases or acids including inorganic or organic bases and inorganic or organic acids.

The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2 dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds of the present invention disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; glycine transport inhibitors, tau phosphorylation inhibitors; blockers of Aβ oligomer formation; p25/CDK5 inhibitors; HMG-CoA reductase inhibitors; PPAR gamma agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; NR2B antagonists; androgen receptor modulators; acetylcholinesterase inhibitors such as galantamine, rivastigmine, donepezil, and tacrine; mGluR5 modulators; growth hormone secretagogues such as ibutamoren, ibutamoren mesylate, and capromorelin; histamine $H_3$ antagonists; AMPA agonists; PDE IV inhibitors; $GABA_A$ inverse agonists; $GABA_A$ α5 receptor ligands; $GABA_B$ receptor ligands; potassium channel blockers; neuronal nicotinic agonists; P450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of the present invention, is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, DM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomotology of the diseased (i.e., arresting further development of the pathology and/or symptomotology), or (2) ameliorating the disease in an animal that is experiencing or displaying the pathology or symptomotology of the diseased (i.e., reversing the pathology and/or symptomotology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 µM and can not be determined due to the limit of solubility of the substrate. A typical reaction contains approximately 0.1 nM enzyme, 0.25 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction proceeds for 30 min and is then stopped by the addition of 25 µl of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 µM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

HPLC assay: A homogeneous end point HPLC assay is used with the substrate (coumarin-CO-REVNFEVEFR), which is cleaved by BACE 1 to release the N-terminal fragment attached with coumarin. The Km of the substrate is greater than 100 µM and can not be determined due to the limit of solubility of the substrate. A typical reaction contains approximately 2 nM enzyme, 1.0 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the reaction is stopped by the addition of 25 µL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared, and the concentration rage is dependent on the potency predicted by ECL. Solutions of inhibitor in DMSO are included in the reaction mixture (final DMSO concentration is 10%). All experiments are conducted at rt using the standard reaction conditions described above. To determine the $IC_{50}$ of the compound, four parameters equation is used for curve fitting. The errors in reproducing the dissociation constants are typically less than two-fold.

In particular, the compounds of the following examples had activity in inhibiting the beta-secretase enzyme in the aforementioned ECL assay, generally with an $IC_{50}$ from about 1 nM to 100 µM. Such a result is indicative of the intrinsic activity of the compounds in use as inhibitors of beta-secretase enzyme activity.

Several methods for preparing the compounds of this invention are illustrated in the schemes and examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Me: methyl
Et: ethyl
t-Bu: tert-butyl
Ar: aryl
Ph: phenyl
Bn: benzyl
Ac: acetyl
EDC: 1-Ethyl-3-(3-dimethylaminopropyl)-carbodiimide
BOP: benzotriazol-1-yl-oxy-tris-(dimethylamino)phosphonium hexa-fluorophosphate
HOAT: 1-hydroxy-7-azabenzotriazole
THF: tetrahydrofuran
DMSO: dimethylsulfoxide
EDTA: ethylene diamine tetraacetic acid
Boc: tert-butyloxy carbonyl
CHAPS: 3-[(3-cholamidopropyl)dimethylammonio]-2-hydroxy-1-propanesulfonate
BSA: bovine serum albumin
TFA: trifluoracetic acid
DMF: N,N-dimethylformamide
rt: room temperature
HPLC: high performance liquid chromatography HRMS: high resolution mass spectrometry
LDA: lithium diisopropyamide
EDC: 1-ethyl-3-(3-dimethylaminopropyl)carbodiimide
CBz: benzyloxy carbonyl

EXAMPLE 1 tert-Butyl (1S,2R)-1-benzyl-2-hydroxy-2-[(4S-2 -isopropyl-1-(1-methylbutyl)-5-oxoimidazolidin-4-yl] ethylcarbamate

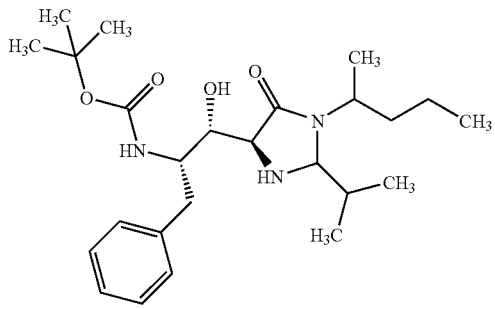

Step 1:

Ethyl (2E,4S)-4-[(tert-butoxycarbonyl)amino]-5-phenylpent-2-enoate

A solution of (S)-(−)-2-(tert-butoxycarbonylamino)-3-phenylpropanal (6.87 g, 27.56 mmol) and (carbethoxymethylene)triphenylphosphine (9.60 g, 27.56 mmol) in toluene (150 mL) was stirred and heated to 80° C. for 70 min. The product was isolated by flash column chromatography on silica gel using a gradient elution of 5-25% EtOAc/hexanes. Collection and concentration of the appropriate fractions yielded the compound as a white solid. $^1$H NMR (400 MHz, CDCl$_3$) δ 7.33-7.22 (m, 3H), 7.19-7.17 (m, 2H), 6.92 (dd, J=4.8, 15.6 Hz, 1H), 5.86 (dd, J=1.6, 15.6 Hz, 1H), 4.62 (br s, 1H), 4.52 (br s, 1H), 4.19 (q, J=7.2, 14.0 Hz, 2H), 2.95-2.90 (m, 2H), 1.40 (s, 9H), 1.30-1.25 (m, 3H); ES MS [M-100 (loss of BOC)+1]=220.

Step 2:

Ethyl (2R,3S,4S)-4-[(tert-butoxycarbonyl)amino]-2,3 -dihydroxy-5-phenylpentanoate To a mixture of methanesulfonamide (3.27 g, 34.41 mmol), potassium ferricyanide (III) (33.99 g, 103.23 mmol), potassium osmate (IV) dihydrate (127 mg, 0.34 mmol), and potassium carbonate (14.27 g, 103.23 mmol) in tert-butanol (150 mL) and water (75 mL) was added a sonicated solution of hydroquinine 2,5-diphenyl-4,6-pyrimidinediyl diether (606 mg, 0.69 mmol) in water (75 mL). The mixture was treated with solid ethyl (2E,4S)-4-[(tert-butoxycarbonyl)amino]-5-phenylpent-2-enoate (11.00 g, 34.41 mmol) and stirred at rt overnight. The reaction was cooled to 0° C. and treated with sodium sulfite (50 g). Following stirring for 30 min at 0° C. and 1.5 h at rt, the mixture was extracted with EtOAc (3×200 mL). The combined organic layers were washed with brine (200 mL), dried over Na$_2$SO$_4$, filtered, and concentrated in vacuo to afford the product as a yellow solid. $^1$H NMR (400 MHz, CDCl$_3$) δ 7.32-7.23 (m, 5H), 4.81 (d, J=9.2 Hz, 1H), 4.35 (s, 1H), 4.31-4.24 (m, 2H), 4.02-3.94 (m, 2H), 3.79 (br s, 1H), 3.09-3.04 (m, 1H), 2.95-2.90 (m, 1), 2.66 (br s, 1H), 1.37 (s, 9H), 1.32-1.21 (m, 3H); ES MS (2M+23)=729.

Step 3:

Ethyl (2R,3S,4S)-4-[(tert-butoxycarbonyl)amino]-2-O-[(4-nitrophenyl)sulfonyl]-3-hydroxy-5-phenylpentanoate A solution of Ethyl (2R,3S,4)-4-[(tert-butoxycarbonyl)amino]-2,3-dihydroxy-5-phenylpentanoate (6.69 g, 18.94 mmol) in CH$_2$Cl$_2$ (300 mL) was treated with triethylamine (3.43 mL, 24.62 mmol) and 4-nitrobenzenesulfonyl chloride (4.62 g, 20.84 mmol) and stirred at rt overnight. The reaction mixture was diluted with CH$_2$Cl$_2$ (200 mL) and washed with aqueous 1N HCl solution (150 mL) and brine (150 mL). The organic extract was dried over Na$_2$SO$_4$, filtered, and concentrated in vacuo. The resulting residue was purified three times by flash column chromatography on silica gel using gradient elutions of 10-50% EtOAc/hexanes, 20-50% EtOAc/hexanes, and 0-30% EtOAc/hexanes. Collection and concentration of the appropriate fractions yielded the compound as a yellow solid. $^1$H NMR (400 MHz, CDCl$_3$) δ 8.30 (dd, J=2.4, 9.2 Hz, 2H), 8.20 (d, J=8.4 Hz, 2H), 7.33-7.19 (m, 5H), 5.28 (s, 1H), 4.67 (d, J=8.0 Hz, 2H), 4.21-4.09 (m, 3H), 3.92-3.85 (m, 1H), 3.00 (d, J=6.0 Hz, 2H), 1.38 (s, 9H), 1.28-1.21 (m, 3H); ES MS (M+23)=561.

Step 4:

Ethyl (2S,3S,4S)-2-azido-[(tert-butoxycarbonyl) amino]-3 -hydroxy-5-phenylpentanoate A suspension of sodium azide (2.33 g, 35.89 mmol) in DMF (50 mL) was heated to 50° C. for 20 min. The mixture was treated with a solution of Ethyl (2R,3S,4S)-4-[(tert-butoxycarbonyl)amino]-2-O-[(4-nitrophenyl)sulfonyl]-3-hydroxy-5-phenylpentanoate (1.93 g, 3.59 mmol) in DMF (5 mL) and was stirred and heated to 50° C. overnight. The reaction was diluted with EtOAc (80 mL) and washed with water (40 mL) and brine (40 mL). The organic extract was dried over Na$_2$SO$_4$, filtered, and concentrated in vacuo. The resulting residue was purified twice by flash column chromatography on silica gel using a gradient elution of 0-60% EtOAc/hexanes each time. Collection and concentration of the appropriate fractions yielded the compound as a yellow residue. $^1$H NMR (400 MHz, CD$_3$OD) δ 7.32-7.27 (m, 2H), 7.24-7.21 (m, 3H), 4.71 (d, J=7.2 Hz, 1H), 4.29 (q, J=7.2, 14.4 Hz, 2H), 4.08-3.94 (m, 4H), 2.99 (dd, J=4.0, 14.0 Hz, 1H), 2.90-2.85 (m, 1H), 1.51-1.31 (m, 12H); ES MS (M+23)=401.

Step 5:

(2S,3S,4S)-2-azido-4-[(tert-butoxycarbonyl) amino]-3 -hydroxy-5-phenylpentanoic acid To a solution of Ethyl (2S,3S,4S)-2-azido-4-[(tert-butoxycarbonyl)amino]-3-hydroxy-5-phenylpentanoate (22 mg, 0.058 mmol) in 50% MeOH/THF (800 μL) was added aqueous 1N LiOH (70 μL, 0.070 mmol). The reaction was stirred at rt overnight and concentrated in vacuo. The resulting residue was suspended in EtOAc (30 mL) and washed with aqueous 10% KHSO$_4$ solution (15 ml) and brine (15 mL), and the organic extract was dried over Na$_2$SO$_4$, filtered, and concentrated in vacuo. Purification of the residue by flash column chromatography on silica gel using an isocratic elution of 10% (10% AcOH/MeOH)/CH$_2$Cl$_2$ and collection and concentration of the appropriate fractions yielded the compound as a yellow residue. $^1$H NMR (400 MHz, CD$_3$OD) δ 7.23-7.15 (m, 5H), 4.23-3.87 (m, 3H), 3.21-3.08 (m, 1H), 2.66-2.57 (m, 1H), 1.29 (s, 9H); ES MS (M+23)=373.

Step 6:

(2S,3S,4S)-2-azido-4-[(tert-butoxycarbonyl)amino]-3-hydroxy-N-(1-methylbutyl)-5-phenylpentanamide amide A solution of (2S,3S,4S)-2-azido-4-[(tert-butoxycarbonyl)amino]-3-hydroxy-5-phenylpentanoic acid (54 mg, 0.154 mmol), 2-amylamine (18 μL, 0.154 mmol), triethylamine (26 μL, 0.185 mmol), HOAT (25 mg, 0.185 mmol), and EDC (41 mg, 0.216 mmol) in DMF (1 mL) was stirred at rt overnight. The solution was diluted with EtOAc (30 mL) and washed with saturated NaHCO$_3$ solution (30 mL), and brine (30 mL). The organic extract was dried over Na$_2$SO$_4$, filtered, and concentrated in vacuo. The resulting residue was suspended in DMF, filtered, and purified by reverse phase chromatography on a C-18 column using a gradient elution of 95-5% H$_2$O (0.1% TFA)/CH$_3$CN (0.1% TFA). Collection and concentration of the appropriate fractions afforded the product which was again dissolved in EtOAc (60 mL) and washed with saturated NaHCO$_3$ solution (30 mL) and brine (30 mL). The organic extract was dried over Na$_2$SO$_4$, filtered, and concentrated in vacuo to afford the product as a white solid. $^1$H NMR (400 MHz, CD$_3$OD) δ 7.25-7.15 (m, 5H), 3.95-3.93 (m, 3H), 3.81-3.78 (m, 1H), 3.08-3.04 (m, 1H), 2.67-2.61 (m, 1H), 1.49-1.37 (m, 4H), 1.30-1.20 (m, 9H), 1.18-1.15 (m, 3H), 0.96-0.92 (m, 3H); ES MS (M+1)=420.

Step 7:

(2S,3R,4S)-2-amino-4-[(tert-butoxycarbonyl)amino]-3-hydroxy-N-(1-methylbutyl)-5-phenylpentanamide To a solution of (2S,3S,4S)-2-azido-4-[(tert-butoxycarbonyl)amino]-3-hydroxy-N-(1-methylbutyl)-5-phenylpentanamide (55 mg, 0.131 mmol) in MeOH (4 mL) which had been degassed and purged with nitrogen was added a small amount of 10% Pd on carbon. The mixture was flushed again with nitrogen and stirred overnight under a balloon atmosphere of hydrogen. The reaction was filtered and the resulting filtrate concentrated in vacuo to afford the product as a yellow solid. $^1$H NMR (400 MHz, CD$_3$OD) δ 7.25-7.23 (m, 4H), 7.17-7.15 (m, 1H), 3.91-3.86 (m, 2H), 3.66-3.59 (m, 1H), 3.32-3.30 (m, 1H), 3.21-3.17 (m, 1H), 2.59-2.52 (m, 1H), 1.52-1.33 (m, 4H), 1.29 (s, 9H), 1.26-1.12 (m, 3H), 0.95-0.91 (m, 3H); ES MS (M+1)=394.

Step 8:

tert-Butyl (1S,2S)-1-benzyl-2-hydroxy-2-[(4S)-2-isopropyl-1-(1-methylbutyl)-5-oxoimidazolidin-4-yl]ethylcarbamate To a solution of (2S,3R,4S)-2-amino-4-[(tert-butoxycarbonyl)amino]-3-hydroxy-N-(1-methylbutyl)-5-phenylpentanamide (46 mg, 0.117 mmol) in MeOH (500 mL) was added isobutylaldehyde (100 mL), a small amount of p-toluene sulfonic acid, and Na$_2$SO$_4$ (10 mg). The mixture was capped and heated to 65° C. overnight. The reaction was filtered and the resulting filtrate purified by reverse phase chromatography on a C-18 column using a gradient elution of 95-5% H$_2$O (0.1% TFA)/CH$_3$CN (0.1% TFA). Collection and concentration of the appropriate fractions separately afforded the earlier and later eluting diastereomer products as the trifluoroacetate salts. Earlier eluting diastereomer: $^1$H NMR (400 MHz, CD$_3$OD) δ 7.29-7.25 (m, 4H), 7.19-7.18 (m, 1H), 4.23 (br s, 1H), 4.05-3.88 (m, 2H), 3.75-3.63 (m, 1H), 3.15-3.05 (m, 1H), 2.80-2.74 (m, 1H), 2.33-2.27 (m, 1H), 1.98-1.89 (m, 1H), 1.76-1.70 (m, 1H), 1.60-1.51 (m, 1H), 1.48-1.24 (m, 11H), 1.22-1.20 (m, 2H), 1.13-1.08 (m, 4H), 0.99-0.87 (m, 6H); HRMS (FT-ICR) C$_{25}$H$_{41}$N$_3$O$_4$+H=448.3195; calculated 448.3170; Later eluting diastereomer: $^1$H NMR (400 MHz, CD$_3$OD) δ 7.28-7.25 (m, 4H), 7.19-7.18 (m, 1H), 4.26-4.24 (m, 1H), 4.08-3.99 (m, 2H), 3.77-3.70 (m, 1H), 3.10-3.07 (m, 1H), 2.83-2.77 (m, 1H), 2.38-2.37 (m, 1H), 1.85-1.77 (m, 2H), 1.62-1.56 (m, 1H), 1.42-1.27 (m, 11H), 1.24 (m, 3H), 1.11 (t, J=5.6 Hz, 3H), 1.02 (d, J=6.8 Hz, 3H), 0.99-0.93 (m, 3H); HRMS (FT-ICR) C$_{25}$H$_{41}$N$_3$O$_4$+H=448.3168; calculated 448.3170.

EXAMPLE 2 tert-Butyl (1S,2R)-1-benzyl-2-hydroxy-2-[(4S)-1-isopentyl-2-isopropyl-5-oxoimidazolidin-4-yl]ethylcarbamate

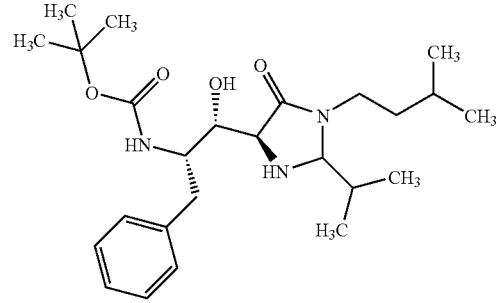

Step 1:

tert-Butyl (1S,2R)-1-benzyl-2-hydroxy-2-[(4S)-1-isopentyl-2-isopropyl-5-oxoimidazolidin-4-yl]ethylcarbamate The title compound was prepared using a sequence of procedures similar to that described in Example 1, except that isopentylamine was used in placed of 2-amylamine in Step 6. Final purification separately afforded the earlier and later eluting diastereomers as the trifluoroacetate salts. Earlier eluting diastereomer: HRMS (FT-ICR) C$_{25}$H$_{41}$N$_3$O$_4$+H=448.3170; calculated 448.3170; Later eluting diastereomer: HRMS (FT-ICR) C$_{25}$H$_{41}$N$_3$O$_4$+H=448.3179; calculated 448.3170.

EXAMPLE 3 tert-Butyl (1S,2R)-1-benzyl-2-hydroxy-2-{(4S)-2-isopropyl-5-oxo-1-[3-(trifluoromethyl)benzyl]imidazolidin-4-yl}ethylcarbamate

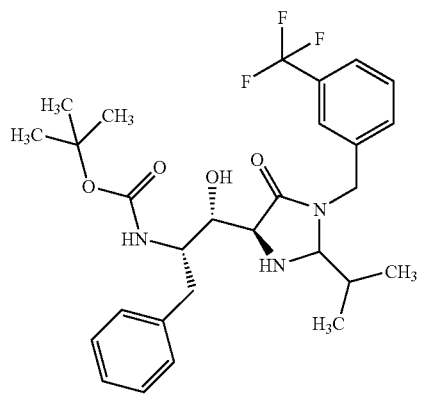

Step 1:

tert-Butyl (1S,2R)-1-benzyl-2-hydroxy-2-{(4S)-2-isopropyl-5-oxo-1-[3-(trifluoromethyl)benzyl]imidazolidin-4-yl}ethylcarbamate The title compound was prepared using a sequence of procedures similar to that described in Example 1, except that 3-(trifluoromethyl)benzylamine was used in placed of 2-amylamine in Step 6, and MeOH/EtOAc was used in place of MeOH in Step 7. Final purification separately afforded the earlier and later eluting diastereomers as the trifluoroacetate salts. Earlier eluting diastereomer: HRMS (FT-ICR) $C_{28}H_{36}N_3O_4$+H=536.2732; calculated 536.2731; Later eluting diastereomer: HRMS (FT-ICR) $C_{28}H_{36}N_3O_4$+H=536.2775; calculated 536.2731.

EXAMPLE 4 tert-Butyl (1S,2R)-1-benzyl-2-hydroxy-2-[(4S-2-isopropyl-5-oxo-1-(2-phenylethyl)imidazolidin-4-yl]ethylcarbamate

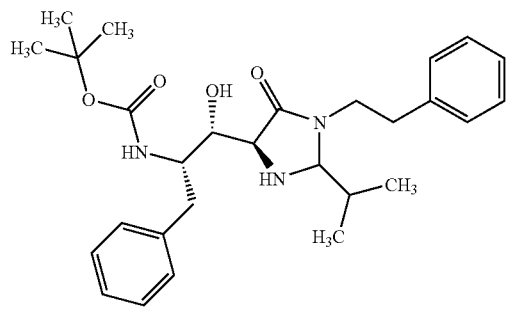

Step 1:

tert-Butyl (1S,2R)-1-benzyl-2-hydroxy-2-[(4S)-2-isopropyl-5-oxo-1-(2-phenylethyl)imidazolidin-4-yl]ethylcarbamate The title compound was prepared using a sequence of procedures similar to that described in Example 1, except that phenethylamine was used in placed of 2-amylamine in Step 6, and MeOH/EtOAc was used in place of MeOH in Step 7. Final purification separately afforded the earlier and later eluting diastereomers as the trifluoroacetate salts. Earlier eluting diastereomer: HRMS (FT-ICR) $C_{28}H_{39}N_3O_4$+H=482.2976; calculated 482.3013; Later eluting diastereomer: HRMS (FT-ICR) $C_{28}H_{39}N_3O_4$+H=482.3022; calculated 482.3013.

EXAMPLE 5 tert-Butyl {(1S,2R)-1-benzyl-2-hydroxy-2-[(4S)-2-isopropyl-5-oxo-1-pentylimidazolidin-4-yl]ethyl}carbamate

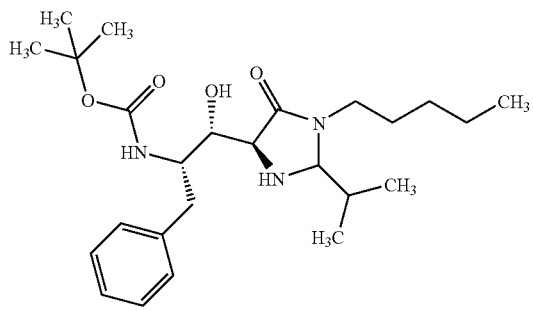

Step 1:

tert-Butyl {(1S,2R)-1-benzyl-2-hydroxy-2-[(4S)-2-isopropyl-5-oxo-1-pentylimidazolidin-4-yl]ethyl}carbamate The title compound was prepared using a sequence of procedures similar to that described in Example 1, except that amylamine was used in placed of 2-amylamine in Step 6, and MeOH/EtOAc was used in place of MeOH in Step 7. Final purification separately afforded the earlier and later eluting diastereomers as the trifluoroacetate salts. Earlier eluting diastereomer: ES MS (M+1)=448; Later eluting diastereomer: ES MS (M+1)=448.

EXAMPLE 6

[(1S,2R)-2-Hydroxy-2-[(4S)-1-[2-(1-methylethoxy)ethyl]-2-(1-methylethyl)-5-oxo-4-imidazolidinyl]-1-(phenylmethyl)ethyl]-, 1,1-dimethylethyl ester carbamic acid

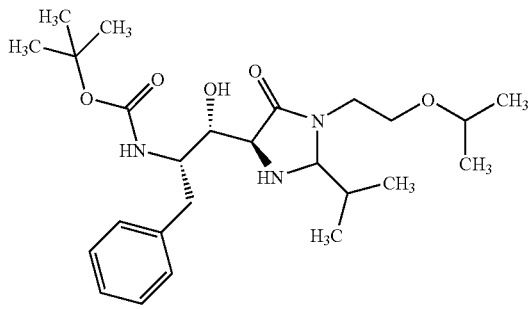

Step 1:

[(1S,2R)-2-Hydroxy-2-[(4S)-1-[2-(1-methylethoxy)ethyl]-2-(1-methylethyl)-5-oxo-4-imidazolidinyl]-1-(phenylmethyl)ethyl]-, 1,1-dimethylethyl ester carbamic acid The title compound was prepared using a sequence of procedures similar to that described in Example 1, except that 2-aminoethylisopropyl ether was used in place of 2-amylamine in Step 6, and MeOH/EtOAc was used in place of MeOH in Step 7. Final purification cleanly afforded one diastereomer as the trifluoroacetate salt. ES MS (M+1)=464.

EXAMPLE 7 tert-Butyl {(1S,2R)-1-benzyl-2-hydroxy-2-[(4S)-2-isopropyl-1-(2-methoxyethyl)-5-oxoimidazolidin-4-yl]ethyl}carbamate

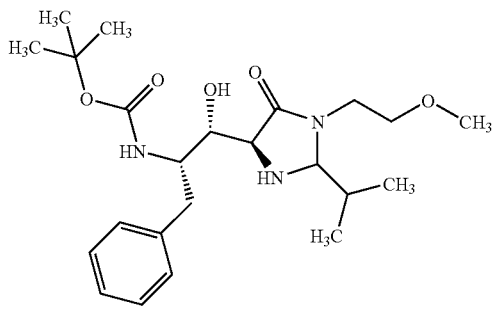

Step 1:

tert-Butyl {(1S,2R)-1-benzyl-2-hydroxy-2-[(4S)-2-isopropyl-1-(2-methoxyethyl)-5-oxoimidazolidin-4-yl]ethyl}carbamate The title compound was prepared using a sequence of procedures similar to that described in Example 1, except that 2-methoxyethylamine was used in placed of 2-amylamine in Step 6, and MeOH/EtOAc was used in place of MeOH in Step 7. Final purification cleanly afforded one diastereomer as the trifluoroacetate salt. ES MS (M+1)=436.

EXAMPLE 8 tert-Butyl ((1S,2R)-1-benzyl-2-hydroxy-2-{(4S)-2-isopropyl-5-oxo-1-[2-(trifluoromethyl)benzyl]imidazolidin-4-yl}ethyl)carbamate

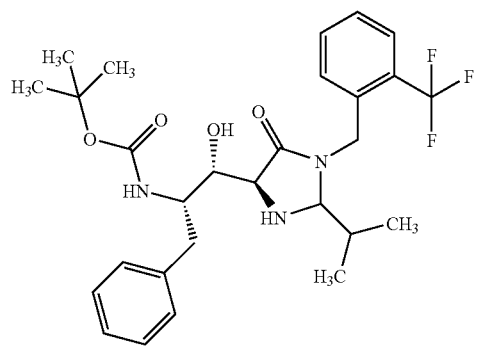

Step 1:

tert-Butyl ((1S,2R)-1-benzyl-2-hydroxy-2-{(4S)-2-isopropyl-5-oxo-1-[2-(trifluoromethyl)benzyl]imidazolidin-4-yl}ethyl)carbamate The title compound was prepared using a sequence of procedures similar to that described in Example 1, except that 2-trifluoromethyl)benzylamine was used in placed of 2-amylamine in Step 6, and MeOH/EtOAc was used in place of MeOH in Step 7. Final purification separately afforded the earlier and later eluting diastereomers as the trifluoroacetate salts. Earlier eluting diastereomer: ES MS (M+1)=536; Later eluting diastereomer: ES MS (M+1)=536.

EXAMPLE 9 tert-Butyl ((1S,2R)-1-benzyl-2-hydroxy-2-{(4S)-2-isopropyl-5-oxo-1-[(1S)-1-phenylethyl]imidazolidin-4-yl}ethyl)carbamate

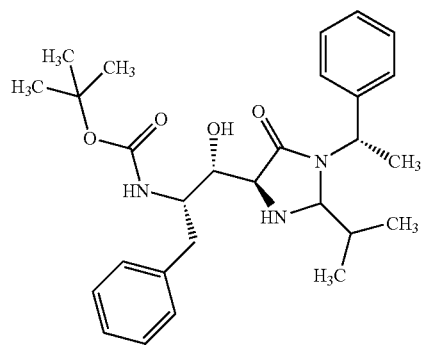

Step 1:

tert-Butyl ((1S,2R)-1-benzyl-2-hydroxy-2-{(4S)-2-isopropyl-5-oxo-1-[(1S)-1-phenylethyl]imidazolidin-4-yl}ethyl)carbamate The title compound was prepared using a sequence of procedures similar to that described in Example 1, except that (S)-(−)-α-methylbenzylamine was used in placed of 2-amylamine in Step 6, and MeOH/EtOAc was used in place of MeOH in Step 7. Final purification cleanly afforded one diastereomer as the trifluoroacetate salt. ES MS (M+1)=482.

EXAMPLE 10 tert-Butyl {(1S,2R)-1-benzyl-2-hydroxy-2-[(4S)-2-isopropyl-5-oxo-1-(pyridin-2-ylmethyl)imidazolidin-4-yl]ethyl}carbamate

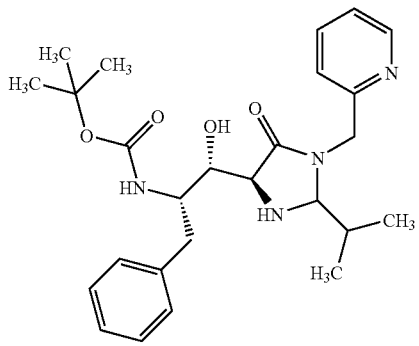

Step 1:

tert-Butyl {(1S,2R)-1-benzyl-2-hydroxy-2-[(4S)-2-isopropyl-5-oxo-1-(pyridin-2-ylmethyl)imidazolidin-4-yl]ethyl}carbamate The title compound was prepared using a sequence of procedures similar to that described in Example 1, except that 2-aminomethyl)pyridine was used in placed of 2-amylamine in Step 6, and MeOH/EtOAc was used in place of MeOH in Step 7. Final purification cleanly afforded one diastereomer as the trifluoroacetate salt. ES MS (M+1)=469.

EXAMPLE 11 tert-Butyl {(1S,2R)-1-benzyl-2-hydroxy-2-[(4S)-2-isopropyl-5-oxo-1-(pyridin-3-ylmethyl)imidazolidin-4-yl]ethyl}carbamate

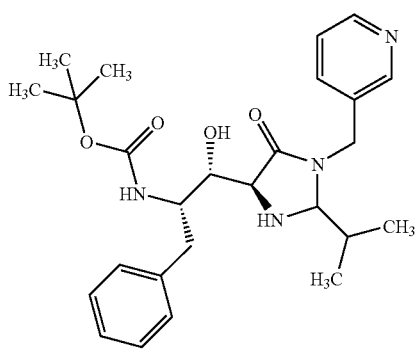

Step 1:

tert-Butyl {(1S,2R)-1-benzyl-2-hydroxy-2-[(4S)-2-isopropyl-5-oxo-1-(pyridin-3-ylmethyl)imidazolidin-4-yl]ethyl}carbamate The title compound was prepared using a sequence of procedures similar to that described in Example 1, except that 3-(aminomethyl)pyridine was used in placed of 2-amylamine in Step 6, and MeOH/EtOAc was used in place of MeOH in Step 7. Final purification cleanly afforded one diastereomer as the trifluoroacetate salt. ES MS (M+1)=469.

EXAMPLE 12 tert-Butyl {(1S,2R)-1-benzyl-2-hydroxy-2-[(4S)-2-isopropyl-5-oxo-1-(pyridin-4-ylmethyl)imidazolidin-4-yl]ethyl}carbamate

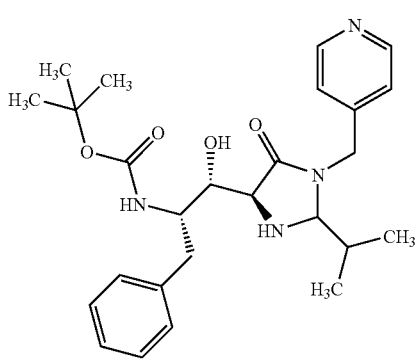

Step 1:

tert-Butyl {(1S,2R)-1-benzyl-2-hydroxy-2-[(4S)-isopropyl-5-oxo-1-(pyridin-4-ylmethyl)imidazolidin-4-yl]ethyl}carbamate The title compound was prepared using a sequence of procedures similar to that described in Example 1, except that 4-(aminomethyl)pyridine was used in placed of 2-amylamine in Step 6, and MeOH/EtOAc was used in place of MeOH in Step 7. Final purification cleanly afforded one diastereomer as the trifluoroacetate salt. ES MS (M+1)=469.

EXAMPLE 13 tert-Butyl ((1S,2R)-1-benzyl-2-{(4S)-1-[(1R)-1,5-dimethylhexyl]-2-isopropyl-5-oxoimidazolidin-4-yl}-2-hydroxyethyl)carbamate

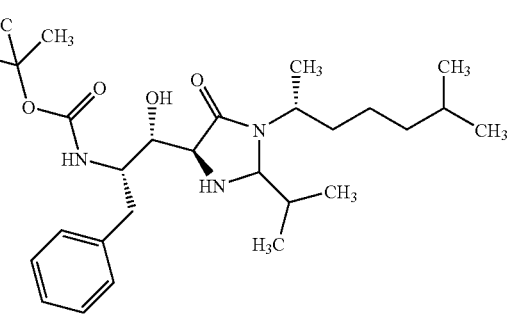

Step 1:

tert-Butyl ((1S,2R)-1-benzyl-2-{(4S)-1-[(1R)-1,5-dimethylhexyl]-2-isopropyl-5-oxoimidazolidin-4-yl}-2-hydroxyethyl)carbamate The title compound was prepared using a sequence of procedures similar to that described in Example 1, except that (R)-2-amino-6-methylheptane was used in placed of 2-amylamine in Step 6, and MeOH/EtOAc was used in place of MeOH in Step 7. In Step 8, the reaction was treated with additional isobutylaldehyde (50 μL) after one night of heating to 70° C. and was heated to 70° C. for an additional night. Final purification cleanly afforded one diastereomer as the trifluoroacetate salt. ES MS (M+1)=476.

EXAMPLE 14 tert-Butyl ((1S,2R)-1-benzyl-2-{(4S)-1-[(1S)-1,5-dimethylhexyl]-2-isopropyl-5-oxoimidazolidin-4-yl}-2-hydroxyethyl)carbamate

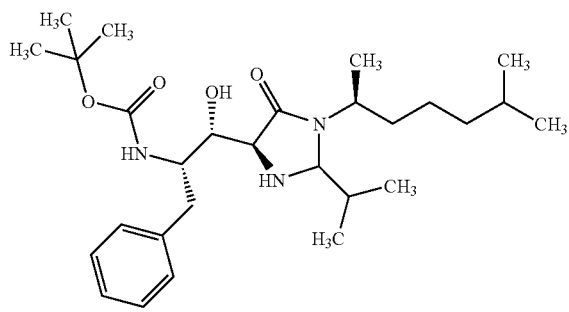

Step 1:

tert-Butyl ((1S,2R)-1-benzyl-2-{(4S)-1-[(1S)-1,5-dimethylhexyl]-2-isopropyl-5-oxoimidazolidin-4-yl}-2-hydroxyethyl)carbamate The title compound was prepared using a sequence of procedures similar to that described in Example 1, except that (S)-2-amino-6-methylheptane was used in placed of 2-amylamine in Step 6. In Step 8, the reaction was treated with additional isobutylaldehyde (50 μL) after one night of heating to 70° C. and was heated to 70° C. for an additional night. Final purification separately afforded the earlier and later eluting diastereomers as the trifluoroacetate salts. Earlier eluting diastereomer: ES MS (M+1)=490; Later eluting diastereomer: ES MS (M+1)=490.

EXAMPLE 15 tert-Butyl ((1S,2R)-1-benzyl-2-hydroxy-2-{(4S)-2-isopropyl-1-[4-(methylsulfonyl)benzyl]-5-oxoimidazolidin-4-yl}ethyl)carbamate

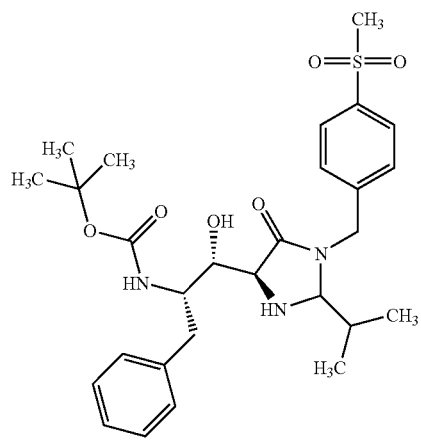

Step 1:

tert-Butyl ((1S,2R)-1-benzyl-2-hydroxy-2-{(4S)-2-isopropyl-1-[4-(methylsulfonyl)benzyl]-5-oxoimidazolidin-4-yl}ethyl)carbamate The title compound was prepared using a sequence of procedures similar to that described in Example 1, except that 4-methylsulphonylbenzylamine hydrochloride was used in placed of 2-amylamine in Step 6, and the reaction in Step 8 was heated to 70° C. overnight. Final purification cleanly afforded one diastereomer as the trifluoroacetate salt. ES MS (M+1)=546.

EXAMPLE 16 tert-Butyl ((1S,2R)-2-{(4S)-1-[2-(1,3-benzodioxol-5-yl)ethyl]-2-isopropyl-5-oxoimidazolidin-4-yl}-1-benzyl-2-hydroxyethyl)carbamate

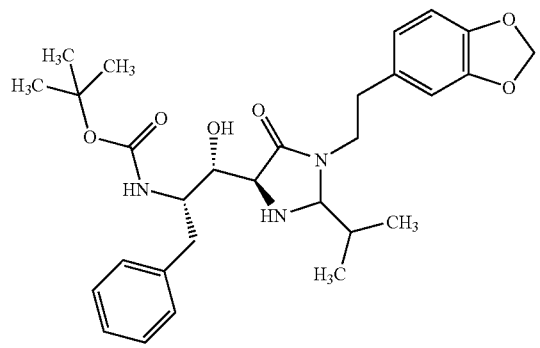

Step 1:

tert-Butyl ((1S,2R)-2-{(4S)-1-[2-(1,3-benzodioxol-5-yl)ethyl]-2-isopropyl-5-oxoimidazolidin-4-yl}-1-benzyl-2-hydroxyethyl)carbamate The title compound was prepared using a sequence of procedures similar to that described in Example 1, except that 3,4-methylenedioxyphenethylamine hydrochloride was used in placed of 2-amylamine in Step 6, and the reaction in Step 8 was heated to 70° C. overnight. Final purification separately afforded the earlier and later eluting diastereomers as the trifluoroacetate salts. Earlier eluting diastereomer: ES MS (M+1)=526; Later eluting diastereomer: ES MS (M+1)=526.

EXAMPLE 17 tert-Butyl {(1S,2R)-1-benzyl-2-hydroxy-2-[(4S)-2-isopropyl-5-oxo-1-(1-propylbutyl)imidazolidin-4-yl]ethyl}carbaate

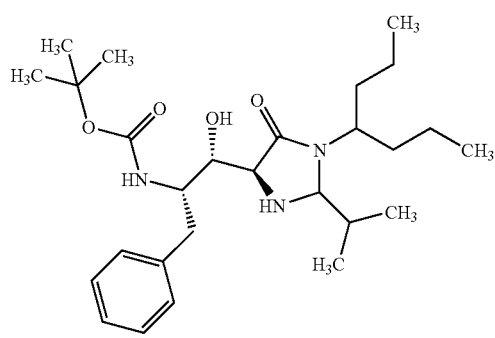

Step 1:

tert-Butyl {(1S,2R)-1-benzyl-2-hydroxy-2-[(4S)-2-isopropyl-5-oxo-1-(1-propylbutyl)imidazolidin-4-yl]ethyl}carbamate The title compound was prepared using a sequence of procedures similar to that described in Example 1, except that 4-aminoheptane was used in placed of 2-amylamine in Step 6, and the reaction in Step 8 was heated to 70° C. overnight. Final purification separately afforded the earlier and later eluting diastereomers as the trifluoroacetate salts. Earlier eluting diastereomer: ES MS (M+1)=476; Later eluting diastereomer: ES MS (M+1)=476.

EXAMPLE 18 tert-Butyl {(1S,2R)-1-benzyl-2-[(4S)-1-(3-fluorobenzyl)-2-isopropyl-5-oxoimidazolidin-4-yl]-2-hydroxyethyl}carbamate

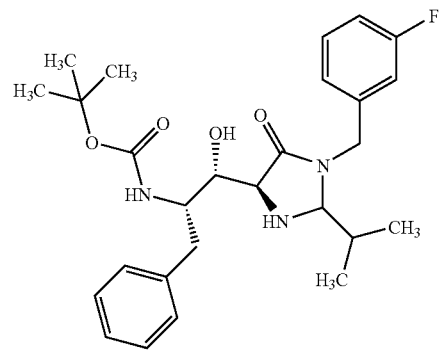

Step 1:

tert-Butyl {(1S,2R)-1-benzyl-2-[(4S)-1-(3-fluorobenzyl)-2-isopropyl-5-oxoimidazolidin-4-yl]-2-hydroxyethyl}carbamate The title compound was prepared using a sequence of procedures similar to that described in Example 1, except that 3-fluorobenzylamine was used in placed of 2-amylamine in Step 6, and MeOH/EtOAc was used in place of MeOH in Step 7. The reaction in Step 8 was heated to 70° C. overnight. Final purification cleanly afforded one diastereomer as the trifluoroacetate salt. ES MS (M+1)=486.

EXAMPLE 19 tert-Butyl {(1S,2R)-1-benzyl-2-[(4S)-1-(4-fluorobenzyl)-2-isopropyl-5-oxoimidazolidin-4-yl]-2-hydroxyethyl}carbamate

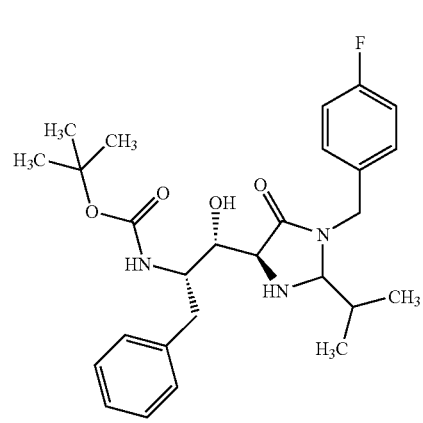

Step 1:

tert-Butyl {(1S,2R)-1-benzyl-2-[(4S)-1-(4-fluorobenzyl)-2-isopropyl-5-oxoimidazolidin-4-yl]-2-hydroxyethyl}carbamate The title compound was prepared using a sequence of procedures similar to that described in Example 1, except that 4-fluorobenzylamine was used in placed of 2-amylamine in Step 6, and MeOH/EtOAc was used in place of MeOH in Step 7. The reaction in Step 8 was heated to 70° C. overnight. Final purification separately afforded the earlier and later eluting diastereomers as the trifluoroacetate salts. Earlier eluting diastereomer: ES MS (M+1)=486; Later eluting diastereomer: ES MS (M+1)=486.

EXAMPLE 20 tert-Butyl ((1S,2R)-1-benzyl-2-hydroxy-2-{(4S)-2-isopropyl-5-oxo-1-[3-(trifluoromethoxy)benzyl]imidazolidin-4-yl}ethyl)carbamate

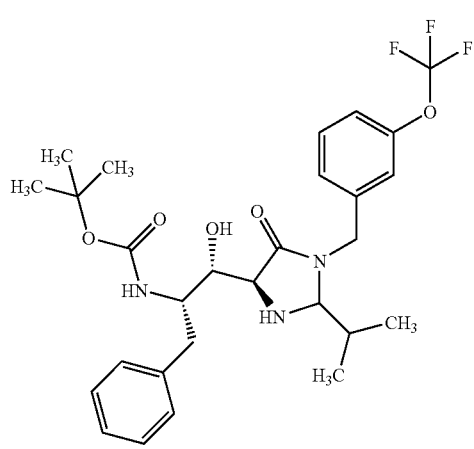

Step 1:

tert-Butyl ((1S,2R)-1-benzyl-2-hydroxy-2-{(4S)-2-isopropyl-5-oxo-1-[3-(trifluoromethoxy)benzyl]imidazolidin-4-yl}ethyl)carbamate The title compound was prepared using a sequence of procedures similar to that described in Example 1, except that 3-(trifluoromethoxy)benzylamine was used in placed of 2-amylamine in Step 6, and MeOH/EtOAc was used in place of MeOH in Step 7. The reaction in Step 8 was heated to 70° C. overnight. Final purification cleanly afforded one diastereomer as the trifluoroacetate salt. ES MS (M+1)=552.

EXAMPLE 21 tert-Butyl ((1S,2R)-1-benzyl-2-{(4S)-1-[2-fluoro-4-(trifluoromethyl)benzyl]-2-isopropyl-5-oxoimidazolidin-4-yl}-2-hydroxyethyl)carbamate

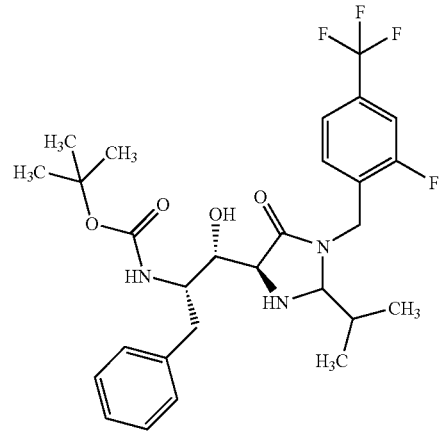

Step 1:

tert-Butyl ((1S,2R)-1-benzyl-2-{(4S)-1-[2-fluoro-4-(trifluoromethyl)benzyl]-2-isopropyl-5-oxoimidazolidin-4-yl}-2-hydroxyethyl)carbamate The title compound was prepared using a sequence of procedures similar to that described in Example 1, except that 2-fluoro-4-(trifluoromethyl)benzylamine was used in placed of 2-amylamine in Step 6, and MeOH/EtOAc was used in place of MeOH in Step 7. The reaction in Step 8 was heated to 70° C. overnight. Final purification cleanly afforded one diastereomer as the trifluoroacetate salt. ES MS (M+1)=554.

EXAMPLE 22 tert-Butyl {(1S,2R)-1-benzyl-2-[(2S,4S)-1-benzyl-2-ethyl-5-oxoimidazolidin-4-yl]-2-hydroxyethyl}carbamate

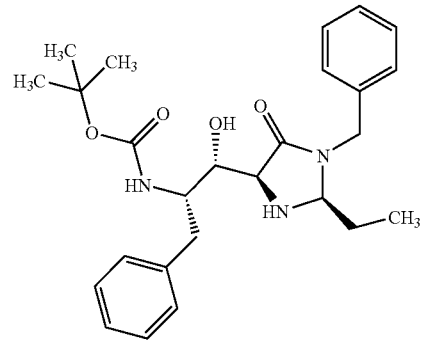

Step 1:

2-Azido-N-(benzyl)-4-[(tert-butoxycarbonyl)amino]-
2,4,5-trideoxy-5-phenyl-L-ribonic amide A solution of 2-azido-4-[(tert-butoxycarbonyl)amino]-2,4,5-trideoxy-5-phenyl-L-ribonic acid (147 mg, 0.420 mmol), benzylamine (55 μL, 0.503 mmol), HOAT (63 mg, 0.461 mmol), and EDC (129 mg, 0.671 mmol) in DMF (1 mL) was stirred at rt for 4 h. The solution was diluted with EtOAc (30 mL) and washed with 10% $KHSO_4$ solution, water, and brine. The organic extract was dried over $MgSO_4$, filtered, and concentrated in vacuo. The resulting residue was purified twice by flash column chromatography on silica gel using gradient elutions of 10-60% EtOAc/hexanes and 0-20% tert-butylmethyl ether/$CH_2Cl_2$. Collection and concentration of the appropriate fractions yielded the product.

$^1$H NMR (400 MHz, $CDCl_3$) δ 7.43-7.19 (m, 10H), 4.70 (br s, 1H), 4.51 (ddd, J=6.0, 14.8, 21.2 Hz, 2H), 4.18 (br s, 1H), 3.93 (br s, 3H), 3.01 (dd, J=3.6, 14.0 Hz, 1H), 2.96-2.94 (m, 1H), 1.35 (s, 9H).

Step 2:

2-Amino-N-(benzyl)-4-[(tert-butoxycarbonyl)amino]-2,4,5-trideoxy-5-phenyl-L-ribonic amide A suspension of 2-azido-N-(benzyl) [(tert-butoxycarbonyl)amino]-2,4,5 -trideoxy-5-phenyl-L-ribonic amide (55 mg, 0.125 mmol) in MeOH was sonicated and heated to form a solution. The solution was flushed with nitrogen gas and treated with 10% palladium on carbon (13 mg, 0.125 mmol) and bubbling hydrogen gas for 3 h. The mixture was stirred under hydrogen atmosphere for 3 h and then filtered through celite. The resulting filtrate was concentrated in vacuo to afford the product as a white solid. ES MS (M+1)=414.

Step 3:

tert-Butyl {(1S,2R)-1-benzyl-2-[(2S,4S)-1 -benzyl-2-ethyl-5-oxoimidazolidin-4-yl]-2-hydroxyethyl}carbamate To a solution of 2-amino-N-(benzyl)-4-[(tert-butoxycarbonyl)amino]-2,4,5-trideoxy-5-phenyl-L-ribonic amide (40 mg, 0.097 mmol) in MeOH (2 mL) were added propionaldehyde (84 mg, 1.451 mmol) and small amounts of p-toluene sulfonic acid monohydrate and $Na_2SO_4$. The mixture was heated to reflux for 10 h. The reaction was diluted with EtOAc (20 mL), washed with saturated aqueous $NaHCO_3$ solution and brine, dried over $Na_2SO_4$, filtered, and concentrated in vacuo. The resulting residue was purified by flash column chromatography on silica gel using a gradient elution of 30-50% EtOAc/hexanes. Collection and concentration of the appropriate fractions afforded the title compound.

$^1$H NMR (400 MHz, $CDCl_3$) δ 7.52-7.28 (m, 6H), 7.23-7.00 (m, 4H), 5.39 (d, J=9.2 Hz, 1H), 4.87 (d, J=15.2 Hz, 1H), 4.29 (br s, 1H), 4.21-4.12 (m, 2H), 4.02 (d, J=14.8 Hz, 1H), 3.81 (br s, 1H), 3.54 (d, J=8.4 Hz, 1H), 3.04-2.88 (m, 2H), 1.73-1.66 (m, 2H), 1.36 (s, 9H), 0.81 (t, J=7.2 Hz, 3H); ES MS (M+1)=454.

EXAMPLE 23 tert-Butyl {(1S,2R)-1-benzyl-2-[(4S)-1-benzyl-2-methyl-5-oxoimidazolidin-4-yl]-2-hydroxyethyl}carbamate

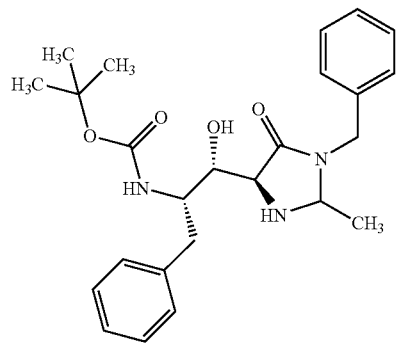

Step 1:

tert-Butyl {(1S,2R)-1-benzyl-2-[(4S)-1-benzyl-2-methyl-5-oxoimidazolidin-4-yl]-2-hydroxyethyl}carbamate The title compound was prepared using a procedure similar to that described in Example 22, Step 3, except that acetaldehyde was used in placed of propionaldehyde. The reaction was filtered and the resulting filtrate purified by reverse phase chromatography on a C-18 column using a gradient elution of 95-5% $H_2O$ (0.1% TFA)/$CH_3CN$ (0.1% TFA). Collection and concentration of the appropriate fractions afforded the product as a mixture of diastereomers in the form of trifluoroacetate salts. HRMS (FT-ICR) $C_{25}H_{33}N_3O_4$+H=440.2588; calculated 440.2544.

EXAMPLE 24 tert-Butyl {(1S,2R)-1-benzyl-2-[(4S)-1-benzyl-5-oxo-2-propylimidazolidin-4-yl]-2-hydroxyethyl}carbamate

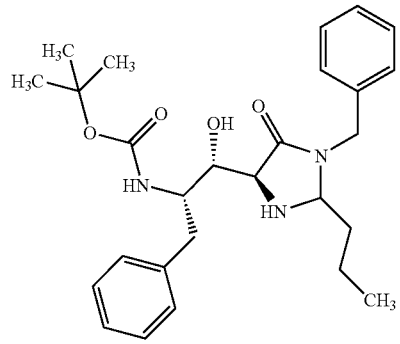

Step 1:

tert-Butyl {(1S,2R)-1-benzyl-2-[(4S)-1-benzyl-5-oxo-2-propylimidazolidin-4-yl]-2-hydroxyethyl}carbamate The title compound was prepared using a procedure similar to that described in Example 22, Step 3, except that butyraldehyde was used in placed of propionaldehyde. The reaction was filtered and the resulting filtrate purified by reverse phase chromatography on a C-18 column using a gradient elution of 95-5% $H_2O$ (0.1% TFA)/$CH_3CN$ (0.1% TFA). Collection and concentration of the appropriate fractions separately afforded the earlier and later eluting diastereomer products as the trifluoroacetate salts. Earlier eluting diastereomer: ES MS (M+1)=468; Later eluting diastereomer: HRMS (FT-ICR) $C_{27}H_{37}N_3O_4$+H=468.2880; calculated 468.2857.

EXAMPLE 25 tert-Butyl {(1S,2R)-1-benzyl-2-[(4S)-1-benzyl-2-butyl-5-oxoimidazolidin-4-yl]-2-hydroxyethyl}carbamate

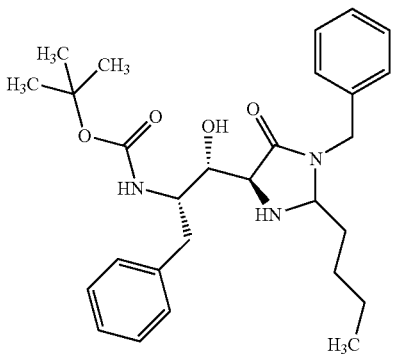

Step 1:

tert-Butyl {(1S,2R)-1-benzyl-2-[(4S)-1-benzyl-2-butyl-5-oxoimidazolidin-4-yl]-2-hydroxyethyl}carbamate The title compound was prepared using a procedure similar to that described in Example 22, Step 3, except that valeraldehyde was used in placed of propionaldehyde. The reaction was filtered and the resulting filtrate purified by reverse phase chromatography on a C-18 column using a gradient elution of 95-5% $H_2O$ (0.1% TFA)/$CH_3CN$ (0.1% TFA). Collection and concentration of the appropriate fractions separately afforded the earlier and later eluting diastereomer products as the trifluoroacetate salts. Earlier eluting diastereomer: HRMS (FT-ICR) $C_{28}H_{39}N_3O_4$+H=482.3407; calculated 482.3014; Later eluting diastereomer: HRMS (FT-ICR) $C_{28}H_{39}N_3O_4$+H=482.3054; calculated 482.3014.

EXAMPLE 26 tert-Butyl {(1S,2R)-1-benzyl-2-[(4S)-1-benzyl-2-isopropyl-5-oxoimidazolidin-4-yl]-2-hydroxyethyl}carbamate

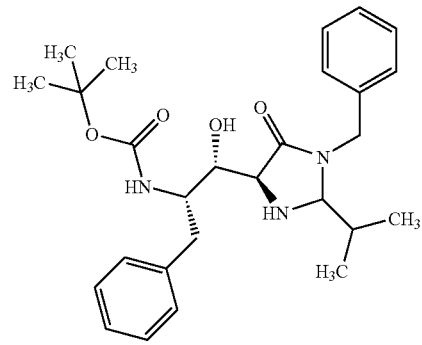

Step 1:

tert-Butyl {(1S,2R)-1-benzyl-2-[(4S)-1-benzyl-2-isopropyl-5-oxoimidazolidin-4-yl]-2-hydroxyethyl}carbamate The title compound was prepared using a procedure similar to that described in Example 22, Step 3, except that isobutylaldehyde was used in placed of propionaldehyde. The reaction was filtered and the resulting filtrate purified by reverse phase chromatography on a C-18 column using a gradient elution of 95-5% $H_2O$ (0.1% TFA)/$CH_3CN$ (0.1% TFA). Collection and concentration of the appropriate fractions separately afforded the earlier and later eluting diastereomer products as the trifluoroacetate salts. Earlier eluting diastereomer: HRMS (FT-ICR) $C_{27}H_{37}N_3O_4$+H=468.2890; calculated 468.2857; Later eluting diastereomer: HRMS (FT-ICR) $C_{27}H_{37}N_3O_4$+H=468.2890; calculated 468.2857.

EXAMPLE 27

Phenyl {(1S,2R)-1-benzyl-2-[(4S)-1-benzyl-2-isopropyl-5-oxoimidazolidin-4-yl]-2-hydroxyethyl}carbamate

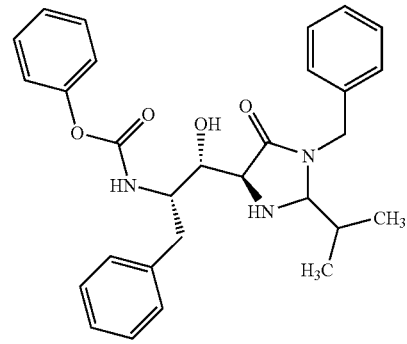

Step 1:

4-Amino-2-azido-N-(benzyl)-2,4,5-trideoxy-5-phenyl-L-ribonic amide

A suspension of 2-azido-N-(benzyl)-4-[(tert-butoxycarbonyl)amino]-2,4,5-trideoxy-5-phenyl-L-ribonic amide (47 mg, 0.107 mmol) in EtOAc (75 mL) was cooled to 0° C. and treated with HCl gas for 5 min. The reaction was stirred for 1 h and concentrated in vacuo to afford the product as a white solid. $^1$H NMR (400 MHz, $d_6$-DMSO) δ 8.89 (t, J=5.6 Hz, 1H), 7.89 (br s, 3H), 7.38-7.20 (m, 10H), 6.28 (d, J=6.4 Hz, 1H), 4.38 (dddd, J=6.0, 15.2, 20.8, 28.0 Hz, 2H), 4.25-4.21 (m, 1H), 3.95 (d, J=8.8 Hz, 1H), 3.02 (dd, J=4.0, 14.4 Hz, 1H), 2.78 (dd, J=9.2, 14.8 Hz, 1H); ES MS (M+1)=340.

Step 2:

2-Azido-N-(benzyl)-4-[(phenyloxycarbonyl)amino]-2,4,5-trideoxy-5-phenyl-L-ribonic amide To a solution of 4-amino-2-azido-N-(benzyl)-2,4,5-trideoxy-5-phenyl-L-ribonic amide (36 mg, 0.106 mmol) in $CH_2Cl_2$ (5 mL) at 0° C. was added phenyl chloroformate (13 μL, 0.106 mmol) and triethylamine (37 μL, 0265 mmol). The reaction was stirred for 30 min at 0° C. and diluted with $CH_2Cl_2$ (75 mL). The resulting mixture was washed with 10% aqueous $KHSO_4$ solution and brine, dried over $MgSO_4$, filtered, and concentrated in vacuo to afford the product. $^1$H NMR (400 MHz, $CDCl_3$) δ 7.36-7.23 (m, 11H), 7.20-7.16 (m, 2H), 6.97 (d, J=8.0 Hz, 2H), 5.35 (d, J=8.4 Hz, 1H), 4.53 (dd, J=6.0, 15.2 Hz, 1H), 4.43 (dd, J=5.6, 14.8 Hz, 1H), 4.13-4.04 (m, 3H), 4.01 (d, J=4.0 Hz, 1H), 3.11-2.99 (m, 2H); ES MS (M+1)=460.

Step 3:

2-Amino-N-(benzyl)-4-[(phenyloxycarbonyl)amino]-2,4,5-trideoxy-5-phenyl-L-ribonic amide A suspension of 2-azido-N-(benzyl)-4-[(phenyloxycarbonyl)amino]-2,4,5-trideoxy-5-phenyl-L-ribonic amide (70 mg, 0.152 mmol) in MeOH was flushed with nitrogen gas and treated with a small amount of 10% palladium on carbon and bubbling hydrogen gas for 3 h. The mixture was filtered through celite, and the resulting filtrate was concentrated in vacuo to afford the product. HRMS (FT-ICR) $C_{25}H_{27}N_3O_4$+H=434.2051; calculated 434.2075.

Step 4:

Phenyl {(1S,2R)-1-benzyl-2-[(4S)-1-benzyl-2-isopropyl-5-oxoimidazolidin-4-yl]-2-hydroxyethyl}carbamate To a solution of 2-amino-N-(benzyl)-4-[(phenyloxycarbonyl)amino]-2,4,5-trideoxy-5-phenyl-L-ribonic amide (49 mg, 0.113 mmol) in MeOH were added isobutylaldehyde (82 mg, 1.130 mmol) and a small amount of p-toluene sulfonic acid. The mixture was heated to reflux overnight. The reaction was diluted with EtOAc (20 mL), washed with saturated aqueous $NaHCO_3$ solution, dried over $MgSO_4$, filtered, and concentrated in vacuo. The resulting residue was purified by flash column chromatography on silica gel using a gradient elution of 15-50% EtOAc/hexanes. Collection and concentration of the appropriate fractions afforded a white solid which was purified again by reverse phase chromatography on a C-18 column using a gradient elution of 95-5% $H_2O$ (0.1% TFA)/$CH_3CN$ (0.1% TFA). Collection and concentration of the appropriate fractions separately afforded the earlier and later eluting diastereomers as the trifluoroacetate salts. The products were individually partitioned between EtOAc and saturated $NaHCO_3$ solution. The organic layers were washed with brine, dried over $MgSO_4$, filtered, and concentrated in vacuo to afford the title compounds in free base form Earlier eluting diastereomer: $^1$H NMR (400 MHz, $CDCl_3$) δ 7.40-7.16 (m, 13H), 7.07 (d, J=8.0 Hz, 2H), 6.02 (d, J=8.8 Hz, 1H), 4.92 (d, J=15.2 Hz, 1H), 4.31-4.29 (m, 2H), 4.18 (t, J=2.0 Hz, 1H), 3.92 (d, J=15.2 Hz, 1H), 3.86 (dd, J=3.6, 8.8 Hz, 1H), 3.54 (dd, J=2.0, 8.8 Hz, 1H), 3.16 (dd, J=8.0, 14.0 Hz, 1H), 3.00 (dd, J=5.6, 14.0 Hz, 1H), 1.89-1.85 (m, 1H), 0.71 (d, J=7.2 Hz, 3H), 0.52 (d, J=6.8 Hz, 3H); Later eluting diastereomer: HRMS (FT-ICR) $C_{29}H_{33}N_3O_4$+H=488.2534; calculated 488.2544.

EXAMPLE 28

Phenyl {(1S,2R)-1-benzyl-2-[(2S,4S)-1-benzyl-2-butyl-5-oxoimidazolidin-4-yl]-2-hydroxyethyl}carbamate

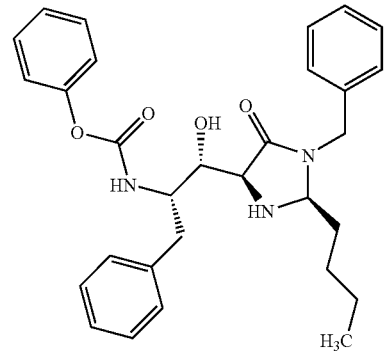

Step 1:

Phenyl {(1S,2R)-1-benzyl-2-[(2S,4S)-1-benzyl-2-butyl-5-oxoimidazolidin-4-yl]-2-hydroxyethyl}carbamate The title compound was prepared using a procedure similar to that described in Example 27, Step 4, except that valeraldehyde was used in place of isobutylaldehyde. Purification was achieved by reverse phase chromatography on a C-18 column using a gradient elution of 60-40% $H_2O$ (0.1% TFA)/$CH_3CN$ (0.1% TFA). Collection and concentration of the appropriate fractions afforded the product as its trifluoroacetate salt. HRMS (FT-ICR) $C_{30}H_{35}N_3O_4$+H=502.2683; calculated 502.2701.

EXAMPLE 29

Phenyl {(1S,2R)-1-benzyl-2-[(6S)-8-benzyl-7-oxo-5,8-diazaspiro[3.4]oct-6-yl]-2-hydroxyethyl}carbamate

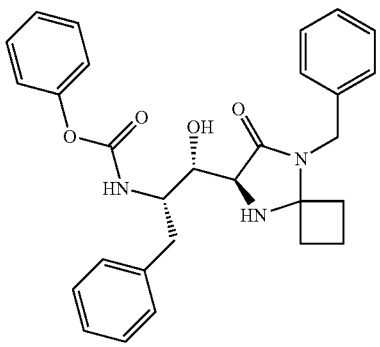

Step 1:

Phenyl {(1S,2R)-1-benzyl-2-[(6S)-8-benzyl-7-oxo-5,8-diazaspiro[3.4]oct-6-yl]-2-hydroxyethyl}carbamate The title compound was prepared using a procedure similar to that described in Example 27, Step 4, except that cyclobutanone was used in place of isobutylaldehyde. Purification was achieved by reverse phase chromatography on a C-18 column using a gradient elution of 95-5% $H_2O$ (0.1% TFA)/$CH_3CN$ (0.1% TFA). Collection and concentration of the appropriate fractions afforded the product as the trifluoroacetate salt. HRMS (FI-MALDI) $C_{29}H_{31}N_3O_4$+H=486.2386; calculated 486.2387.

EXAMPLE 30

Phenyl {(1S,2R)-1-benzyl-2-[(2S)-4-benzyl-3-oxo-8-oxa-1,4-diazaspiro[4.5]dec-2-yl]-2-hydroxyethyl}carbamate

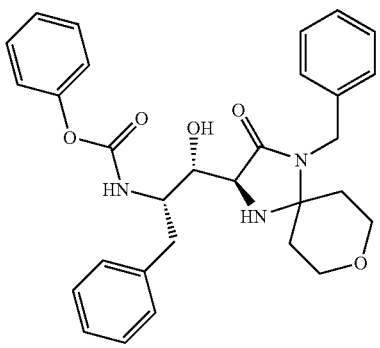

Step 1:

Phenyl {(1S,2R)-1-benzyl-2-[(2S)-4-benzyl-3-oxo-8-oxa-1,4-diazaspiro[4.5]dec-2-yl]-2-hydroxyethyl}carbamate The title compound was prepared using a procedure similar to that described in Example 27, Step 4, except that tetrahydro-4H-pyran-4-one was used in place of isobutylaldehyde. Purification was achieved by reverse phase chromatography on a C-18 column using a gradient elution of 95-5% $H_2O$ (0.1% TFA)/$CH_3CN$ (0.1% TFA). Collection and concentration of the appropriate fractions afforded the product as the trifluoroacetate salt. HRMS (Fr-MALDI) $C_{30}H_{33}N_3O_5$+H=516.2495; calculated 516.2493.

EXAMPLE 31

Phenyl {(1S,2R)-1-benzyl-2-[(2S)-4-benzyl-8-methyl-3-oxo-1,4-diazaspiro[4.5]dec-2-yl]--hydroxyethyl}carbamate

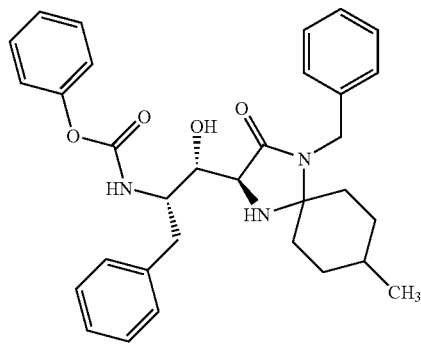

Step 1:

Phenyl {(1S,2R)-1-benzyl-2-[(2S)-4-benzyl-8-methyl-3-oxo-1,4-diazaspiro[4.5]dec-2-yl]-2-hydroxyethyl}carbamate The title compound was prepared using a procedure similar to that described in Example 27, Step 4, except that 4-methylcyclohexanone was used in place of isobutylaldehyde. Purification was achieved by reverse phase chromatography on a C-18 column using a gradient elution of 95-5% $H_2O$ (0.1% TFA)/$CH_3CN$ (0.1% TFA). Collection and concentration of the appropriate fractions afforded the product as the trifluoroacetate salt. HRMS (FT-MALDI) $C_{32}H_{37}N_3O_4$+H=528.2862; calculated 528.2857.

EXAMPLE 32

Phenyl {(1S,2R)-1-benzyl-2-[(4S)-1-benzyl-2,2-dibutyl-5-oxoimidazolidin-4-yl]-2-hydroxyethyl}carbamate

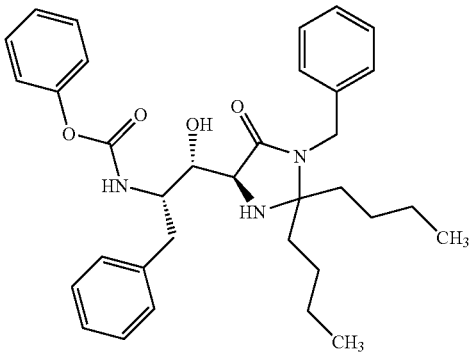

Step 1:

Phenyl {(1S,2R)-1-benzyl-2-[(4S)-1-benzyl-2,2-dibutyl-5-oxoimidazolidin-4-yl]-2-hydroxyethyl}carbamate The title compound was prepared using a procedure similar to that described in Example 27, Step 4, except that 5-nonanone was used in place of isobutylaldehyde. Purification was achieved by reverse phase chromatography on a C-18 column using a gradient elution of 95-5% $H_2O$ (0.1% TFA)/$CH_3CN$ (0.1% TFA). Collection and concentration of the appropriate fractions afforded the product as the trifluoroacetate salt. HRMS (FT-MALDI) $C_{34}H_{43}N_3O_4$+H=558.3327; calculated 558.3326.

EXAMPLE 33

Phenyl {(1S,2R)-1-benzyl-2-[(2S)-4-benzyl-3-oxo-1,4-diazaspiro[4.4]non-2-yl]-2-hydroxyethyl}carbamate

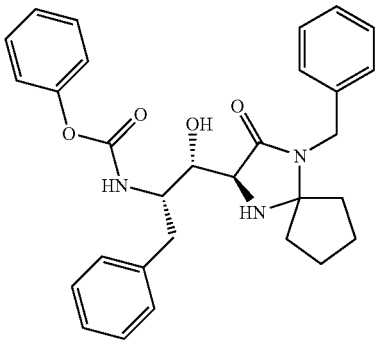

Step 1:

Phenyl {(1S,2R)-1-benzyl-2-[(2S)-4-benzyl-3-oxo-1,4-diazaspiro[4.4]non-2-yl]-2-hydroxyethyl}carbamate The title compound was prepared using a procedure similar to that described in Example 27, Step 4, except that cyclopentanone was used in place of isobutylaldehyde. Purification was achieved by reverse phase chromatography on a C-18 column using a gradient elution of 75-25% $H_2O$ (0.1% TFA)/$CH_3CN$ (0.1% TFA). Collection and concentration of the appropriate fractions afforded the product as the trifluoroacetate salt. HRMS (FT-MALDI) $C_{30}H_{33}N_3O_4$+H=500.2542; calculated 500.2544.

EXAMPLE 34

Phenyl {(1S,2R)-1-benzyl-2-[(4S)-1-benzyl-5-oxo-2-phenylimidazolidin-4-yl]-2-hydroxyethyl}carbamate

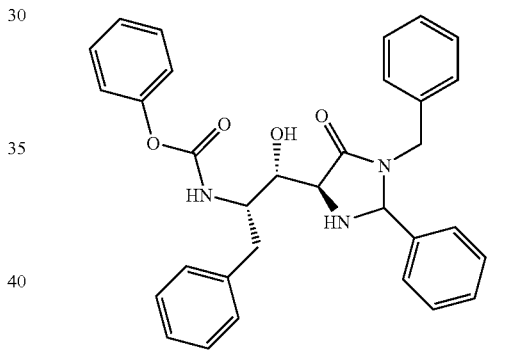

Step 1:

Phenyl {(1S,2R)-1-benzyl-2-[(4S)-1-benzyl-5-oxo-2-phenylimidazolidin-4-yl]-2-hydroxyethyl}carbamate The title compound was prepared using a procedure similar to that described in Example 27, Step 4, except that benzaldehyde was used in place of isobutylaldehyde. Purification was achieved by reverse phase chromatography on a C-18 column using a gradient elution of 75-25% $H_2O$ (0.1% TFA)/$CH_3CN$ (0.1% TFA). Collection and concentration of the appropriate fractions separately afforded the earlier and later eluting diastereomers as the trifluoroacetate salts. Earlier eluting diastereomer: HRMS (FT-MALDI) $C_{32}H_{31}N_3O_4$+H=522.2387; calculated 522.2387; Later eluting diastereomer: HRMS (Fr-MALDI) $C_{32}H_{31}N_3O_4$+H=522.2387; calculated 522.2387.

EXAMPLE 35

Phenyl ((1S,2R)-1-benzyl-2-{(4S)-2-butyl-5-oxo-1-[(1S)-1-phenylethyl]imidazolidin-4-yl}-2-hydroxyethyl)carbamate

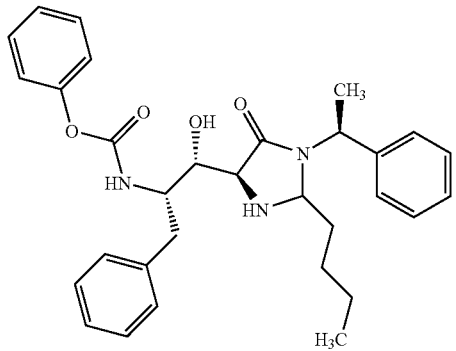

Step 1:

2-Azido-N-[(1S)-1-phenylethyl]-4-[(tert-butoxycarbonyl)amino]-2,4,5-trideoxy-5-phenyl-L-ribonic amide The compound was prepared using a procedure similar to that described in Example 22, Step 1, except that (S)-(−)-α-methylbenzylamine was used in place of benzylamine. Purification by chromatography was unnecessary. ES MS (M+1)=454.

Step 2:

2-Azido-N-[(1S)-1-phenylethyl]-4-[(phenyloxycarbonyl)amino]-2,4,5-trideoxy-5-phenyl-L-ribonic amide The compound was prepared using procedures similar to those described in Example 27, Step 1 and Step 2. Purification was achieved by flash column chromatography on silica gel using a gradient elution of 10-75% EtOAc/hexanes. Collection and concentration of the appropriate fractions afforded the product as a white solid. ES MS (M+1)=473.

Step 3:

2-Amino-N-[(1S)-1-phenylethyl]-4-[(phenyloxycarbonyl)amino]-2,4,5-trideoxy-5-phenyl-L-ribonic amide The compound was prepared using a procedure similar to that described in Example 27, Step 3. ES MS (M+1)=448.

Step 4:

Phenyl ((1S,2R)-1-benzyl-2-{(4S)-2-butyl-5-oxo-1-[(1S)-1-phenylethyl]imidazolidin-4-yl}-2-hydroxyethyl)carbamate The title compound was prepared using a procedure similar to that described in Example 27, Step 4, except that valeraldehyde was used in place of isobutylaldehyde. Purification was achieved by reverse phase chromatography on a C-18 column using a gradient elution of 95-5% H$_2$O (0.1% TFA)/CH$_3$CN (0.1% TFA). Collection and concentration of the appropriate fractions separately afforded the earlier and later eluting diastereomers as their trifluoroacetate salts. Earlier eluting diastereomer: ES MS (M+1)=516; Later eluting diastereomer: ES MS (M+1)=516.

EXAMPLE 36

N-[(1S)-1-Benzyl-2-(1-benzyl-2,2-dimethyl-5-oxoimidazolidin-4-yl)-2-hydroxyethyl]-N'-[(1R)-1-(4-fluorophenyl)ethyl]-5-[1-methylsulfonyl)ethyl]isophthalamide

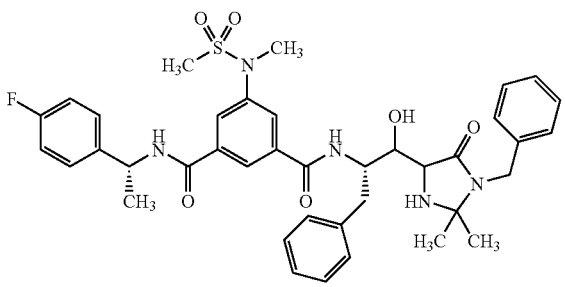

Step 1:

N$^1$-Benzyl-N-(tert-butoxycarbonyl)glycinamide

To a solution of N-(tert-butoxycarbonyl)glycine (20.00 g, 114.16 mmol) in DMF (75 mL) was added benzylamine (24.9 mL, 228.32 mmol). The solution was cooled to 0° C. and treated with EDC (43.77 g, 228.32 mmol) and HOAT (15.54 g, 114.16 mmol). The reaction was stirred at 0° C. for 10 min and at rt for 2 h. The solvent was removed in vacuo, and the resulting residue was partitioned between EtOAc, ice water, and saturated aqueous NaHCO$_3$ solution. The layers were separated, and the organic extract was washed twice with water, once with 10% aqueous KHSO$_4$ solution, twice more with water, and once with brine. The organic layer was dried over Na$_2$SO$_4$, filtered, and concentrated in vacuo to afford the product as a white solid $^1$H NMR (400 MHz, CDCl$_3$) δ 7.35-7.26 (m, 5H), 6.44 (br s, 1H), 5.14 (br s, 1H), 4.46 (d, J=6.0 Hz, 2H), 3.83 (d, J=6.0 Hz, 2H), 1.43 (s, 9H); ES MS (M+23)=287.

Step 2:

N$^1$-Benzylglycinamide

A solution of N$^1$-benzyl-N-tert-butoxycarbonyl)glycinamide (28.26 g, 106.91 mmol) in EtOAc was cooled to 0° C., treated with bubbling hydrogen chloride gas until saturation was achieved, and stirred for 20 min. This sequence was executed three times until the starting material was consumed. The solution was treated with bubbling nitrogen gas, and the resulting precipitate was filtered and washed twice with EtOAc and twice with Et$_2$O. The product was obtained as a white solid in the form of the hydrochloride salt. $^1$H NMR (400 MHz, CD$_3$OD) δ 7.34-7.31 (m, 4H), 7.30-7.24 (m, 1H), 4.43 (s, 2H), 3.71 (s, 2H); ES MS (M+1)=165.

Step 3:

3-Benzyl-2,2-dimethylimidazolidin-4-one

To a solution of $N^1$-benzylglycinamide (3.00 g, 14.95 mmol) in MeOH (25 mL) were added acetone (5.50 mL, 74.75 mmol) and triethylamine (1.67 mL, 11.96 mmol). The solution was stirred and heated to reflux overnight under an atmosphere of nitrogen. The solvent was removed in vacuo, and the resulting orange oil was purified by flash column chromatography on silica gel using a gradient elution of 0-7% (MeOH/NH$_3$)/CH$_2$Cl$_2$. Collection and concentration of the appropriate fractions afforded the product as a yellow oil. $^1$H NMR (400 MHz, CDCl$_3$) δ 7.31-7.27 (m, 5H), 4.44 (s, 2H), 3.55 (s, 2H), 1.26 (s, 6H); ES MS (M+1)=205.

Step 4:

Benzyl 3-benzyl-2,2-dimethyl-4-oxoimidazolidine-1-carboxylate

A cold (0° C.) solution of 3-benzyl-2,2-dimethylimidazolidin-4 -one (2.28 g, 11.16 mmol) in CH$_2$Cl$_2$ (25 mL) was treated with benzylchloroformate (0.96 mL, 6.70 mmol), a solution of 4-dimethylaminopyridine (1.71 g, 13.95 mmol) in CH$_2$Cl$_2$ (10 mL), and again with benzylchloroformate (0.96 mL, 6.70 mmol). The solution was stirred for 30 min and poured into aqueous 10% KHSO$_4$ solution. The layers were separated, and the organic was washed twice with water and once with brine. The organic layer was dried over Na$_2$SO$_4$, filtered, and concentrated in vacuo to afford an orange oil. The oil was treated with Et$_2$O causing a precipitate which was filtered to afford the product as a white solid. $^1$H NMR (400 MHz, CDCl$_3$) δ 7.37 (m, 10H), 5.14 (s, 2H), 4.54 (s, 2H), 4.11 (s, 6H), 1.56 (s, 6H); ES MS (M+1)=339.

Step 5:

Benzyl 3-benzyl-5-[(2S)-2-dibenzylamino)-1-hydroxy-3-phenylpropyl]-2,2-dimethyl-4-oxoimidazolidine-1-carboxylate A solution of S-(+)-2-dibenzylamino-3-phenyl-1-propanol (5.29 g, 15.96 mmol) in anhydrous CH$_2$Cl$_2$ (50 mL) and anhydrous DMSO (30 mL) under an atmosphere of nitrogen at 0° C. was treated with triethylamine (8.89 mL, 63.84 mmol) and a solution of sulfur trioxide pyridine complex (10.16 g, 63.84 mmol) in anhydrous DMSO (40 mL). The latter was added over 20 min. The resulting yellow solution was stirred at 0° C. for 10 min and at rt for 2 h. The reaction was cooled to 0° C. and treated with brine (220 mL) and water (40 mL). The solution was extracted with Et$_2$O (3×250 mL), and the combined organic layers were washed with aqueous 10% sodium bisulfite solution (220 mL) and brine (200 mL), dried over Na$_2$SO$_4$, filtered, and concentrated in vacuo to afford a yellow oil. Purification was achieved by flash column chromatography on silica gel using a gradient elution of 0-10% EtOAc/hexanes. Collection and concentration of the appropriate fractions afforded (2S)-2-(dibenzylamino)-3-phenylpropanal as a yellow oil. Anhydrous THF (15 mL) under an atmosphere of nitrogen was cooled to −78° C. and treated with 2.0M lithium diisopropylamine in THF (488 µL, 0.975 mmol) and a solution of benzyl 3-benzyl-2,2-dimethyl-4-oxoimidazolidine-1-carboxylate (300 mg, 0.886 mmol) in anhydrous THF (5 mL). The latter was added dropwise over 15 min. The mixture was stirred at −78° C. for 20 min and treated with a solution of (2S)-2 -(dibenzylamino)-3-phenylpropanal (526 mg, 1.60 mmol) in anhydrous THF (3 mL) over 15 min. The mixture was again stirred for 20 min at −78° C. and then allowed to warm to rt overnight. The reaction was poured into a saturated aqueous NH$_4$Cl solution and extracted three times with Et$_2$O. The combined organic layers were washed once with brine, dried over MgSO$_4$, filtered, and concentrated in vacuo to afford a yellow oil. Purification was achieved by flash column chromatography on silica gel using a gradient elution of 0-45% EtOAc/hexanes. Collection and concentration of the appropriate fractions afforded the product as a yellow oil. ES MS (M+1)=668.

Step 6:

5-[(2S)-2-Amino-1-hydroxy-3-phenylpropyl]-3-benzyl-2,2-dimethylimidazolidin-4-one A solution of benzyl 3-benzyl-5-[(2S)-2-(dibenzylamino)-1 -hydroxy-3-phenylpropyl]-2,2-dimethyl-4-oxoimidazolidine-1-carboxylate (116 mg, 0.174 mmol) in MeOH (3 mL) under an atmosphere of nitrogen was treated with 20 wt % palladium hydroxide catalyst (24 mg, 0.174 mmol). The reaction was placed under an atmosphere of hydrogen and stirred at rt overnight. Additional 20 wt % palladium hydroxide catalyst (27.8 mg, 0.202 mmol) was added, and the reaction was stirred under an atmosphere of hydrogen at rt overnight again. The mixture was filtered through a pad of celite and washed thoroughly with MeOH. The resulting filtrate was concentrated in vacuo to afford a colorless oil which was purified by reverse phase chromatography on a C-18 column using a gradient elution of 95-5% H$_2$O (0.1% TFA)/CH$_3$CN (0.1% TFA). Collection and concentration of the appropriate fractions afforded the product as the trifluoroacetate salt. The material was partitioned between EtOAc and saturated aqueous NaHCO$_3$ solution, and the organic layer was dried over Na$_2$SO$_4$, filtered, and concentrated in vacuo to afford the product as a colorless oil in free base form. $^1$H NMR (400 MHz, CDCl$_3$) δ 7.33-7.21 (m, 10H), 4.57 (d, J=15.2 Hz, 1H), 4.33 (d, J=15.6 Hz, 1H), 3.82-3.77 (m, 2H), 3.44-3.39 (m, 1H), 3.10 (dd, J=3.6, 13.6 Hz, 1H), 2.87-2.78 (m, 3H), 2.72 (dd, J=10.0, 13.6 Hz, 1H), 1.30 (s, 3H), 1.23 (s, 3H); ES MS (M+1)=354.

Step 7:

N-[(1S)-1-Benzyl-2-(1-benzyl-2,2-ethyl-5 -oxoimidazolidin-4-yl)-2-hydroxyethyl]-N'-[(1R)-1-(4-fluorophenyl)ethyl]-5-[1-methylsulfonyl)ethyl]isophthalamide To a solution of 5-[(2S)-2-amino-1-hydroxy-3-phenylpropyl]-3-benzyl-2,2-dimethylimidazolidin-4-one (14 mg, 0.039 mmol) in DMF (200 µL) were added 3-({[(1R)-1-(4-fluorophenyl)ethyl]amino}carbonyl)-5-[methyl(methylsulfonyl)amino]benzoic acid (11 mg, 0.028 mmol) in DMF (200 µL), Hunig's base (15 µL, 0.084 mmol), and BOP (14 mg, 0.031 mmol) in DMF (250 µL). The reaction was shaken on a vortex and allowed to stand at rt for 1 h. Purification was achieved by reverse phase chromatography on a C-18 column using a gradient elution of 95-5% H$_2$O (0.1% TFA)/CH$_3$CN (0.1% TFA). Collection and lyophilization of the appropriate fractions afforded the product as a mixture of diastereomers in the form of the trifluoroacetate salts. $^1$H NMR (400 MHz, d$_6$-DMSO) δ 8.98 (d, J=7.6 Hz, 1H), 8.88 (br s, 1H), 8.21 (s, 1H), 7.98 (s, 1H), 7.90 (s, 1H), 7.44-7.41 (m, 2H), 7.32-7.25 (m, 9H), 7.17-7.13 (m, 3H), 5.17 (t, J=7.6 Hz, 1H), 4.66-4.58 (m, 1H), 4.53 (d, J=16.0 Hz, 1H), 4.41 (d, J=15.6 Hz, 1H), 4.32 (br s, 1H), 4.07 (br s, 1H), 3.26 (s, 3H), 3.16-3.14 (m, 2H), 2.99 (s, 3H), 1.46 (dd, J=6.8, 17.6 Hz, 9H); HRMS (FT-ICR) $C_{39}H_{44}FN_5O_6S+H=730.3094$; calculated 730.3069.

EXAMPLE 37

N-[(1S)-1-Benzyl-2-(1-benzyl-2,2-dimethyl-5-oxoimidazolidin-4-yl)-2-hydroxyethyl]-2-(4-butyl-2,3-dioxopiperazin-1-yl)acetamide

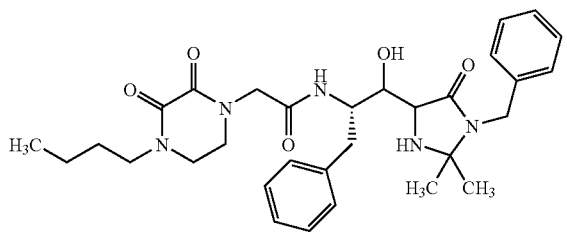

Step 1:

N-[(1S)-1-Benzyl-2-(1-benzyl-2,2-dimethyl-5-oxoimidazolidin-4-yl)-2-hydroxyethyl]-2-(4-butyl-2,3-dioxopiperazin-1-yl)acetamide The title compound was prepared using a procedure similar to that described in Example 36, Step 7, except that (4-butyl-2,3-dioxopiperazin-1-yl)acetic acid was used in place of 3-({[(1R)-1-(4-fluorophenyl)ethyl]amino}carbonyl)-5-[methyl(methylsulfonyl)amino]benzoic acid. The final product was obtained as a 5:1 mixture of diastereomers in the form of the trifluoroacetate salts. HRMS (FT-ICR) $C_{31}H_{41}N_5O_5+H=564.3180$; calculated 564.3181.

EXAMPLE 38

N'-[(1S)-1-Benzyl-2-(1-benzyl-2,2-dimethyl-5-oxoimidazolidin-4-yl)-2-hydroxyethyl]-N,N-dipropyl-isophthalamide

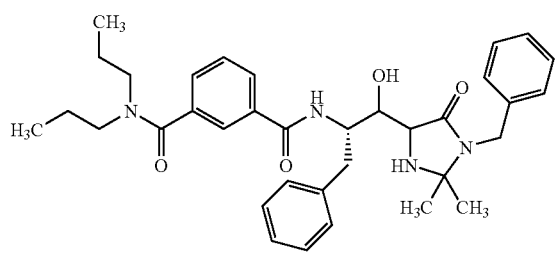

Step 1:

N'-[(1S)-1-Benzyl-2-(1-benzyl-2,2-dimethyl-5-oxoimidazolidin-4-yl)-2-hydroxyethyl]-N,N-dipropyl-isophthalamide The title compound was prepared using a procedure similar to that described in Example 36, Step 7, except that 3-[(dipropylamino)carbonyl]benzoic acid was used in place of 3-({[(1R)-1-(4-fluorophenyl)ethyl]amino}carbonyl)-5-[methyl(methylsulfonyl)amino]benzoic acid. The final product was obtained as a single diastereomer in the form of the trifluoroacetate salt. HRMS (FT-ICR) $C_{35}H_{44}N_4O_4+H=585.3429$; calculated 585.3436.

EXAMPLE 39

N-[(1S)-1-Benzyl-2-(1-benzyl-2,2-dimethyl-5-oxoimidazolidin-4-yl)-2-hydroxyethyl]benzamide

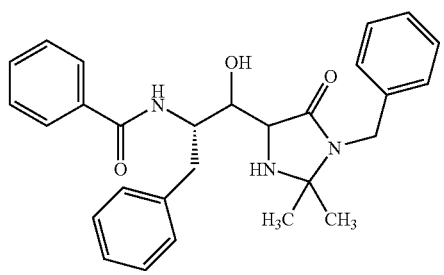

Step 1:

N-[(1S)-1-Benzyl-2-(1-benzyl-2,2-dimethyl-5-oxoimidazolidin-4-yl)-2-hydroxyethyl]benzamide The title compound was prepared using a procedure similar to that described in Example 36, Step 7, except that benzoic acid was used in place of 3-({[(1R)-1-(4-fluorophenyl)ethyl]amino}carbonyl)-5-[methyl(methylsulfonyl)amino]benzoic acid. The final product was obtained as a single diastereomer in the form of the trifluoroacetate salt. HRMS (FT-ICR) $C_{28}H_{31}N_3O_3+H=458.2421$; calculated 458.2438.

EXAMPLE 40

N-[(1S)-1-Benzyl-2-(1-benzyl-2,2-dimethyl-5-oxoimidazolidin-4-yl)-2-hydroxyethyl]-2-phenylacetamide

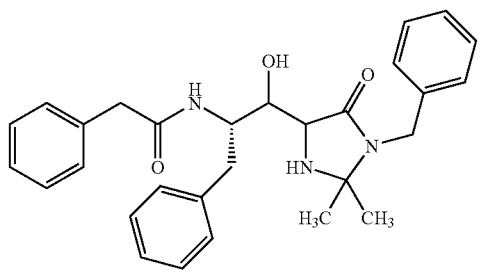

Step 1:

N-[(1S)-1-Benzyl-2-(1-benzyl-2,2-dimethyl-5-oxoimidazolidin-4-yl)-2-hydroxyethyl]-2-phenylacetamide The title compound was prepared using a procedure similar to that described in Example 36, Step 7, except that phenylacetic acid was used in place of 3-({[(1R)-1-(4-fluorophenyl)ethyl]amino}carbonyl)-5-[methyl(methylsulfonyl)amino]benzoic acid. The final product was obtained as a single diastereomer in the form of the trifluoroacetate salt. HRMS (FT-ICR) $C_{29}H_{33}N_3O_3+H=472.2563$; calculated 472.2595.

EXAMPLE 41 tert-Butyl [(1S)-1-benzyl-2-(1-benzyl-2,2-dimethyl-5-oxoimidazolidin-4-yl)-2-hydroxyethyl]carbamate

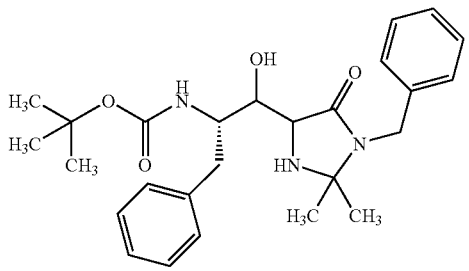

Step 1:

tert-Butyl [(1S)-1-benzyl-2-(1-benzyl-2,2-dimethyl-5-oxoimidazolidin-4-yl)-2-hydroxyethyl]carbamate The title compound was prepared using a procedure similar to that described in Example 36, Step 7, except that di-tert-butyl dicarbonate was used in place of 3-({[(1R)-1-(4-fluorophenyl)ethyl]amino}carbonyl)-5-[methyl(methylsulfonyl)amino]benzoic acid, and triethylamine was used in place of Hunig's base. BOP reagent was omitted. The final product was obtained as a single diastereomer in the form of the trifluoroacetate salt. HRMS (FT-ICR) $C_{26}H_{35}N_3O_4+H=454.2701$; calculated 454.2701.

EXAMPLE 42

Phenyl [(1S)-1-benzyl-2-(1-benzyl-2,2-dimethyl-5-oxoimidazolidin-4-yl)-2-hydroxyethyl]carbamate

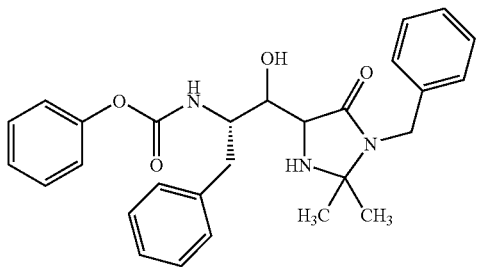

Step 1:

Phenyl [(1S)-1-benzyl-2-(1-benzyl-2,2-dimethyl-5-oxoimidazolidin-4-yl)-2-hydroxyethyl]carbamate The title compound was prepared using a procedure similar to that described in Example 36, Step 7, except that phenyl-chloroformate was used in place of 3-({[(1R)-1-(4-fluorophenyl)ethyl]amino}carbonyl)-5-[methyl(methylsulfonyl)amino]benzoic acid, and triethylamine was used in place of Hunig's base. $CH_2Cl_2$ was used as the solvent, and BOP reagent was omitted. The final product was obtained as a 9:1 mixture of diastereomers in the form of the trifluoroacetate salts. HRMS (FT-ICR) $C_{28}H_{31}N_3O_4+H=474.2367$; calculated 474.2385.

EXAMPLE 43

N-[(1S)-1-benzyl-2-(1-benzyl-2,2-dimethyl-5-oxoimidazolidin-4-yl)-2-hydroxyethyl]acetamide

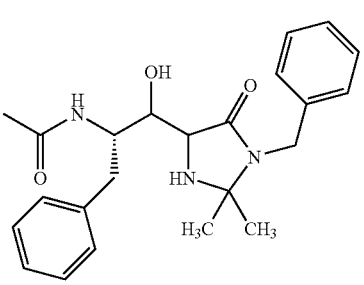

Step 1:

N-[(1S)-1-benzyl-2-(1-benzyl-2,2-dimethyl-5-oxoimidazolidin-4-yl)-2-hydroxyethyl]acetamide The title compound was prepared using a procedure similar to that described in Example 36, Step 7, except that acetyl chloride was used in place of 3-{[(1R)-1-(4-fluorophenyl)ethyl]amino}carbonyl)-5-[methyl(methylsulfonyl)amino]benzoic acid, and triethylamine was used in place of Hunig's base. $CH_2Cl_2$ was used as the solvent, and BOP reagent was omitted. HRMS (FT-ICR) $C_{23}H_{29}N_3O_3+H=396.2282$; calculated 396.2274.

EXAMPLE 44 tert-Butyl [(1S)-1-benzyl-2-(1-benzyl-2-methyl-5-oxoimidazolidin-4-yl)-2-hydroxyethyl]carbamate

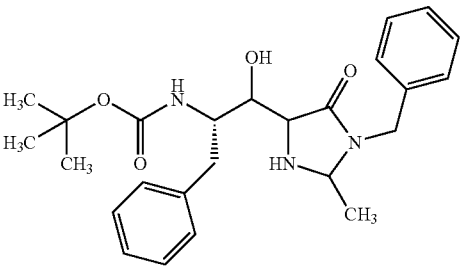

Step 1:

3-Benzyl-2-methylimidazolidin-4-one

The compound was prepared using a procedure similar to that described in Example 36, Step 3, except that acetaldehyde was used in place of acetone and the reaction was heated to reflux for 2 days. The crude material was treated with $CH_2Cl_2$, and the resulting precipitate was filtered to afford a white material which was purified as stated. The product was obtained as a yellow oil. ES MS (M+1)=191.

Step 2:

(+/−) Benzyl 3-benzyl-2-methyl-4-oxoimidazolidine-1-carboxylate

The compound was prepared using a procedure similar to that described in Example 36, Step 4, except that purification was achieved by flash column chromatography on silica gel using a gradient elution of 0-50% EtOAc/hexanes. Collection and concentration of the appropriate fractions afforded the mixture of diastereomers as a colorless oil. The isomers were separated by chiral chromatography on a ChiralPak AS column using an isocratic elution of MeOH. The earlier and later eluting enantiomers demonstrated (+) and (−) rotation, respectively. (+) Enantiomer: ES MS (M+1)=325; (−) Enantiomer: ES MS (M+1)=325.

Step 3:

Benzyl 3-benzyl-5-[(2S)-2-(dibenzylamino)-1-hydroxy-3-phenylpropyl]-2-methyl-4-oxoimidazolidine-1-carboxylate Diastereomers of the compound were separately prepared via a procedure similar to that described in Example 36, Step 5 using the (+) and (−) enantiomers of benzyl 3-benzyl-2-methyl-4-oxoimidazolidine-1-carboxylate. Diastereomer from (+) enantiomer of the oxoimidazolidine: ES MS (M+1)=654; Diastereomer from (−) enantiomer of the oxoimidazolidine: ES MS (M+1)=654.

Step 4:

5-[(2S)-2-Amino-1-hydroxy-3-phenylpropyl]-3-benzyl-2-methylimidazolidin-4-one

Diastereomers of the compound were separately prepared using a procedure similar to that described in Example 36, Step 6, except that purification was achieved by treating the crude materials with $CH_2Cl_2$ and collecting the resulting white precipitates by filtration to afford the products as a white solids. Diastereomer originating from (+) enantiomer of the oxoimidazolidine: ES MS (M+1)=340; Diastereomer originating from (−) enantiomer of the oxoimidazolidine: ES MS (M+1)=340.

Step 5:

tert-Butyl (1S)-1-benzyl-2-(1-benzyl-2-methyl-5-oxoimidazolidin-4-yl)-2-hydroxyethylcarbamate Diastereomers of the compound were separately prepared using a procedure similar to that described in Example 36, Step 7, except that di-tert-butyl dicarbonate was used in place of 3-({[(1R)-1-(4-fluorophenyl)ethyl]amino}carbonyl)-5-[methyl(methylsulfonyl)amino]benzoic acid and triethylamine was used in place of Hunig's base. BOP reagent was omitted. The final products were obtained as single diastereomers in the form of trifluoroacetate salts. Diastereomer originating from (+) enantiomer of the oxoimidazolidine: HRMS (FT-ICR) $C_{25}H_{33}N_3O_4$+H=440.2552; calculated 440.2544; Diastereomer originating from the (−) enantiomer of the oxoimidazolidine: HRMS (FT-ICR) $C_{25}H_{33}N_3O_4$+H=440.2526; calculated 440.2544.

EXAMPLE 45

N-[(1S)-1-Benzyl-2-(1-benzyl-2-methyl-5-oxoimidazolidin-4-yl)-2-hydroxyethyl]-N'-[(1R)-1-(4-fluorophenyl)ethyl]-5-[methyl(methylsulfonyl)amino] isophthalamide

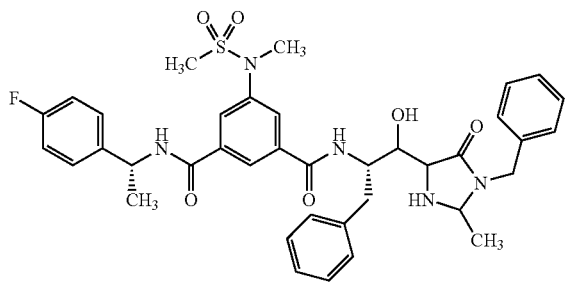

Step 1:

N-[(1S)-1-Benzyl-2-(1-benzyl-2-methyl-5-oxoimidazolidin-4-yl)-2-hydroxyethyl]-N'-[(1R)-1-(4-fluorophenyl)ethyl]-5-[methyl(methylsulfonyl)amino] isophthalamide The title compound was prepared using a procedure similar to that described in Example 36, Step 7. The diastereomer of 5-[(2S)-2-amino-1-hydroxy-3-phenylpropyl]-3-benzyl-2-methylimidazolidin-4-one which originated from (−)-benzyl 3-benzyl-2-methyl-4-oxoimidazolidine-1-carboxylate was used as the starting material. The final product was obtained as a single diastereomer in the form of the trifluoroacetate salt. HRMS (FT-ICR) $C_{38}H_{42}N_5O_6S$+H=716.2928; calculated 716.2913.

EXAMPLE 46

Phenyl [(1S)-1-benzyl-2-(1-benzyl-2-methyl-5-oxoimidazolidin-4-yl)-2-hydroxyethyl]carbamate

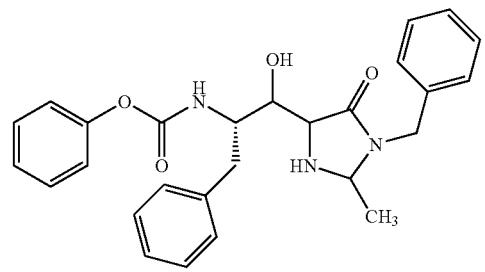

Step 1:

Phenyl [(1S)-1-benzyl-2-(1-benzyl-2-methyl-5-oxoimidazolidin-4-yl)-2-hydroxyethyl]carbamate Diastereomers of the title compound were separately prepared using a procedure similar to that described in Example 36, Step 7, except that phenylchloroformate was used in place of 3-({[(1R)-1-(4-fluorophenyl)ethyl]amino}carbonyl)-5-[methyl(methylsulfonyl)amino]benzoic acid and triethylamine was used in place of Hunig's base. BOP reagent was omitted. The diastereomers of 5-[(2S)-2-amino-1-hydroxy-3-phenylpropyl]-3-benzyl-2-methylimidazolidin-4-one which originated from the (+) and (−) enantiomers of benzyl 3-benzyl-2-methyl-4-oxoimidazolidine-1-carboxylate were used as the starting materials for the separate reactions. The final products were obtained as single diastereomers in the form of trifluoroacetate salts. Diastereomer originating from the (+) enantiomer of the oxoimidazolidine: HRMS (FT-ICR) $C_{27}H_{29}N_3O_4+H=460.2226$; calculated 460.2231; Diastereomer originating from the (−) enantiomer of the oxoimidazolidine: HRMS (FT-ICR) $C_{27}H_{29}N_3O_4+H=460.2217$; calculated 460.2231.

EXAMPLE 47

N-{(1S,2)-1-Benzyl-2-hydroxy-2-[(4S)-1,2,2-trimethyl-5-oxoimidazolidin-4-yl]ethyl}-N'-[(1R)-1-(4-fluorophenyl)ethyl]-5-[methyl(methylsulfonyl)amino]isophthalamide

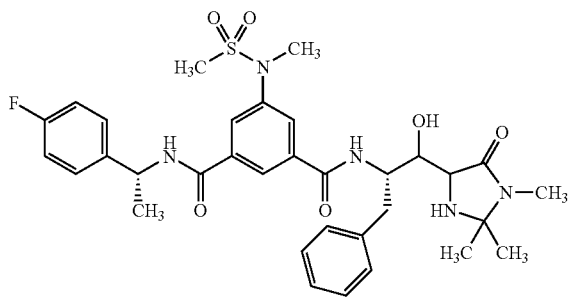

Step 1:

N-Benzyl-N-tert-butoxycarbonyl)glycine

To a solution of N-benzylglycine hydrochloride (5.00 g, 24.80 mmol) in dioxane (100 mL) and water (25 mL) were added di-tert-butyldicarbonate (5.95 g, 27.28 mmol) and aqueous 1N NaOH solution (50 mL), and the reaction was stirred at rt overnight. The solvents were removed in vacuo, and the resulting residue was partitioned between EtOAc and aqueous 10% $KHSO_4$ solution. The layers were separated and the aqueous was extracted twice more with EtOAc. The combined organic layers were washed with brine, dried over $Na_2SO_4$, filtered, and concentrated in vacuo to afford the product as a white solid. $^1H$ NMR (400 MHz, $CDCl_3$) δ 7.36-7.22 (m, 5H), 4.53 (d, J=14.4 Hz, 2H), 3.96 (s, 1H), 3.83 (s, 1H), 1.48 (s, 9H); ES MS [M-100 (loss of BOC)+1]=166.

Step 2:

$N^2$-benzyl-$N^2$-(tert-butoxycarbonyl)-$N^1$-methylglycinamide

The compound was prepared using a procedure similar to that described in Example 36, Step 1, except that 2.0M methylamine in MeOH was used in place of benzylamine. ES MS [M-100 (loss of BOC)+1]=179.

Step 3:

$N^2$-benzyl-$N^1$-methylglycinamide

The compound was prepared using a procedure similar to that described in Example 36, Step 2, except that the procedure was executed only twice. The solvent was removed in vacuo without filtering to afford the product as a white solid it the form of the hydrochloride salt. ES MS (M+1)=179.

Step 4:

1-Benzyl-2,2,3-trimethylimidazolidin-4-one

The compound was prepared using a procedure similar to that described in Example 36, Step 3. The crude material was suspended in $CH_2Cl_2$ and filtered. The resulting filtrate was concentrated in vacuo to afford the product as a light yellow oil. ES MS (M+1)=219.

Step 5:

(5S)-1-Benzyl-5-[(1S,2S)-2-(dibenzylamino)-1-hydroxy-3-phenylpropyl]-2,2,3-trimethylimidazolidin-4-one and 1-Benzyl-5-[(2S)-2-(dibenzylamino)-1-hydroxy-3-phenylpropyl]-2,2,3-trimethylimidazolidin-4-one The compound was prepared using a procedure similar to that described in Example 36, Step 5, except that lithium diisopropylamine was prepared from diisopropylamine and 2.5M n-butyl lithium in hexanes at −78° C. over 10 min in place of using the commercially available reagent. Once all reagents were added to the reaction, the mixture was stirred for 1 h at −78° C. and then 10 min at 0° C. The reaction was partitioned between saturated aqueous $NaHCO_3$ solution and EtOAc. The layers were separated, and the aqueous was extracted into EtOAc twice more. The combined organic layers were washed with brine, dried over $Na_2SO_4$, filtered, and concentrated in vacuo to afford a yellow oil. The crude material was purified by flash column chromatography on silica gel using a gradient elution of 0-60% EtOAc/hexanes. Collection and concentration of the appropriate fractions afforded a mixture of products. Further separation was achieved by reverse phase chromatography on a C-18 column using a gradient elution of 45-25% $H_2O$ (0.1% TFA)/$CH_3CN$ (0.1% TFA). Collection and concentration of the appropriate fractions afforded two products as single diastereomers in the form of trifluoroacetate salts. The earlier eluting diastereomer was determined to have the S,S,S configuration and was converted to the free base by partitioning the material between EtOAc and saturated aqueous $NaHCO_3$ solution. The organic layer was dried over $Na_2SO_4$, filtered, and concentrated in vacuo to afford the earlier eluting diastereomer as a yellow oil. The configuration of the later eluting diastereomer was not determined, and the material was allowed to remain in the salt form Earlier eluting (S,S,S) diastereomer: ES MS (M+1)=548; Later eluting diastereomer: ES MS (M+1)=548.

Step 6:

(5S)-5-[(1S,2S)-2-Amino-1-hydroxy-3-phenylpropyl]-2,2,3-trimethylimidazolidin-4-one and 5-[(2S)-2-Amino-1-hydroxy-3-phenylpropyl]-2,2,3-trimethylimidazolidin-4-one The title compound was prepared using a procedure similar to that described in Example 36, Step 6 from the (S,S,S)

diastereomer from Step 5. Purification by reverse phase chromatography was unnecessary: ES MS (M+1)=278;

Step 7:

N-{(1S,2S)-1-Benzyl-2-hydroxy-2-[(4S)-1,2,2-trimethyl-5-oxoimidazolidin-4-yl]ethyl}-N'-[(1R)-1-(4-fluorophenyl)ethyl]-5-[methyl(methylsulfonyl)amino]isophthalamide The title compound was prepared using a procedure similar to that described in Example 36, Step 7 isolated as a trifluoroacetate salt: HRMS (PT-ICR) $C_{33}H_{40}FN_5O_6S$+H=654.2730; calculated 654.2756;

EXAMPLE 48

5N-[(1S)-1-benzyl-2-hydroxy-2-(1,2,2-trimethyl-5-oxoimidazolidin-4-yl]ethyl]-N'-[(1R)-1-(4-fluorophenyl)ethyl]-5-[methyl(methylsulfonyl)amino]isophthalamide The title compound was prepared from the other, unassigned, diastereomer from Example 46, step 5 in the same manner as for Example 46, steps 6 and 7, and isolated as its trifluoroacetate salt. HRMS (FT-ICR) $C_{33}H_{40}FN_5O_6S$+H=654.2742; calculated 654.2756.

EXAMPLE 49

N-[(1S)-1-benzyl-2-(1-benzyl-2,2-dimethyl-5-oxoimidazolidin-4-yl)-2-hydroxyethyl]-2-chloro-6-(methyl{[(1S,2S)-2-methylcyclopropyl]methyl}amino)isonicotinamide

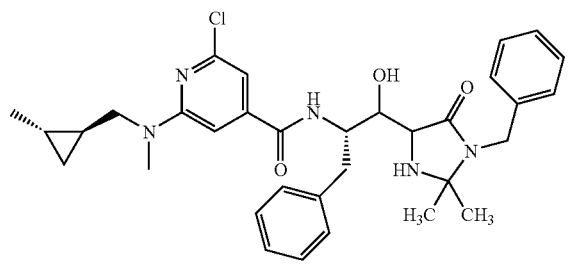

Step 1:

N-[(1S)-1-benzyl-2-(1-benzyl-2,2-dimethyl-5-oxoimidazolidin-4-yl)-2-hydroxyethyl]-2-chloro-6-(methyl{[(1S,2S)-2-methylcyclopropyl]methyl}amino)isonicotinamide The title compound was prepared using a procedure similar to that described in Example 36, step 7, except that 2-chloro-6-methyl {[(1S,2S)-2-methylcyclopropyl]methyl}amino) isonicotinic acid was used in place of 3-({[(1R)-1-(4-fluorophenyl)ethyl]amino}carbonyl)-5-[methyl(methylsulfonyl)amino]benzoic acid. The final product was obtained as a single diastereomer in the form of the trifluoroacetate salt. HRMS (FT-ICR) $C_{33}H_{40}ClN_5O_3$+H=590.2901; calculated 590.2893.

EXAMPLE 50

N-[(1S)-1-benzyl-2-(1-benzyl-2,2-dimethyl-5-oxoimidazolidin-4-yl)-2-hydroxyethyl]-2-(methyl{[(1S,2S)-2-methylcyclopropyl]methyl}amino)-6-[methyl(methylsulfonyl)amino]isonicotinamide

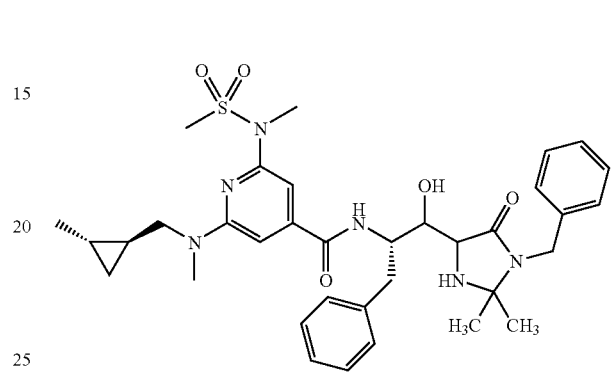

Step 1:

N-[(1S)-1-benzyl-2-(1-benzyl-2,2-dimethyl-5-oxoimidazolidin-4-yl)-2-hydroxyethyl]-2-(methyl{[(1S,2S)-2-methylcyclopropyl]methyl}amino)-6-[methyl(methylsulfonyl)amino]isonicotinamide The title compound was prepared using a procedure similar to that described in Example 36, step 7, except that 2-(methyl{[(1S,2S)-2-methylcyclopropyl]methyl}amino)-6-[methyl(methylsulfonyl)amino]isonicotinic acid was used in place of 3-{[(1R)-1-(4-fluorophenyl)ethyl]amino}carbonyl)-5-[methyl(methylsulfonyl)amino]benzoic acid. The final product was obtained as a single diastereomer in the form of the trifluoroacetate salt. HRMS (FT-ICR) $C_{33}H_{40}ClN_5O_3$+H=663.3322; calculated 663.3323.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (I):

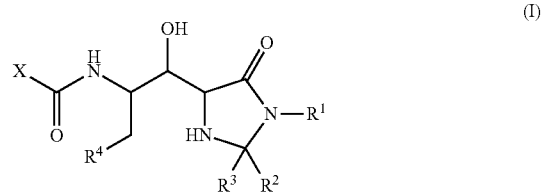

wherein $R^1$, $R^2$, $R^3$ and $R^4$ are independently selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{6-10}$ aryl, or
(6) heteroaryl,
wherein said alkyl, alkenyl, alkynyl, aryl or heteroaryl is optionally substituted with one or more
(a) halo,
(b) —$C_{1-10}$ alkyl, wherein said alkyl is optionally substituted with one or more fluoro,
(c) —$C_{3-12}$ cycloalkyl,
(d) —OH,
(e) —CN,
(f) —O—$C_{1-10}$ alkyl, wherein said alkyl is optionally substituted with one or more fluoro,
(g) —$C_{6-10}$ aryl, or
(h) heteroaryl,
and said aryl and heteroaryl is optionally substituted with one or more
(i) halo,
(ii) —OH,
(iii) —CN,
(iv) -$Q^1$-$C_{1-10}$ alkyl, wherein said alkyl is optionally substituted with one or more fluoro,
(v) —$C_{1-10}$ alkyl, wherein said alkyl is optionally substituted with one or more fluoro, or
(vi) —$C_{3-12}$ cycloalkyl,
and $Q^1$ is selected from the group consisting of
(A) —O—,
(B) —$SO_2$—,
(C) —NH—,
or $R^2$ and $R^3$ are linked together to form a 3-7 carbocyclic ring structure, wherein one, two or three of the ring carbon atoms may be replaced with O, S, NH, —C(=O)— or $SO_2$, and the carbocyclic ring is optionally substituted with one or more
(a) —$C_{1-10}$ alkyl,
(b) —$C_{2-10}$ alkenyl,
(c) —$C_{2-10}$ alkynyl, and
(d) —$C_{6-10}$ aryl;
X is selected from the group consisting of
(1)-$(Q^2)_n$-$R^5$,
wherein $Q^2$ is selected from the group consisting of
(a) —$CH_2$—, and
(b) —O—,
$R^5$ is selected from the group consisting of
(a) hydrogen
(b) —$C_{1-10}$ alkyl,
(c) —$C_{2-10}$ alkenyl,
(d) —$C_{2-10}$ alkynyl, and
(e) —$C_{6-10}$ aryl,
wherein said alkyl, alkenyl, alkynyl or aryl is optionally substituted with one or more
(i) halo,
(ii) —$C_{1-10}$ alkyl, wherein said alkyl is optionally substituted with one or more fluoro,
(iii) —$C_{3-12}$ cycloalkyl,
(iv) —OH,
(v) —CN,
(vi) —O—$C_{1-10}$ alkyl, wherein said alkyl is optionally substituted with one or more fluoro, or
(vii) —$C_{6-10}$ aryl; and

2)

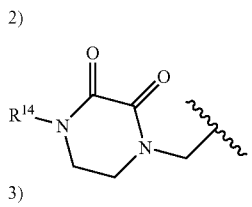

3)

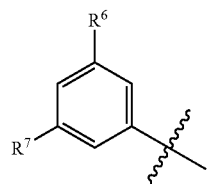

wherein $R^6$ is selected from the group consisting of
(a) ($R^8$—$SO_2$)N($R^9$)—, wherein $R^8$ is selected from the group consisting of
(i) —$C_{1-10}$ alkyl,
(ii) —$C_{2-10}$ alkenyl,
(iii) —$C_{2-10}$ alkynyl,
(iv) —$C_{3-8}$ cycloalkyl, or
(v) —$C_{6-10}$ aryl
wherein said alkyl, alkenyl, alkynyl, cycloalkyl and aryl is optionally substituted with one or more
(A) halo,
(B) —OH,
(C) —CN,
(D) —O—$C_{1-10}$ alkyl,
(E) —$C_{1-10}$ alkyl,
(F) —$C_{2-10}$ alkenyl,
(G) —$C_{2-10}$ alkynyl,
(H) —$C_{3-8}$ cycloalkyl,
(I) —$C_{6-10}$ aryl, or
(J) heteroaryl,
and said aryl and heteroaryl is optionally substituted with one or more
(I) halo,
(II) —OH,
(III) —CN,
(IV) —O—$C_{1-10}$ alkyl,
(V) —$C_{3-8}$ cycloalkyl,
(VI) —$C_{1-10}$ alkyl,
(VII) —$C_{2-10}$ alkenyl, or
(VIII) —$C_{2-10}$ alkynyl;
$R^9$ is selected from the group consisting of
(i) hydrogen,
(ii) —$C_{1-10}$ alkyl,
(iii) —$C_{2-10}$ alkenyl,
(iv) —$C_{2-10}$ alkynyl, or
(v) —$C_{6-10}$ aryl,
wherein said alkyl, alkenyl, alkynyl or aryl is optionally substituted with one or more
(A) halo,
(B) —OH,
(C) —CN,
(D) —O—$C_{1-10}$ alkyl,
(E) —$C_{3-8}$ cycloalkyl,
(F) —$C_{6-10}$ aryl, or
(G) heteroaryl,
wherein said cycloalkyl, aryl or heteroaryl is optionally substituted with one or more
(I) halo,
(II) —OH, (III) —CN,
(IV) —O—$C_{1-10}$ alkyl,
(V) —$C_{3-8}$ cycloalkyl, or
(VI) —$C_{6-10}$ aryl;

(b)

(b)
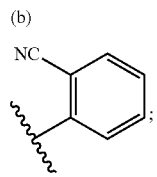;

(c)

(c)
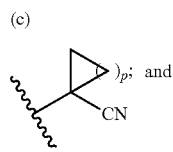; and and $R^7$ is selected from the group consisting of (a)
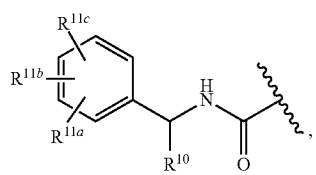, (b)
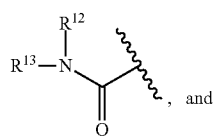, and wherein $R^{10}$ is $C_{1-10}$ alkyl, wherein said alkyl is unsubstituted or substituted with one or more halogen;
$R^{11a}$, $R^{11b}$, and $R^{11c}$ are independently selected from the group consisting of:
(i) hydrogen,
(ii) halo,
(iii) —$C_{1-10}$ alkyl,
(iv) —OH,
(v) —CN,
(vi) —$C_{3-12}$ cycloalkyl, and
(vii) —O—$C_{1-10}$ alkyl;
$R^{12}$ and $R^{13}$ are independently selected from the group consisting of
(i) hydrogen,
(ii) —$C_{1-10}$ alkyl,
(iii) —$C_{2-10}$ alkenyl,
(iv) —$C_{2-10}$ alkynyl, and
(v) —$C_{1-10}$ alkyl-$C_{3-12}$ cycloalkyl;
wherein said alkyl, alkenyl, alkynyl and cycloalkyl is optionally substituted with one or more
(A) halo,
(B) —OH,
(C) —CN,
(D) —$C_{1-10}$ alkyl,
(E) —O—$C_{1-10}$ alkyl,
(F) —$C_{3-8}$ cycloalkyl,
(G) —$NR^aR^b$, wherein $R^a$ and $R^b$ are selected from the group consisting of
(i) hydrogen, and
(ii) —$C_{1-10}$ alkyl, or $R^a$ and $R^b$ are joined together with the nitrogen atom to which they are attached to form a 4-6 membered carbocyclic ring having a single nitrogen, or
(H) —$C_{6-10}$ aryl;
or $R^{12}$ and $R^{13}$ are joined together with the nitrogen atom to which they are attached to form a 4-6 membered carbocyclic ring having a single nitrogen, wherein said carbocyclic ring is optionally substituted with one or more
(1) —$C_{1-10}$ alkyl, wherein said alkyl is optionally substituted with one or more
(i) halogen,
(ii) hydroxy, or
(iii) —$C_{1-6}$ alkoxy;
(2) —$C_{3-12}$ cycloalkyl,
(3) $(CH_2)_m$-phenyl, wherein said phenyl is unsubstituted or substituted with one or more halogen,
(4) $C_{2-10}$ alkenyl,
(5) $C_{2-10}$ alkynyl,
(6) —CN,
and said alkyl, alkenyl or alkynyl R12 and $R^{13}$ groups are optionally substituted with one or more
(a) halo,
(b) —OH,
(c) —CN,
(d) —O—$C_{1-10}$ alkyl, or
(e) —$C_{3-12}$ cycloalkyl;
and said cycloalkyl and phenyl $R^{12}$ and $R^{13}$ groups are optionally substituted with one or more
(a) halo,
(b) —$C_{1-10}$ alkyl,
(c) OH,
(d) —CN,
(e) —$C_{3-12}$ cycloalkyl, or
(f) —O—$C_{1-10}$ alkyl;
$R^{14}$ is selected from the group consisting of
(i) hydrogen,
(ii) —$C_{1-10}$ alkyl;
(iii) halo,
(iv) —$C_{3-12}$ cycloalkyl,
(v) —$C_{6-10}$ aryl, and
(vi) heteroaryl,
wherein said aryl and heteroaryl is optionally substituted with one or more
(A) halo,
(B) —OH,
(C) —CN,
(D) —O—$C_{1-10}$ alkyl,
(E) —$C_{3-8}$ cycloalkyl, or
(F) —$C_{1-10}$ alkyl;

4)

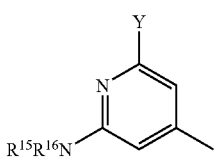

wherein Y is $R^6$ or halogen,
and $R^{15}$ and $R^{16}$ are independently selected from the group consisting of
(1) hydrogen,
(2) —$C_{1-10}$ alkyl,
(3) —$C_{2-10}$ alkenyl,
(4) —$C_{2-10}$ alkynyl, and
(5) —$C_{1-10}$ alkylene-$C_{3-12}$ cycloalkyl;
wherein said alkyl, cycloalkyl, alkenyl or alkynyl is unsubstituted or substituted with one or more
  (a) halo,
  (b) —OH,
  (c) —CN,
  (d) —$C_{1-10}$ alkyl
  (e) —$C_{3-12}$ cycloalkyl,
  (f) —O—$C_{1-10}$ alkyl,
  (g) heteroaryl, wherein said heteroaryl may be unsubstituted or substituted with halogen;
  (h) phenyl, or
  (i) —$NR^cR^d$,
  (I) hydrogen, and
  (II) —$C_{1-10}$ alkyl, or $R^c$ and $R^d$ are joined together with the nitrogen atom to which they are attached to form a 4-6 membered carbocyclic ring having a single nitrogen,
or $R^{15}$ and $R^{16}$ are joined together with the nitrogen atom to which they are attached to form a 4-6 membered carbocyclic ring having a single nitorgen, wherein said carbocyclic ring is unsubstituted or substituted with one or more
  (a) —$C_{1-10}$ alkyl,
  (b) —$C_{3-12}$ cycloalkyl,
  (c) —$(CH_2)_n$-phenyl,
  (d) —$C_{2-10}$ alkenyl, or
  (e) —$C_{2-10}$ alkynyl,
  wherein said alkyl, alkenyl and alkynyl is unsubstituted or substituted with one or more
    (i) halo,
    (ii) —OH,
    (iii) —CN,
    (iv) —O—$C_{1-10}$ alkyl, or
    (v) —$C_{3-12}$ cycloalkyl;
  and said cycloalkyl and phenyl is unsubstituted or substituted with one or more
    (i) halo,
    (ii) —$C_{1-10}$ alkyl,
    (iii) —OH,
    (iv) —CN,
    (v) —$C_{3-12}$ cycloalkyl, or
    (vi) —O—$C_{1-10}$ alkyl;
m is 0, 1, 2, 3 or 4;
n is 0 or 1; and
p is 1, 2, 3 or 4;
or a pharmaceutically acceptable salt thereof, and individual enantiomers and diastereomers thereof.

2. A compound of claim 1, or a pharmaceutically acceptable salt thereof, wherein $R^1$ is selected from the group consisting of $C_{1-10}$ alkyl, wherein the alkyl is optionally substituted with one or more
(a) halo,
(b) —$C_{1-10}$ alkyl,
(c) —O—$C_{1-10}$ alkyl,
(d) —$C_{6-10}$ aryl, or
(e) heteroaryl,
and said aryl or heteroaryl is optionally substituted with one or more
(i) halo,
(ii) —OH,
(iii) —CN,
(iv) -$Q^1$-$C_{1-10}$ alkyl, wherein said alkyl is optionally substituted with one or more fluoro, or
(v) —$C_{1-10}$ alkyl, wherein said alkyl is optionally substituted with one or more fluoro,
and Q1 is selected from the group consisting of
(A) —O—, or
(B) —$SO_2$—.

3. A compound of claim 1, or a pharmaceutically acceptable salt thereof, wherein $R^2$ is hydrogen, and $R^3$ is $C_{1-10}$ alkyl or $C_{6-10}$ aryl.

4. A compound of claim 1, or a pharmaceutically acceptable salt thereof, wherein $R^2$ and $R^3$ are each $C_{1-10}$ alkyl.

5. A compound of any of claim 1, or a pharmaceutically acceptable salt thereof, wherein $R^2$ and $R^3$ are linked together to form a 3-7 carbocyclic ring structure, wherein one, two or three of the ring carbon atoms may be replaced with O, S, NH, —C(=O)— or $SO_2$, and the carbocyclic ring is optionally substituted with $C_{1-10}$ alkyl.

6. A compound of claim 1, or a pharmaceutically acceptable salt thereof, wherein $R^4$ is selected from the group consisting of
(1)—$C_{1-10}$ alkyl,
(2) phenyl, and
(3) heteroaryl,
wherein said alkyl, phenyl or heteroaryl are optionally substituted with one or more
(i) halo,
(ii) —OH,
(iii) —CN,
(iv) -$Q^1$-$C_{1-10}$ alkyl,
(v) —$C_{1-10}$ alkyl, or
(vi) —$C_{3-12}$ cycloalkyl.

7. A compound of claim 6, or a pharmaceutically acceptable salt thereof, wherein $R^4$ is phenyl.

8. A compound of claim 1 or a pharmaceutically acceptable salt thereof, wherein X is

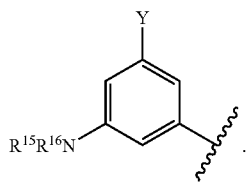

9. The compound of claim 8 or a pharmaceutically acceptable salt thereof, wherein $R^{15}$ is $C_{1-6}$ alkyl and $R^{16}$ is $C_{1-6}$ alkyl-$C_{3-12}$ cycloalkyl.

10. A compound of claim 1, which is a compound of formula II

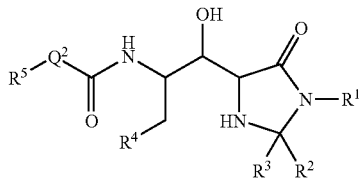

or a pharmaceutically acceptable salt thereof, and individual enantiomers and diasteromers thereof.

11. A compound of claim 10, or a pharmaceutically acceptable salt thereof, wherein $Q^2$ is —O— and $R^5$ is $C_{1-10}$ alkyl, wherein said alkyl is optionally substituted with one or more
   (i) halo,
   (ii) —$C_{1-10}$ alkyl, or
   (vii) —$C_{6-10}$ aryl.

12. A compound of claim 1, or a pharmaceutically acceptable salt thereof, which is a compound of formula (III):

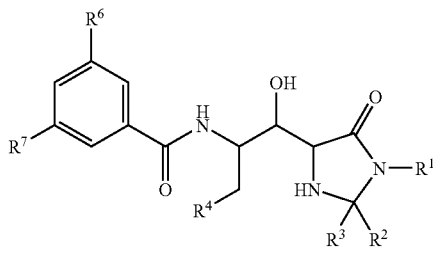

or a pharmaceutically acceptable salt thereof, and individual enantiomers and diastereomers thereof.

13. A compound of claim 12, or a pharmaceutically acceptable salt thereof, wherein $R^6$ is $(R^8—SO_2)N(R^9)$—.

14. A compound of which is selected from the group consisting of:
   tert-Butyl (1S,2R)-1-benzyl-2-hydroxy-2-[(4S)-2-isopropyl-1-(1-methylbutyl)-5-oxoimidazolidin-4-yl]ethylcarbamic acid;
   tert-Butyl (1S,2R)-1-benzyl-2-hydroxy-2-[(4S)-1-isopentyl-2-isopropyl-5-oxoimidazolidin-4-yl]ethylcarbamic acid;
   tert-Butyl (1S,2R)-1-benzyl-2-hydroxy-2-{(4S)-2-isopropyl-5-oxo-1-[3-(trifluoromethyl)benzyl]imidazolidin-4-yl}ethylcarbamic acid;
   tert-Butyl (1S,2R)-1-benzyl-2-hydroxy-2-[(4S)-2-isopropyl-5-oxo-1-(2-phenylethyl)imidazolidin-4-yl]ethylcarbamic acid;
   tert-Butyl {(1S,2R)-1-benzyl-2-hydroxy-2-[(4S)-2-isopropyl-5-oxo-1-pentylimidazolidin-4-yl]ethyl}carbamic acid;
   [(1S,2R)-2-Hydroxy-2-[(4S)-1-[2-(1-methylethoxy)ethyl]-2-(1-methylethyl)-5-oxo-4-imidazolidinyl]-1-(phenylmethyl)ethyl]-, 1,1-dimethylethyl ester carbamic acid;
   tert-Butyl {(1S,2R)-1-benzyl-2-hydroxy-2-[(4S)-2-isopropyl-1-(2-methoxyethyl)-5-oxoimidazolidin-4-yl]ethyl}carbamic acid;
   tert-Butyl ((1S,2R)-1-benzyl-2-hydroxy-2-{(4S)-2-isopropyl-5-oxo-1-[2-(trifluoromethyl)benzyl]imidazolidin-4-yl}ethyl)carbamic acid;
   tert-Butyl ((1S,2R)-1-benzyl-2-hydroxy-2-{(4S)-2-isopropyl-5-oxo-1-[(1S)-1-phenylethyl]imidazolidin-4-yl}ethyl)carbamic acid;
   tert-Butyl {(1S,2R)-1-benzyl-2-hydroxy-2-[(4S)-2-isopropyl-5-oxo-1-(pyridin-2-ylmethyl)imidazolidin-4-yl]ethyl}carbamic acid;
   tert-Butyl {(1S,2R)-1-benzyl-2-hydroxy-2-[(4S)-2-isopropyl-5-oxo-1-(pyridin-3-ylmethyl)imidazolidin-4-yl]ethyl}carbamic acid;
   tert-Butyl {(1S,2R)-1-benzyl-2-hydroxy-2-[(4S)-2-isopropyl-5-oxo-1-(pyridin-4-ylmethyl)imidazolidin-4-yl]ethyl}carbamic acid;
   tert-Butyl ((1S,2R)-1-benzyl-2-{(4S)-1-[(1R)-1,5-dimethylhexyl]-2-isopropyl-5-oxoimidazolidin-4-yl}-2-hydroxyethyl)carbamic acid;
   tert-Butyl ((1S,2R)-1-benzyl-2-{(4S)-1-[(1S)-1,5-dimethylhexyl]-2-isopropyl-5-oxoimidazolidin-4-yl}-2-hydroxyethyl)carbamic acid;
   tert-Butyl ((1S,2R)-1-benzyl-2-hydroxy-2-{(4S)-2-isopropyl-1-[4-(methylsulfonyl)benzyl]-5-oxoimidazolidin-4-yl}ethyl)carbamic acid;
   tert-Butyl ((1S,2R)-2-{(4S)-1-[2-(1,3-benzodioxol-5-yl)ethyl]-2-isopropyl-5-oxoimidazolidin-4-yl}-1-benzyl-2-hydroxyethyl)carbamic acid;
   tert-Butyl {(1S,2R)-1-benzyl-2-hydroxy-2-[(4S)-2-isopropyl-5-oxo-1-(1-propylbutyl)imidazolidin-4-yl]ethyl}carbamic acid;
   tert-Butyl {(1S,2R)-1-benzyl-2-[(4S)-1-(3-fluorobenzyl)-2-isopropyl-5-oxoimidazolidin-4-yl]-2-hydroxyethyl}carbamic acid;
   tert-Butyl {(1,2R)-1-benzyl-2-[(4S)-1-(4-fluorobenzyl)-2-isopropyl-5-oxoimidazolidin-4-yl]-2-hydroxyethyl}carbamic acid;
   tert-Butyl ((1S,2R)-1-benzyl-2-hydroxy-2-{(4S)-2-isopropyl-5-oxo-1-[3-(trifluoromethoxy)benzyl]imidazolidin-4-yl}ethyl)carbamic acid;
   tert-Butyl ((1S,2R)-1-benzyl-2-{(4S)-1-[2-fluoro-4-(trifluoromethyl)benzyl]-2-isopropyl-5-oxoimidazolidin-4-yl}-2-hydroxyethyl)carbamic acid;
   tert-Butyl {(1S,2R)-1-benzyl-2-[(2S,4S)-1-benzyl-2-ethyl-5-oxoimidazolidin-4-yl]-2-hydroxyethyl}carbamic acid;
   tert-Butyl {(1S,2R)-1-benzyl-2-[(4S)-1-benzyl-2-methyl-5-oxoimidazolidin-4-yl]-2-hydroxyethyl}carbamic acid;
   tert-Butyl {(1S,2R)-1-benzyl-2-[(4S)-1-benzyl-5-oxo-2-propylimidazolidin-4-yl]-2-hydroxyethyl}carbamic acid;
   tert-Butyl {(1S,2R)-1-benzyl-2-[(4S)-1-benzyl-2-butyl-5-oxoimidazolidin-4-yl]-2-hydroxyethyl}carbamic acid;
   tert-Butyl {(1S,2R)-1-benzyl-2-[(4S)-1-benzyl-2-isopropyl-5-oxoimidazolidin-4-yl]-2-hydroxyethyl}carbamic acid;
   Phenyl {(1S,2R)-1-benzyl-2-[(4S)-1-benzyl-2-isopropyl-5-oxoimidazolidin-4-yl]-2-hydroxyethyl}carbamic acid;
   Phenyl {(1S,2R)-1-benzyl-2-[(2S,4S)-1-benzyl-2-butyl-5-oxoimidazolidin-4-yl]-2-hydroxyethyl}carbamic acid;
   Phenyl {(1S,2R)-1-benzyl-2-[(6S)-8-benzyl-7-oxo-5,8-diazaspiro[3.4]oct-6-yl]-2-hydroxyethyl}carbamic acid;
   Phenyl {(1S,2R)-1-benzyl-2-[(2S)-4-benzyl-3-oxo-8-oxa-1,4-diazaspiro[4.5]dec-2-yl]-2-hydroxyethyl carbamic acid;

Phenyl {(1S,2R)-1-benzyl-2-[(2S)-4-benzyl-8-methyl-3-oxo-1,4-diazaspiro[4.5]dec-2-yl]-2-hydroxyethyl}carbamic acid Phenyl {(1S,2R)-1-benzyl-2-[(4S)-1-benzyl-2,2-dibutyl-5-oxoimidazolidin-4-yl]-2-hydroxyethyl}carbamic acid;

Phenyl {(1S,2R)-1-benzyl-2-[(2S)-4-benzyl-3-oxo-1,4-diazaspiro[4.4]non-2-yl]-2-ydroxyethyl}carbamic acid;

Phenyl {(1S,2R)-1-benzyl-2-[(4S)-1-benzyl-5-oxo-2-phenylimidazolidin-4-yl]-2-hydroxyethyl}carbamic acid;

Phenyl ((1S,2R)-1-benzyl-2-{(4S)-2-butyl-5-oxo-1-[(1S)-1-phenylethyl]imidazolidin-4-yl}-2-hydroxyethyl)carbamic acid;

N-[(1S)-1-Benzyl-2-(1-benzyl-2,2-dimethyl-5-oxoimidazolidin-4-yl)-2-hydroxyethyl]-N'-[(1R)-1-(4-Fluorophenyl)ethyl]-5-[1-(methylsulfonyl)ethyl]isophthalamic acid;

N-[(1S)-1-Benzyl-2-(1-benzyl-2,2-dimethyl-5-oxoimidazolidin-4-yl)-2-hydroxyethyl]-2-(4-butyl-2,3-dioxopiperazin-1-yl)acetamide;

N'-[(1S)-1-Benzyl-2-(1-benzyl-2,2-dimethyl-5-oxoimidazolidin-4-yl)-2-hydroxyethyl]-N,N-dipropylisophthalamic acid;N-[(1S)-1-Benzyl-2-(1-benzyl-2,2-dimethyl-5-oxoimidazolidin-4-yl)-2-hydroxyethyl] benzamide; N-[(1S)-1-Benzyl-2-(1-benzyl-2,2-dimethyl-5-oxoimidazolidin-4-yl)-2-hydroxyethyl]-2-phenylacetamide; tert-Butyl [(1S)-1-benzyl-2-(1-benzyl-2,2-dimethyl-5-oxoimidazolidin-4-yl)-2-hydroxyethyl]carbamic acid; Phenyl [(1S)-1-benzyl-2-(1-benzyl-2,2-dimethyl-5-oxoimidazolidin-4-yl)-2-hydroxyethyl]carbamic acid;

N-[(1S)-1-benzyl-2-(1-benzyl-2,2-dimethyl-5-oxoimidazolidin-4-yl)-2-hydroxyethyl]acetamide;

tert-Butyl [(1S)-1-benzyl-2-(1-benzyl-2-methyl-5-oxoimidazolidin-4-yl)-2-hydroxyethyl]carbamic acid;

tert-Butyl3-benzyl-5-{(2S)-2-[(tert-butoxycarbonyl)amino]-1-hydroxy-3-phenylpropyl }-2-methyl-4-oxoimidazolidine-1-carboxylic acid; N-[(1S)-1-Benzyl-2-(1-benzyl-2-methyl-5-oxoimidazolidin-4-yl)-2-hydroxyethyl]-N'-[(1R)-1-(4-fluorophenyl)ethyl]-5-[methyl(methylsulfonyl)amino]isophthalamic acid;

Phenyl[(1S)-1-benzyl-2-(1-benzyl-2-methyl-5-oxoimidazolidin-4-yl)-2-hydroxyethyl]carbamic acid;

N-{(1S,2S)-1-Benzyl-2-hydroxy-2-[(4S)-1,2,2-trimethyl-5-oxoimidazolidin-4-yl]ethyl}-N'-[(1R)-1-(4-fluorophenyl)ethyl]-5-[methyl(methylsulfonyl)amino]isophthalamic acid;

5N-[(1S)-1-benzyl-2-hydroxy-2-(1,2,2-trimethyl-5-oxoimidazolidin-4-yl)ethyl]-N'-[(1R)-1-(4-fluorophenyl)ethyl]-5-[methyl(methylsulfonyl)amino]isophthalamic acid;

N-[(1S)-1-benzyl-2-(1-benzyl-2,2-dimethyl-5-oxoimidazolidin-4-yl)-2-hydroxyethyl]-2-chloro-6-(methyl{[(1S,2S)-2-methylcyclopropyl]methyl}amino)isonicotinamide;

N-[(1S)-1-benzyl-2-(1-benzyl-2,2-dimethyl-5-oxoimidazolidin-4-yl)-2-hydroxyethyl]-2-(methyl{[(1S,2S)-2-methylcyclopropyl]methyl }amino)-6-[methyl(methylsulfonyl)amino]isonicotinamide;

or a pharmaceutically acceptable salt thereof.

15. A pharmaceutical composition comprising a therapeutically effective amount of a compound of claim 1, or a pharmaceutically acceptable salt thereof, and a pharmaceutically acceptable carrier.

16. A method for treating Alzheimer's disease in a patient in need thereof comprising administering to the patient a therapeutically effective amount of a compound of claim 1, or a pharmaceutically acceptable salt thereof.

17. A compound of formula (I):

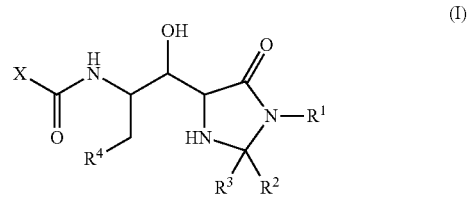

wherein:

$R^2$ is hydrogen;

$R^3$ is $C_{1-10}$ alkyl or $C_{6-10}$ aryl;

$R^1$ and $R^4$ are independently selected from the group consisting of (1) hydrogen, (2) —$C_{1-10}$ alkyl, (3) —$C_{2-10}$ alkenyl, (4) —$C_{2-10}$ alkynyl, (5) —$C_{6-10}$ aryl, or (6) heteroaryl, wherein said alkyl, alkenyl, alkynyl, aryl or heteroaryl is optionally substituted with one or more (a) halo, (b) —$C_{1-10}$ alkyl, wherein said alkyl is optionally substituted with one or more fluoro, (c) —$C_{3-12}$ cycloalkyl, (d) —OH, (e) —CN, (f) —O-$C_{1-10}$ alkyl, wherein said alkyl is optionally substituted with one or more fluoro, (g) —$C_{6-10}$ aryl, or (h) heteroaryl, and said aryl and heteroaryl is optionally substituted with one or more (i) halo, (ii) —OH, (iii) —CN, (iv) —$Q^1$-$C_{1-10}$ alkyl, wherein said alkyl is optionally substituted with one or more fluoro, (v) —$C_{1-10}$ alkyl, wherein said alkyl is optionally substituted with one or more fluoro, or (vi) —$C_{3-12}$ cycloalkyl, and $Q^1$ is selected from the group consisting of (A) —O—, (B) —$SO_2$—, (C) —NH—, to form a 3-7 carbocyclic ring structure, wherein one, two or three of the ring carbon atoms may be replaced with O, S, NH, —C(=O)— or $SO_2$, and the carbocyclic ring is optionally substituted with one or more (a) —$C_{1-10}$ alkyl, (b) —$C_{2-1}$ alkenyl, (c) —$C_{2-10}$ alkynyl, and X is selected from the group consisting of (1) —$(Q^2)_n$—$R^5$, wherein $Q^2$ is selected from the group consisting of (a) —$CH_2$—, and (b) —O—, $R^5$ is selected from the group consisting of
(a) hydrogen
(b) —$C_{1-10}$ alkyl,
(c) —$C_{2-10}$ alkenyl,
(d) —$C_{2-10}$ alkynyl, and
(e) —$C_{6-10}$ aryl,
wherein said alkyl, alkenyl, alkynyl or aryl is optionally substituted with one or more
  (i) halo,
  (ii) —$C_{1-10}$ alkyl, wherein said alkyl is optionally substituted with one or more fluoro,
  (iii) —$C_{3-12}$ cycloalkyl,
  (iv) —OH,
  (v) —CN,
  (vi) —O-$C_{1-10}$ alkyl, wherein said alkyl is optionally substituted with one or more fluoro, or
  (vii) —$C_{6-10}$ aryl; and

2)

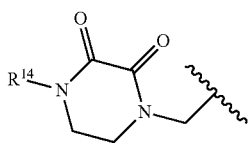

3)

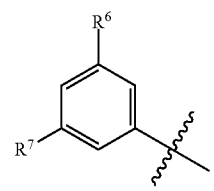

wherein R6 is selected from the group consisting of
(a) ($R^8$—$SO_2$)N($R^9$)—, wherein $R^8$ is selected from the group consisting of
  (i) —$C_{1-10}$ alkyl,
  (ii) —$C_{2-10}$ alkenyl,
  (iii) —$C_{2-10}$ alkynyl,
  (iv) —$C_{3-8}$ cycloalkyl, or
  (v) —$C_{6-10}$ aryl
  wherein said alkyl, alkenyl, alkynyl, cycloalkyl and aryl is optionally substituted with one or more
    (A) halo,
    (B) —OH,
    (C) —CN,
    (D) —O-$C_{1-10}$ alkyl,
    (E) —$C_{1-10}$ alkyl,
    (F) —$C_{2-10}$ alkenyl,
    (G) —$C_{2-10}$ alkynyl,
    (H) —$C_{3-8}$ cycloalkyl,
    (I) —$C_{6-10}$ aryl, or
    (J) heteroaryl,
    and said aryl and heteroaryl is optionally substituted with one or more
      (I) halo,
      (II) —OH,
      (III) —CN,
      (IV) —O-$C_{1-10}$ alkyl,
      (V) —$C_{3-8}$ cycloalkyl,
      (VI) —$C_{1-10}$ alkyl,
      (VII) —$C_{2-10}$ alkenyl, or
      (VIII) —$C_{2-10}$ alkynyl;

$R^9$ is selected from the group consisting of
  (i) hydrogen,
  (ii) —$C_{1-10}$ alkyl,
  (iii) —$C_{2-10}$ alkenyl,
  (iv) —$C_{2-10}$ alkynyl, or
  (v) —$C_{6-10}$ aryl,
  wherein said alkyl, alkenyl, alkynyl or aryl is optionally substituted with one or more
    (A) halo,
    (B) —OH,
    (C) —CN,
    (D) —O-$C_{1-10}$ alkyl,
    (E) —$C_{3-8}$ cycloalkyl,
    (F) —$C_{6-10}$ aryl, or
    (G) heteroaryl,
    wherein said cycloalkyl, aryl or heteroaryl is optionally substituted with one or more
      (I) halo,
      (II) —OH,
      (III) —CN,
      (IV) —O-$C_{1-10}$ alkyl,
      (V) —$C_{3-8}$ cycloalkyl, or
      (VI) —$C_{6-10}$ aryl;

(b)

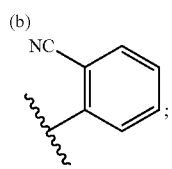

(c)

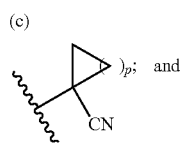
and (d) hydrogen;
and $R^7$ is selected from the group consisting of (a)

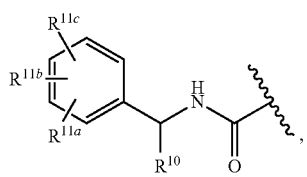

(b)

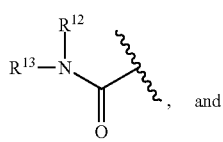
, and wherein $R^{10}$ is $C_{1-10}$ alkyl, wherein said alkyl is unsubstituted or substituted with one or more halogen;
$R^{11a}$, $R^{11b}$, and $R^{11c}$ are independently selected from the group consisting of:
  (i) hydrogen,
  (ii) halo,
  (iii) —$C_{1-10}$ alkyl,
  (iv) —OH,
  (v) —CN,
  (vi) —$C_{3-12}$ cycloalkyl, and
  (vii) —O-$C_{1-10}$ alkyl;

$R^{12}$ and $R^{13}$ are independently selected from the group consisting of
- (i) hydrogen,
- (ii) —$C_{1-10}$ alkyl,
- (iii) —$C_{2-10}$ alkenyl,
- (iv) —$C_{2-10}$ alkynyl, and
- (v) —$C_{1-10}$ alkyl-$C_{3-12}$ cycloalkyl;

wherein said alkyl, alkenyl, alkynyl and cycloalkyl is optionally substituted with one or more
- (A) halo,
- (B) —OH,
- (C) —CN,
- (D) —$C_{1-10}$ alkyl,
- (E) —O-$C_{1-10}$ alkyl,
- (F) —$C_{3-8}$ cycloalkyl,
- (G) $NR^aR^b$, wherein $R^a$ and $R^b$ are selected from the group consisting of
  - (i) hydrogen, and
  - (ii) —$C_{1-10}$ alkyl, or $R^a$ and $R^b$ are joined together with the nitrogen atom to which they are attached to form a 4-6 membered carbocyclic ring having a single nitrogen, or
- (H) —$C_{6-10}$ aryl;

or $R^{12}$ and $R^{13}$ are joined together with the nitrogen atom to which they are attached to form a 4-6 membered carbocyclic ring having a single nitrogen, wherein said carbocyclic ring is optionally substituted with one or more
- (1) —$C_{1-10}$ alkyl, wherein said alkyl is optionally substituted with one or more
  - (i) halogen,
  - (ii) hydroxy, or
  - (iii) —$C_{1-6}$ alkoxy;
- (2) —$C_{3-12}$ cycloalkyl,
- (3) $(CH_2)_m$-phenyl, wherein said phenyl is unsubstituted or substituted with one or more halogen,
- (4) $C_{2-10}$ alkenyl,
- (5) $C_{2-10}$ alkynyl,
- (6) —CN, and said alkyl, alkenyl or alkynyl $R^{12}$ and $R^{13}$ groups are optionally substituted with one or more
- (a) halo,
- (b) —OH,
- (c) —CN,
- (d) —O-$C_{1-10}$ alkyl, or
- (e) —$C_{3-12}$ cycloalkyl;

and said cycloalkyl and phenyl $R^{12}$ and $R^13$ groups are optionally substituted with one or more
- (a) halo,
- (b) —$C_{1-10}$ alkyl,
- (c) OH,
- (d) —CN,
- (e) —$C_{3-12}$ cycloalkyl, or
- (f) —O-$C_{1-10}$ alkyl;

$R^{14}$ is selected from the group consisting of
- (i) hydrogen,
- (ii) —$C_{1-10}$ alkyl;
- (iii) halo,
- (iv) —$C_{3-12}$ cycloalkyl,
- (v) —$C_{6-10}$ aryl, and
- (vi) heteroaryl, wherein said aryl and heteroaryl is optionally substituted with one or more
- (A) halo,
- (B) —OH,
- (C) —CN,
- (D) —O-$C_{1-10}$ alkyl,
- (E) —$C_{3-8}$ cycloalkyl, or
- (F) —$C_{1-10}$ alkyl;

4)

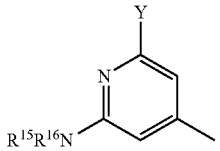

wherein Y is $R^6$ or halogen,
and $R^{15}$ and $R^{16}$ are independently selected from the group consisting of
- (1) hydrogen,
- (2) —$C_{1-10}$ alkyl,
- (3) —$C_{2-10}$ alkenyl,
- (4) —$C_{2-10}$ alkynyl, and
- (5) —$C_{1-10}$ alkylene—$C_{3-12}$ cycloalkyl;

wherein said alkyl, cycloalkyl, alkenyl or alkynyl is unsubstituted or substituted with one or more
- (a) halo,
- (b) —OH,
- (c) —CN,
- (d) —$C_{1-10}$ alkyl
- (e) —$C_{3-12}$ cycloalkyl,
- (f) —O-$C_{1-10}$ alkyl,
- (g) heteroaryl, wherein said heteroaryl may be unsubstituted or substituted with halogen;
- (h) phenyl, or
- (i) —$NR^cR^d$,
  - (I) hydrogen, and
  - (II) —$C_{1-10}$ alkyl, or Rhu c and $R^d$ are joined together with the nitrogen atom to which they are attached to form a 4-6 membered carbocyclic ring having a single nitrogen, or $R^{15}$ and $R^{16}$ are joined together with the nitrogen atom to which they are attached to form a 4-6 membered carbocyclic ring having a single nitorgen, wherein said carbocyclic ring is unsubstituted or substituted with one or more
- (a) —$C_{1-10}$ alkyl,
- (b) —$C_{3-12}$ cycloalkyl,
- (c) —$(CH_2)_n$-phenyl,
- (d) —$C_{2-10}$ alkenyl, or
- (e) —$C_{2-10}$ alkynyl, wherein said alkyl, alkenyl and alkynyl is unsubstituted or substituted with one or more
- (i) halo,
- (ii) —OH,
- (iii) —CN,
- (iv) —O-$C_{1-10}$ alkyl, or
- (v) —$C_{3-12}$ cycloalkyl;

and said cycloalkyl and phenyl is unsubstituted or substituted with one or more
- (i) halo,
- (ii) —$C_{1-10}$ alkyl,
- (iii) —OH,
- (iv) —CN,
- (v) —$C_{3-12}$ cycloalkyl, or
- (vi) —O-$C_{1-10}$ alkyl;

m is 0, 1, 2, 3 or 4;
n is 0 or 1; and
p is 1, 2, 3 or 4;
or a pharmaceutically acceptable salt thereof, and individual enantiomers and diastereomers thereof.

18. A compound of formula (I):

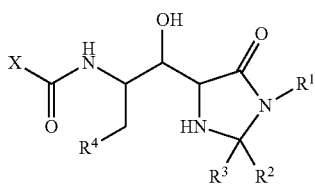

wherein:

$R^2$ and $R^3$ are each —$C_{1-10}$ alkyl;

$R^1$ and $R^4$ are independently selected from the group consisting of
- (1) hydrogen,
- (2) —$C_{1-10}$ alkyl,
- (3) —$C_{2-10}$ alkenyl,
- (4) —$C_{2-10}$ alkynyl,
- (5) —$C_{6-10}$ aryl, or
- (6) heteroaryl, wherein said alkyl, alkenyl, alkynyl, aryl or heteroaryl is optionally substituted with one or more
- (a) halo,
- (b) —$C_{1-10}$ alkyl, wherein said alkyl is optionally substituted with one or more fluoro,
- (c) —$C_{3-12}$ cycloalkyl,
- (d) —OH,
- (e) —CN,
- (f) —O-$C_{1-10}$ alkyl, wherein said alkyl is optionally substituted with one or more fluoro,
- (g) —$C_{6-10}$ aryl, or
- (h) heteroaryl, and said aryl and heteroaryl is optionally substituted with one or more
- (i) halo,
- (ii) —OH,
- (iii) —CN,
- (iv) —$Q^1$—$C_{1-10}$ alkyl, wherein said alkyl is optionally substituted with one or more fluoro,
- (v) —$C_{1-10}$ alkyl, wherein said alkyl is optionally substituted with one or more fluoro, or
- (vi) —$C_{3-12}$ cycloalkyl, and $Q^1$ is selected from the group consisting of
- (A) —O—,
- (B) —$SO_2$—,
- (C) —NH—, to form a 3-7 carbocyclic ring structure, wherein one, two or three of the ring carbon atoms may be replaced with O, S, NH, —C(=O)— or $SO_2$, and the carbocyclic ring is optionally substituted with one or more
- (a) —$C_{1-10}$ alkyl,
- (b) —$C_{2-10}$ alkenyl,
- (c) —$C_{2-10}$ alkynyl, and X is selected from the group consisting of
- (1) —$(Q^2)_n$—$R^5$, wherein $Q^2$ is selected from the group consisting of
- (a) —$CH_2$—, and
- (b) —O—, $R^5$ is selected from the group consisting of
- (a) hydrogen
- (b) —$C_{1-10}$ alkyl,
- (c) —$C_{2-10}$ alkenyl,
- (d) —$C_{2-10}$ alkynyl, and
- (e) —$C_{6-10}$ aryl, wherein said alkyl, alkenyl, alkynyl or aryl is optionally substituted with one or more
- (i) halo,
- (ii) —$C_{1-10}$ alkyl, wherein said alkyl is optionally substituted with one or more fluoro,
- (iii) —$C_{3-12}$ cycloalkyl,
- (iv) —OH,
- (v) —CN,
- (vi) —O-$C_{1-10}$ alkyl, wherein said alkyl is optionally substituted with one or more fluoro, or
- (vii) —$C_{6-10}$ aryl; and

2)

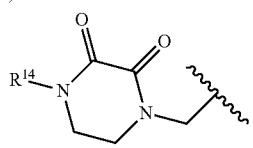

3)

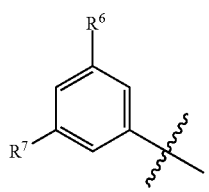

wherein $R^6$ is selected from the group consisting of
- (a) ($R^8$—$SO_2$)N($R^9$)—, wherein $R^8$ is selected from the group consisting of
  - (i) —$C_{1-10}$ alkyl,
  - (ii) —$C_{2-10}$ alkenyl,
  - (iii) —$C_{2-10}$ alkynyl,
  - (iv) —$C_{3-12}$ cycloalkyl, or
  - (v) —$C_{6-10}$ aryl wherein said alkyl, alkenyl, alkynyl, cycloalkyl and aryl is optionally substituted with one or more
- (A) halo,
- (B) —OH,
- (C) —CN,
- (D) —O-$C_{1-10}$ alkyl,
- (E) —$C_{1-10}$ alkyl,
- (F) —$C_{2-10}$ alkenyl,
- (G) —$C_{2-10}$ alkynyl,
- (H) —$C_{3-8}$ cycloalkyl,
- (I) —$C_{6-10}$ aryl, or
- (J) heteroaryl, and said aryl and heteroaryl is optionally substituted with one or more
- (1) halo,
- (II) —OH,
- (III) —CN,
- (IV) —O-$C_{1-10}$ alkyl,
- (V) —$C_{3-8}$ cycloalkyl,
- (VI) —$C_{1-10}$ alkyl,
- (VII) —$C_{2-10}$ alkenyl, or
- (VIII) —$C_{2-10}$ alkynyl;

$R^9$ is selected from the group consisting of
- (i) hydrogen,
- (ii) —$C_{1-10}$ alkyl,
- (iii) —$C_{2-10}$ alkenyl,
- (iv) —$C_{2-10}$ alkynyl, or
- (v) —$C_{6-10}$ aryl, wherein said alkyl, alkenyl, alkynyl or aryl is optionally substituted with one or more (A) halo,
(B) —OH,
(C) —CN,
(D) —O-$C_{1-10}$ alkyl,
(E) —$C_{3-8}$ cycloalkyl,
(F) —$C_{6-10}$ aryl, or
(G) heteroaryl,
wherein said cycloalkyl, aryl or heteroaryl is optionally substituted with one or more
(I) halo,
(II) —OH,
(DI) —CN,
(IV) —O-$C_{1-10}$ alkyl,
(V) —$C_{3-8}$ cycloalkyl, or
(VI) —$C_{6-10}$ aryl;

(b) 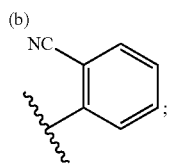

(c) 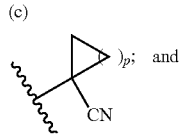 and (d) hydrogen;
and $R^7$ is selected from the group consisting of (a) 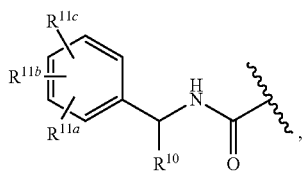

(b) 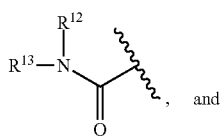 and wherein $R^{10}$ is $C_{1-10}$ alkyl, wherein said alkyl is unsubstituted or substituted with one or more halogen;
$R^{11a}$, $R^{11b}$, and $R^{11c}$ are independently selected from the group consisting of:
(i) hydrogen,
(ii) halo,
(iii) —$C_{1-10}$ alkyl,
(iv) —OH,
(v) —CN,
(vi) —$C_{3-12}$ cycloalkyl, and
(vii) —O-$C_{1-10}$ alkyl;
$R^{12}$ and $R^{13}$ are independently selected from the group consisting of
(i) hydrogen,
(ii) —$C_{1-10}$ alkyl,
(iii) —$C_{2-10}$ alkenyl,
(iv) —$C_{2-10}$ alkynyl, and
(v) —$C_{1-10}$ alkyl—$C_{3-12}$ cycloalkyl;

wherein said alkyl, alkenyl, alkynyl and cycloalkyl is optionally substituted with one or more
(A) halo,
(B) —OH,
(C) —CN,
(D) —$C_{1-10}$ alkyl,
(E) —O-$C_{1-10}$ alkyl,
(F) —$C_{3-8}$ cycloalkyl,
(G) —$NR^aR^b$, wherein $R^a$ and $R^b$ are selected from the group consisting of
(i) hydrogen, and
(ii) —$C_{1-10}$ alkyl, or $R^a$ and $R^b$ are joined together with the nitrogen atom to which they are attached to form a 4-6 membered carbocyclic ring having a single nitrogen, or
(H) —$C_{6-10}$ aryl;
or $R^{12}$ and $R^{13}$ are joined together with the nitrogen atom to which they are attached to form a 4-6 membered carbocyclic ring having a single nitrogen, wherein said carbocyclic ring is optionally substituted with one or more
(1) —$C_{1-10}$ alkyl, wherein said alkyl is optionally substituted with one or more
(i) halogen,
(ii) hydroxy, or
(iii) —$C_{1-6}$ alkoxy;
(2) —$C_{3-12}$ cycloalkyl,
(3) $(CH_2)_m$-phenyl, wherein said phenyl is unsubstituted or substituted with one or more halogen,
(4) $C_{2-10}$ alkenyl,
(5) $C_{2-10}$ alkynyl,
(6) —CN,
and said alkyl, alkenyl or alkynyl $R^{12}$ and $R^{13}$ groups are optionally substituted with one or more
(a) halo,
(b) —OH,
(c) —CN,
(d) —O-$C_{1-10}$ alkyl, or
(e) —$C_{3-12}$ cycloalkyl;
and said cycloalkyl and phenyl $R^{12}$ and $R^{13}$ groups are optionally substituted with one or more
(a) halo,
(b) —$C_{1-10}$ alkyl,
(c) OH,
(d) —CN,
(e) —$C_{3-12}$ cycloalkyl, or
(f) —O-$C_{1-10}$ alkyl;
$R^{14}$ is selected from the group consisting of
(i) hydrogen,
(ii) —$C_{1-10}$ alkyl;
(iii) halo,
(iv) —$C_{3-12}$ cycloalkyl,
(v) —$C_{6-10}$ aryl, and
(vi) heteroaryl,
wherein said aryl and heteroaryl is optionally substituted with one or more
(A) halo,
(B) —OH,
(C) —CN,
(D) —O-$C_{1-10}$ alkyl,
(E) —$C_{3-8}$ cycloalkyl, or
(F) —$C_{1-10}$ alkyl;

4)

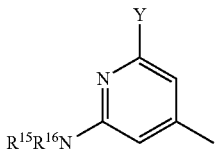

wherein Y is $R^6$ or halogen,
and $R^{15}$ and $R^{16}$ are independently selected from the group consisting of
  (1) hydrogen,
  (2) —$C_{1-10}$ alkyl,
  (3) —$C_{2-10}$ alkenyl,
  (4) —$C_{2-10}$ alkynyl, and
  (5) —$C_{1-10}$ alkylene—$C_{3-12}$ cycloalkyl;
  wherein said alkyl, cycloalkyl, alkenyl or alkynyl is unsubstituted or substituted with one or more
    (a) halo,
    (b) —OH,
    (c) —CN,
    (d) —$C_{1-10}$ alkyl
    (e) —$C_{3-12}$ cycloalkyl,
    (f) —O-$C_{1-10}$ alkyl,
    (g) heteroaryl, wherein said heteroaryl may be unsubstituted or substituted with halogen;
    (h) phenyl, or
    (i) —$NR^cR^d$,
      (I) hydrogen, and
      (II) —$C_{1-10}$ alkyl, or $R^c$ and $R^d$ are joined together with the nitrogen atom to which they are attached to form a 4-6 membered carbocyclic ring having a single nitrogen,
or $R^{15}$ and $R^{16}$ are joined together with the nitrogen atom to which they are attached to form a 4-6 membered carbocyclic ring having a single nitorgen, wherein said carbocyclic ring is unsubstituted or substituted with one or more
    (a) —$C_{1-10}$ alkyl,
    (b) —$C_{3-12}$ cycloalkyl,
    (c) —$(CH_2)_n$-phenyl,
    (d) —$C_{2-10}$ alkenyl, or
    (e) —$C_{2-10}$ alkynyl,
  wherein said alkyl, alkenyl and alkynyl is unsubstituted or substituted with one or more
    (i) halo,
    (ii) —OH,
    (iii) —CN,
    (iv) —O-$C_{1-10}$ alkyl, or
    (v) —$C_{3-12}$ cycloalkyl;
  and said cycloalkyl and phenyl is unsubstituted or substituted with one or more
    (i) halo,
    (ii) —$C_{1-10}$ alkyl,
    (iii) —OH,
    (iv) —CN,
    (v) —$C_{3-12}$ cycloalkyl, or
    (vi) —O-$C_{1-10}$ alkyl;
m is 0, 1, 2, 3 or 4;
n is 0 or 1; and
p is 1, 2, 3 or 4;
or a pharmaceutically acceptable salt thereof, and individual enantiomers and diastereomers thereof.

19. A compound of formula (I):

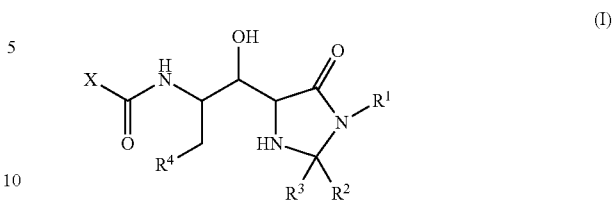

(I)

wherein:
$R^2$ and $R^3$ are linked together to form a 3-7 carbocyclic ring structure, wherein one, two or three of the ring carbon atoms may be replaced with O, S, NH, —C(=O)— or $SO_2$, and the carbocyclic ring is optionally substituted with $C_{1-10}$ alkyl;
$R^1$ and $R^4$ are independently selected from the group consisting of
  (1) hydrogen,
  (2) —$C_{1-10}$ alkyl,
  (3) —$C_{2-10}$ alkenyl,
  (4) —$C_{2-10}$ alkynyl,
  (5) —$C_{6-10}$ aryl, or
  (6) heteroaryl,
  wherein said alkyl, alkenyl, alkynyl, aryl or heteroaryl is optionally substituted with one or more
    (a) halo,
    (b) —$C_{1-10}$ alkyl, wherein said alkyl is optionally substituted with one or more fluoro,
    (c) —$C_{3-12}$ cycloalkyl,
    (d) —OH,
    (e) —CN,
    (f) —O-$C_{1-10}$ alkyl, wherein said alkyl is optionally substituted with one or more fluoro,
    (g) —$C_{6-10}$ aryl, or
    (h) heteroaryl,
    and said aryl and heteroaryl is optionally substituted with one or more
      (i) halo,
      (ii) —OH,
      (iii) —CN,
      (iv) —$Q^1$—$C_{1-10}$ alkyl, wherein said alkyl is optionally substituted with one or more fluoro,
      (v) —$C_{1-10}$ alkyl, wherein said alkyl is optionally substituted with one or more fluoro, or
      (vi) —$C_{3-12}$ cycloalkyl, and $Q^1$ is selected from the group consisting of
        (A) —O—,
        (B) —$SO_2$—,
        (C) —NH—,
  to form a 3-7 carbocyclic ring structure, wherein one, two or three of the ring carbon atoms may be replaced with O, S, NH, —C(=O)— or $SO_2$, and the carbocyclic ring is optionally substituted with one or more
    (a) —$C_{1-10}$ alkyl,
    (b) —$C_{2-10}$ alkenyl,
    (c) —$C_{2-10}$ alkynyl, and
X is selected from the group consisting of
  (1) —$(Q^2)_n$—$R^5$,
  wherein $Q^2$ is selected from the group consisting of
    (a) —$CH_2$—, and
    (b) —O—,
  $R^5$ is selected from the group consisting of
    (a) hydrogen
    (b) —$C_{1-10}$ alkyl,
    (c) —$C_{2-10}$ alkenyl,
    (d) —$C_{2-10}$ alkynyl, and
    (e) —$C_{6-10}$ aryl, wherein said alkyl, alkenyl, alkynyl or aryl is optionally substituted with one or more
(i) halo,
(ii) —$C_{1-10}$ alkyl, wherein said alkyl is optionally substituted with one or more fluoro,
(iii) —$C_{3-12}$ cycloalkyl,
(iv) —OH,
(v) —CN,
(vi) —O-$C_{1-10}$ alkyl, wherein said alkyl is optionally substituted with one or more fluoro, or
(vii) —$C_{6-10}$ aryl; and

2)

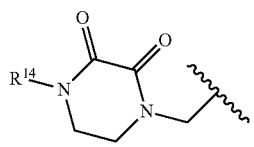

3)

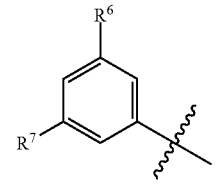

wherein $R^6$ is selected from the group consisting of
(a) ($R^8$-SOhd 2)N($R^9$)—, wherein $R^8$ is selected from the group consisting of
(i) —$C_{1-10}$ alkyl,
(ii) —$C_{2-10}$ alkenyl,
(iii) —$C_{2-10}$ alkynyl,
(iv) —$C_{3-8}$ cycloalkyl, or
(v) —$C_{6-10}$ aryl
wherein said alkyl, alkenyl, alkynyl, cycloalkyl and aryl is optionally substituted with one or more
(A) halo,
(B) —OH,
(C) —CN,
(D) —O-$C_{1-10}$ alkyl,
(E) —$C_{1-10}$ alkyl,
(F) —$C_{2-10}$ alkenyl,
(G) —$C_{2-10}$ alkynyl,
(H) —$C_{3-8}$ cycloalkyl,
(I) —$C_{6-10}$ aryl, or
(J) heteroaryl,
and said aryl and heteroaryl is optionally substituted with one or more
(I) halo,
(II) —OH,
(III) —CN,
(IV) —O-$C_{1-10}$ alkyl,
(V) —$C_{3-8}$ cycloalkyl,
(VI) —$C_{1-10}$ alkyl,
(VII) —$C_{2-10}$ alkenyl, or
(VIII) —$C_{2-10}$ alkynyl;
$R^9$ is selected from the group consisting of
(i) hydrogen,
(ii) —$C_{1-10}$ alkyl,
(iii) —$C_{2-10}$ alkenyl,
(iv) —$C_{2-10}$ alkynyl, or
(v) —$C_{6-10}$ aryl, wherein said alkyl, alkenyl, alkynyl or aryl is optionally substituted with one or more
(A) halo,
(B) —OH,
(C) —CN,
(D) —O-$C_{1-10}$ alkyl,
(E) —$C_{3-8}$ cycloalkyl,
(F) —$C_{6-10}$ aryl, or
(G) heteroaryl,
wherein said cycloalkyl, aryl or heteroaryl is optionally substituted with one or more
(I) halo,
(II) —OH,
(III) —CN,
(IV) —O-$C_{1-10}$ alkyl,
(V) —$C_{3-8}$ cycloalkyl, or
(VI) —$C_{6-10}$ aryl;

(b)

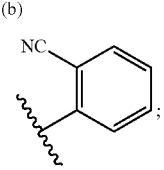

(c)

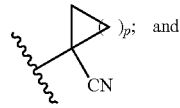

(d) hydrogen;
and $R^7$ is selected from the group consisting of (a)

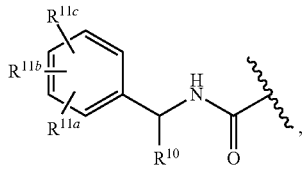

(b)

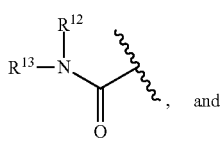

wherein $R^{10}$ is $C_{1-10}$ alkyl, wherein said alkyl is unsubstituted or substituted with one or more halogen;
$R^{11a}$, $R^{11b}$, and $R^{11c}$ are independently selected from the group consisting of
(i) hydrogen,
(ii) halo,
(iii) —$C_{1-10}$ alkyl,
(iv) —OH,
(v) —CN,
(vi) —$C_{3-12}$ cycloalkyl, and
(vii) —O-$C_{1-10}$ alkyl;
$R^{12}$ and $R^{13}$ are independently selected from the group consisting of
(i) hydrogen,
(ii) —$C_{1-10}$ alkyl, (iii) —$C_{2-10}$ alkenyl,
(iv) —$C_{2-10}$ alkynyl, and
(v) —$C_{1-10}$ alkyl—$C_{3-12}$ cycloalkyl;
wherein said alkyl, alkenyl, alkynyl and cycloalkyl is optionally substituted with one or more
(A) halo,
(B) —OH,
(C) —CN,
(D) —$C_{1-10}$ alkyl,
(E) —O-$C_{1-10}$ alkyl,
(F) —$C_{3-8}$ cycloalkyl,
(G) —$NR^aR^b$, wherein $R^a$ and $R^b$ are selected from the group consisting of
(i) hydrogen, and
(ii) —$C_{1-10}$ alkyl, or $R^a$ and $R^b$ are joined together with the nitrogen atom to which they are attached to form a 4-6 membered carbocyclic ring having a single nitrogen, or
(H) —$C_{6-10}$ aryl;
or $R^{12}$ and $R^{13}$ are joined together with the nitrogen atom to which they are attached to form a 4-6 membered carbocyclic ring having a single nitrogen, wherein said carbocyclic ring is optionally substituted with one or more
(1) —$C_{1-10}$ alkyl, wherein said alkyl is optionally substituted with one or more
(i) halogen,
(ii) hydroxy, or
(iii) —$C_{1-6}$ alkoxy;
(2) —$C_{3-12}$ cycloalkyl,
(3) $(CH_2)_m$-phenyl, wherein said phenyl is unsubstituted or substituted with one or more halogen,
(4) $C_{2-10}$ alkenyl,
(5) $C_{2-10}$ alkynyl,
(6) —CN,
and said alkyl, alkenyl or alkynyl $R^{12}$ and $R^{13}$ groups are optionally substituted with one or more
(a) halo,
(b) —OH,
(c) —CN,
(d) —$C_{1-10}$ alkyl, or
(e) —$C_{3-12}$ cycloalkyl;
and said cycloalkyl and phenyl $R^{12}$ and $R^{13}$ groups are optionally substituted with one or more
(a) halo,
(b) —O-$C_{1-10}$ alkyl,
(c) OH,
(d) —CN,
(e) —$C_{3-12}$ cycloalkyl, or
(f) —O-$C_{1-10}$ alkyl;
$R^{14}$ is selected from the group consisting of
(i) hydrogen,
(ii) —$C_{1-10}$ alkyl;
(iii) halo,
(iv) —$C_{3-12}$ cycloalkyl,
(v) —$C_{6-10}$ aryl, and
(vi) heteroaryl,
wherein said aryl and heteroaryl is optionally substituted with one or more
(A) halo,
(B) —OH,
(C) —CN,
(D) —O-$C_{1-10}$ alkyl,
(E) —$C_{3-8}$ cycloalkyl, or
(F) —$C_{1-10}$ alkyl;

4)

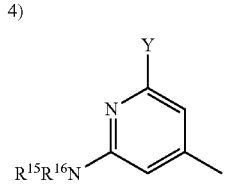

wherein Y is $R^6$ or halogen,
and $R^{15}$ and $R^{16}$ are independently selected from the group consisting of
(1) hydrogen,
(2) —$C_{1-10}$ alkyl,
(3) —$C_{2-10}$ alkenyl,
(4) —$C_{2-10}$ alkynyl, and
(5) —$C_{1-10}$ alkylene—$C_{3-12}$ cycloalkyl;
wherein said alkyl, cycloalkyl, alkenyl or alkynyl is unsubstituted or substituted with one or more
(a) halo,
(b) —OH,
(c) —CN,
(d) —$C_{1-10}$ alkyl
(e) —$C_{3-12}$ cycloalkyl,
(f) —O-$C_{1-10}$ alkyl,
(g) heteroaryl, wherein said heteroaryl may be unsubstituted or substituted with halogen;
(h) phenyl, or
(i) —$NR^cR^d$,
(I) hydrogen, and
(II) —$C_{1-10}$ alkyl, or $R^c$ and $R^d$ are joined together with the nitrogen atom to which they are attached to form a 4-6 membered carbocyclic ring having a single nitrogen,
or $R^{15}$ and $R^{16}$ are joined together with the nitrogen atom to which they are attached to form a 4-6 membered carbocyclic ring having a single nitorgen, wherein said carbocyclic ring is unsubstituted or substituted with one or more
(a) —$C_{1-10}$ alkyl,
(b) —$C_{3-12}$ cycloalkyl,
(c) —$(CH_2)_n$-phenyl,
(d) —$C_{2-10}$ alkenyl, or
(e) —$C_{2-10}$ alkynyl,
wherein said alkyl, alkenyl and alkynyl is unsubstituted or substituted with one or more
(i) halo,
(ii) —OH,
(iii) —CN,
(iv) —O-$C_{1-10}$ alkyl, or
(v) —$C_{3-12}$ cycloalkyl;
and said cycloalkyl and phenyl is unsubstituted or substituted with one or more
(i) halo,
(ii) —$C_{1-10}$ alkyl,
(iii) —OH,
(iv) —CN,
(v) —$C_{3-12}$ cycloalkyl, or
(vi) —O-$C_{1-10}$ alkyl;
m is 0, 1, 2, 3 or 4;
n is 0 or 1; and
p is 1, 2, 3 or 4;
or a pharmaceutically acceptable salt thereof, and individual enantiomers and diastereomers thereof.

* * * * *